(12) United States Patent
Bisgaier et al.

(10) Patent No.: US 10,449,154 B2
(45) Date of Patent: *Oct. 22, 2019

(54) TREATMENT OF NASH WITH GEMCABENE

(71) Applicant: Gemphire Therapeutics Inc., Livonia, MI (US)

(72) Inventors: Charles L. Bisgaier, Ann Arbor, MI (US); Daniela Carmen Oniciu, Toulouse (FR)

(73) Assignee: Gemphire Therapeutics Inc., Livonia, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/814,557

(22) Filed: Nov. 16, 2017

(65) Prior Publication Data

US 2018/0133177 A1 May 17, 2018

Related U.S. Application Data

(60) Division of application No. 15/416,911, filed on Jan. 26, 2017, now Pat. No. 9,849,104, which is a continuation of application No. PCT/US2016/060837, filed on Nov. 7, 2016.

(60) Provisional application No. 62/252,147, filed on Nov. 6, 2015, provisional application No. 62/252,195, filed on Nov. 6, 2015.

(51) Int. Cl.

| *A61K 31/194* | (2006.01) |
| *A61K 31/19* | (2006.01) |
| *A61K 9/28* | (2006.01) |
| *A61K 31/366* | (2006.01) |
| *A61K 31/40* | (2006.01) |
| *A61K 45/06* | (2006.01) |
| *A61K 31/397* | (2006.01) |
| *A61K 9/20* | (2006.01) |
| *A61K 9/48* | (2006.01) |

(52) U.S. Cl.
CPC .......... *A61K 9/2846* (2013.01); *A61K 9/2009* (2013.01); *A61K 9/2013* (2013.01); *A61K 9/2027* (2013.01); *A61K 9/2059* (2013.01); *A61K 9/2866* (2013.01); *A61K 9/2886* (2013.01); *A61K 9/4808* (2013.01); *A61K 9/4825* (2013.01); *A61K 9/4858* (2013.01); *A61K 9/4866* (2013.01); *A61K 31/194* (2013.01); *A61K 31/366* (2013.01); *A61K 31/397* (2013.01); *A61K 31/40* (2013.01); *A61K 45/06* (2013.01)

(58) Field of Classification Search
None
See application file for complete search history.

(56) References Cited

U.S. PATENT DOCUMENTS

| 5,298,627 A | 3/1994 | Butler et al. |
| 5,648,387 A | 7/1997 | Bisgaier et al. |
| 5,756,544 A | 5/1998 | Bisgaier et al. |
| 5,783,600 A | 7/1998 | Bisgaier et al. |
| 6,861,555 B2 | 3/2005 | Ando et al. |
| 8,557,835 B2 | 10/2013 | Bisgaier et al. |
| 9,849,104 B2 * | 12/2017 | Bisgaier .............. A61K 9/4808 |
| 2004/0229954 A1 | 11/2004 | MacDougall et al. |
| 2008/0176861 A1 | 7/2008 | Guha et al. |
| 2009/0186634 A1 | 7/2009 | Talley et al. |
| 2009/0186834 A1 | 7/2009 | Talley et al. |
| 2009/0312355 A1 | 12/2009 | Bachovchin et al. |
| 2012/0202849 A1 | 8/2012 | Pareek |
| 2014/0234288 A1 | 8/2014 | Grabowski |
| 2015/0005386 A1 | 1/2015 | Bisgaier |

FOREIGN PATENT DOCUMENTS

| EP | 455042 A1 | 11/1991 |
| EP | 753298 A1 | 1/1997 |
| WO | 1996030328 A1 | 10/1996 |
| WO | 1997016181 A1 | 5/1997 |
| WO | 1997016187 A1 | 5/1997 |
| WO | 1999030704 A1 | 6/1999 |
| WO | 2004045596 A1 | 6/2004 |
| WO | 2015143276 A1 | 9/2015 |

OTHER PUBLICATIONS

Musso et al. "Impact of current treatments on liver disease, glucose metabolism and cardiovascular risk in non-alcoholic fatty liver disease (NAFLD): a systematic review and meta-analysis of randomised trials," Diabetologia (2012) 55:885-904 (Year: 2012).*

Farrell et al. "Nonalcoholic Fatty Liver Disease: From Steatosis to Cirrhosis," Hepatology, Feb. 2006 (Year: 2006).*

Bays, Harold, et al. "Effectiveness and Tolerability of a New Lipid-Altering Agent, Gemcabene, in Patients with Low Levels of High-Density Lipoprotein Cholesterol", The American Journal of Cardiology, vol. 92, Sep. 1, 2003, pp. 538-543.

Brege, S. et al., "Pharmacueitcal Salts", J Pharm Sciences, 1997, pp. 1-19, vol. 66.

Chen et al., "Fibrinogen Blood Test," MedlinePlus, 2015, pp. 1-3 (https://medlineplus.gov/ency/article/003650.htm).

Cone, C. et al., "Demographic Determinants of Response to Statin Medications", Am J Healt-Syst Pharm, vol. 68, 2001, pp. 511-517.

Davidson et al., "Efficacy and Tolerability to Atorvastatin/Fenfibrate Fixed-Dose Combination Tablet Compared with Atorvastatin and Ffenofibrate Monotherapies in Patients Within Dyslipidemia: A 12-Week, Multicenter, Double-Blind, Randomized, Parrelle-Group Study," Clinical Therapeutics, 2010, pp. 2824-2836, vol. 31.

(Continued)

*Primary Examiner* — Jeffrey S Lundgren
*Assistant Examiner* — Michael J Schmitt
(74) *Attorney, Agent, or Firm* — Honigman LLP; Cynthia M. Bott; Kelly T. Murphy

(57) ABSTRACT

Methods and formulations to reduce elevated levels of lipids and apolipoprotein B in subjects having type IIb hyperlipidemia. Methods for preventing, delaying or regressing complications of lipid disorders, including; type IIb hyperlipidemia, NAFLD, and NASH. Methods for preventing or delaying primary and secondary cardiovascular events. Kits useful for such methods. Methods for reducing hepatic fibrosis. Methods for reducing plasma fibrinogen levels.

20 Claims, 22 Drawing Sheets

(56) References Cited

OTHER PUBLICATIONS

Fox, K. M. et al., "Effectiveness of Statins in Medicare-Eligible Patients and Patients < 65 Years Using Clinical Practice Data", Int J Clinc Pract, vol. 61, No. 10, 2007, pp. 1634-1642.
Friedman, et al., "Anti-Fibrotic and Anti-Inflammatory Activity of the Dual CCR2 and CCR5 Antagonist Cenicriviroc in a Mouse Model of NASH," CinicThe Liver Melting AASLD 2013, Abstract 30, 15 pages.
Goodman & Gilman's, The Pharmacological Basis of Therapeutics, (9th ed, 1996) p. 51 and 57-58.
Guha, "Classification of Dislupidaemia," Diapedia, 2014, pp. 1-5, (http://www.diapedia.org/associated-disorders/6104914178/classification-of-dyslipidaemia).
Heinonen, et al., Atorvastatin, a New HMG-CoA reductase inhibitor as monotherapy and combined with colestipol. Journal of Cardiovascular Pharmacology and Therapeutics 1996, pp. 117-122. vol. 1 No. 2.
Illingworth, et al., Influence of Lovastatin Plus Gemfibrozli on Plasma Lipids and Lipoproteins in Patients with Hetepzyous Familial Hypercholesterolemia, Circulation, 1989, pp. 590-596, vol. 79 No. 3.
Jacobson, T. A., "The Safety of Aggressive Statin Therapy: How Much Can Low-Density Lipoprotein Cholesterol Be Lowered?", Mayo Clinic Proceedings, 2006, pp. 1225-1231, vol. 81, No. 9.
Jones, P. H., "Fenofibric Acid Plus Statin Combination Therapy for the Treatment of Mixed Dyslipidemia", Clin. Lipidol., 2009, pp. 699-711, vol. 4, No. 6.
Josan, K et al., "The Efficacy and Safety of Intensive Statin Therapy: A Meta-Analysis of Randomized Trails", CMAJ, 2008, pp. 576-584, vol. 178, No. 5.
Kleiner et al., "Design and Validation of a Histological Scoring Sytem for Nonalcoholic Fatty Liver Disease," Hepatology, 2005, pp. 1313-1321, vol. 41.
Kotronen et al., "Fatter Liver a Novel Component of the Metabolic Syndrome," Arteriosclerosis, Thrombosis, and Vascular Biology, 2007, pp. 27-38, vol. 28.
Mandema, Japp W., et al. "Model-Based Development of Gemcabene, a New Lipid-Altering Agent", The AAPS Journal, 2005, pp. E513-E522, vol. 7 No. 3.
Marais, A. D. et al., "Statins in Homozygous Familial Hypercholesterolemia", Current Atherosclerosis Reports, vol. 1, 2002, pp. 19-25.
Martineau, P. et. al., "Effect of Individualizing Starting Doses of a Statin According to Baseline LDL-Cholesterol Levels on Achieving Cholesterol Targets: The Achieve Cholesterol Targets Fast With Atorvastatin Stratified Titration (ACTFAST) Study", Atherosclerosis, 2007, pp. 135-146, vol. 191.
McKenney, J. M., "Optimizing LDL-C Lowering With Statins", Am J Ther, 2004, pp. 54-59, vol. 11.
Pauciullo, et al., Efficacy and safety of a combination of fluvastatin and bezafilbrate in patients with mixed hyperlipdaema, Atheroscierosis, 2000, pp. 429-436, vol. 150.
PCT/IB2001/000026 International Search Report, dated Mar. 28, 2001 (3 pages).
PCT/US1998/024679 International Search Report, dated Apr. 6, 1999 (2 pages).
PCT/US2013/020317 International Search Report and Written Opinion dated Mar. 12, 2013 (3 pages).
PCT/US2016/60837 International Search Report and Written Opinion dated Mar. 13, 2017 (3 pages).
Rubins, et al., "Gemfibrozil for the secondary prevention of coronary heart disease in men with low levels of high-density lipoprotein cholesterol", New England Journal of Medicine 1999, pp. 410-418, vol. 341 No. 6.
Stein, E., "Results of Phase I/II Clinical Trials With Ezetimibe, a Novel Selective Cholesterol Absorption Inhibitor", European Heart Journal Supplements, 2001, pp. E11-E16, vol. 3, Suppl. E.
Tikkanen, et al., Abstract Only, "Statins: within-group comparisons, statin escape and combination therapy", Current Opinion in Lipidologv, 1996, pp. 385-388, vol. 7 No. 6.
Tolman, et al., "Treatment of Non-Alcoholic Fatty Liver Disease," Therapeutics and Clinical Risk Management, 2007, pp. 1153-1163, vol. 3, No. 6.
Vandenberg, B. F. et. al., "Management of the Patient With Statin Intolerance", Curr Atheroscler Rep, 2010, pp. 48-57, vol. 12.
Vasudevan, A. R. et. al., "Effective Use of Combination Lipid Therapy", Current Cardiology Reports, 2005, pp. 471-479, vol. 7.
Weng, T. C. et. al., "A Systematic Review and Meta-Analysis on the Therapeutic Equivalence of Statins", J Clin Pharm Ther, 2010, pp. 139-151, vol. 35.
World Health Organization Memorandum, 1972, "Classification of hyperlipidemias and hyperlipoproteinemias," 1972, Circulation, vol. XLV, pp. 501-508.
American Heart Association: "Third report of the national cholesterol education program pert panel and detection, evaluation and treatment of high blood cholesterol in adults," Circulation, 2002, pp. 3247-3331-3333, vol. 106, No. 17.
Aouizerat, B. E. et al., "A genome scan for familial combined hyperlipidemia reveals evidence of linkage with a locus on chromosome 11," Am J Hum Genet, 1999, pp. 397-412, vol. 65, No. 2.
Arai, H. et al., "Management of Type IIb Dyslipidemia", J Atheroscler Thromb, 2012, pp. 105-114, vol. 19, No. 2.
Austin, M. A. et al., "Cardiovascular disease mortality in familial forms of hypertriglyceridemia: A 20-year prospective study," Circulation, 2000, pp. 2777-2782, vol. 101, No. 24.
Ayyobi, A. F. et al., "Small, dense LDL and elevated apolipoprotein B are the common characteristics for the three major lipid phenotypes of familial combined hyperlipidemia," Arterioscler Thromb Vasc Biol, 2003, pp. 1289-1294, vol. 23, No. 7.
Babirak, S. P. et al., "Familial combined hyperlipidemia and abnormal lipoprotein lipase," Arterioscler Thromb, 1992, pp. 1176-1183, vol. 12, No. 10.
Bredie, S. J. et al., "Inherited susceptibility determines the distribution of dense low-density lipoprotein subfraction profiles in familial combined hyperlipidemia," Am J Hum Genet, 1996, pp. 812-22, vol. 58, No. 4.
Brown, G. et al., "Regression of coronary artery disease as a result of intensive lipid-lowering therapy in men with high levels of apolipoprotein B," N Engl J Med, 1990, pp. 1289-1298, vol. 323, No. 19.
Brunzell, J. D. et al., "Plasma lipoproteins in familial combined hyperlipidemia and monogenic familial hypertriglyceridemia," J Lipid Res, 1983, pp. 147-155, vol. 24, No. 2.
Cabezas, M. C. et al., "Postprandial apolipoprotein B100 and B48 metabolism in familial combined hyperlipidaemia before and after reduction of fasting plasma triglycerides," Euro J Clin Inves, 1994, pp. 669-678, vol. 24, No. 10.
Chaipichit, N. et al., "Statin adverse effects: patients' periences and laboratory monitoring of muscle and liver injuries", Int J Clin Pharm, 2015, pp. 355-364, vol. 37.
Chait, A. et al., "Very low density lipoprotein overproduction in genetic forms of hypertriglyceridemia," Eur J Clin Invest, 1980, pp. 17-22, vol. 10, No. 1.
De Graaf, J. et al., "Defects of lipoprotein metabolism in familial combined hyperlipidemia," Curr Opin Lipidol, 1998, pp. 189-196, vol. 9, No. 3.
Gagne, E. et al., "Analysis of DNA changes in the LPL gene in patients with familial combined hyperlipidemia," Arterioscler Throm, 1994, pp. 1250-1257, vol. 14, No. 8.
Goldstien, J. L. et al., "hyperlipidemia in coronary heart disease. II. Genetic analysis of lipid levels in 176 families and delineation of a new inherited disorder, combined hyperlipidemia," J Clin Invest, 1973, pp. 1544-1568, vol. 52, No. 7.
Guyton, J. R. et al, "An assessment by the Statin Intolerance Panel: 2014 update," J Clin Lipidol, 20174, pp. S72-S81, vol. 8.
Hattori, Y. et al., "Development of approximate formula for LDL-chol, LDL-apo B and LDL-chol/LDL-apo B as ndices of hyperapobetalipoproteinemia and small dense LDL," Atherosclerosis, 1998, pp. 289-299, vol. 138, No. 2.

(56) References Cited

OTHER PUBLICATIONS

Kobayashi, M. et al., "Association between risk of myopathy and cholesterol-lowering effect: A comparison of all statins," Life Sciences, 2008, pp. 969-975, vol. 82.

Rallidis, L. S. et al., "Is Myopathy the Achilles' Heel of Statins? Differences Between the New Cholesterol Treatment Guidelines and Everyday Clinical Practice," JACC, 2014, pp. 2297-2303, vol. 63, No. 21.

Ribeiro, Rodrigo A., " Impact of statin dose on major cardiovascular events: A mixed treatment comparison meta-analysis involving more than 175,000 patients," Int J Cardol, 2013, pp. 431-439, vol. 166.

Sakaeda, T. et al., "Statin-Associated Muscular and Renal Adverse Events: Data Mining of the Public Version of the FDA Adverse Event Reporting System," PLoS ONE, 2011, pp. 1-5, vol. 6, No. 12.

Skottheim, I. B., "Statin induced myotoxicity: the lactone forms are more potent than the acid forms in human skeletal muscle cells in vitro," Euro J Pharm Sci, 2008, pp. 317-325, vol. 33.

Stone, N. J., "0213 ACC/AHA Guideline on the Treatment of Blood Cholesterol to Reduce Atherosclerotic Cardiovascular Risk in Adults," J. Am. Coll. Cardiol, 2014, pp. 2889-2934, vol. 63, No. 25.

Targher, G. et al., "NASH predicts plasma inflammatory biomarkers independently of visceral fat in men," Obesity, 2008, pp. 1394-1399, vol. 16, No. 6.

Venkatesan, S. et al., "Stable isotopes show a direct relation between VLDL apoB overproduction and serum triglyceride levels and indicate a metabolically and biochemically coherent basis for familial combined hyperlipidemia," Arterioscler Throm, 1993, pp. 1110-1118, vol. 13, No. 7.

Zhang, T., "Physiologically based pharmacokinetic modeling of disposition and drug-drug interactions for atorvastatin and its metabolites," European J Pharm Sci, 2015, pp. 216-229, vol. 77.

Bisgaier et al., "Abstract 17824: Gemcabene and Atorvastatin Alone and Combined Markedly Reduce LDL-C in LDL Receptor-deficient Mice, a Model of Homozygous Familial Hypercholesterolemia," Circulation, Nov. 10, 2015, vol. 132, Iss. Suppl 3, p. A17824.

Cocciolillo S. et al., "P.16.11 1-10 Observational Trial Through Contrast Enhanced Ultrasound (CEUS) and FibroScan of Patients With Non Alcoholic Steato-Hepatitis (NASH) and Dyslipidemia (Type 2A or 2B) Undergoing Simvastatin Treatment", 20th National Congress of Digestive Diseases/Digestive and Liver Disease, Mar. 1, 2014, vol. 46, pp. S117-S118.

Kimura Y. et al., "Atorvastatin decreases serum levels of advanced glycation endproducts (AGEs) in nonalcoholic steatohepatitis (NASH) patients with dyslipidemia: clinical usefulness of AGEs as a biomarker for the attenuation of NASH", Journal of Gastroenterology, vol. 45, No. 7, Jan. 30, 2010, pp. 750-757. Abstract Only.

NCT02591836 "Efficacy and Safety of Gemcabene in Hypercholesterolemic Patients as Monotherapy or in Combination With Atorvastatin—Full Text View—ClinicalTrials.gov", Oct. 30, 2015, Retrieved from the Internet: URL:https://clinicaltrials.gov/ct2/show/NCT02591836, 7 pages.

EP3370713, Supplementary Partial EP Search Report, dated Jun. 18, 2019, 15 pages.

* cited by examiner

TREATMENT OF NASH WITH GEMCABENE

CROSS REFERENCE TO RELATED APPLICATIONS

This application is a divisional of U.S. application Ser. No. 15/416,911, which is a continuation of PCT Application No. PCT/US2016/060837, filed Nov. 7, 2016, which claims the benefit of priority to U.S. Provisional Application Ser. No. 62/252,195, filed on Nov. 6, 2015, and 62/252,147, filed on Nov. 6, 2015. The entire contents of which are incorporated herein by reference.

FIELD OF THE INVENTION

This invention relates to the use of a statin in combination with gemcabene for the treatment of mixed dyslipidemia.

BACKGROUND

The Fredrickson classification system for hyperlipidemia uses plasma appearance, total cholesterol and triglyceride values to characterize subjects with one of five types of hyperlipidemia. The five types are I, II, III, IV and V. Type II is further subdivided in to type IIa and type IIb, whereby both types have elevated total cholesterol and LDL-C, type IIb also presents with elevated triglycerides.

Reports have estimated the prevalence of type IIb hyperlipidemia (type IIb) in the population at about 10%. Type IIb is characterized by elevation in LDL-C, triglyceride, and apolipoprotein B levels, and an increased level of very low density lipoprotein cholesterol (VLDL-C), intermediate density lipoprotein cholesterol (IDL), and small dense LDL.

Type IIb hyperlipidemia encompasses acquired combined hyperlipidemia and familial combined hyperlipidemia (FCHL). FCHL is a genetic condition, occurring in approximately 0.3-2% of the population, although estimates as high as 5.7% of the population have been reported. Individuals with type IIb hyperlipidemia have an increased rate of cardiovascular disease and those individual with FCHL have a high incidence of premature coronary artery disease. In addition, type IIb patients have a higher incidence of non-alcoholic fatty liver disease (NAFLD) and non-alcoholic steatosis hepatitis (NASH) than do patients without type IIa, a form of fatty liver, that develops due to hepatic triglyceride overproduction and accumulation. NAFLD, NASH or fatty liver can lead to metabolic complications including elevation of liver enzymes, fibrosis, cirrhosis, hepatocellular carcinoma, and liver failure. Liver failure is life-threatening and therefore there is an urgent need to develop therapies to delay development, prevent formation or reverse the condition of a fatty liver.

Current treatment options for type IIb hyperlipidemia are limited. While statin are very effective at lowering LDL-C, in general they are not very effective at lowering triglyceride levels. Some statins at high dose levels, for example atorvastatin at 80 mg, do significantly lower triglyceride levels. However, high dose statin therapy can cause muscle pain (myalgia) and is often not well tolerated by patients. In addition, high dose statin therapy carries with it an increased risk for serious muscle toxicity such as rhabdomyolysis.

Further, because certain statins are metabolized by cytochrome P450 enzymes that also mediate metabolism of other drugs, the use of higher doses of statins may be contraindicated for use with certain drugs. The finding, disclosed in the present application, that a combination of gemcabene and low to moderate dose of a statin cause surprising synergy in the lowering of triglycerides (TG) may allow the use of lower doses of statin and therefore a better safety profile.

Treatments for type IIb hyperlipidemia focus on lowering LDL-C levels and triglyceride levels. Treatment typically includes administering a combination of a cholesterol lowering agent, such as a statin, and a triglyceride lowering agent, such as a fibrate, niacin or fish oil. However, the commonly used triglyceride lowering agents may not be convenient or may not be well tolerated, for example, fibrates are associated with myalgia and an increased risk of muscle toxicity, fish oil needs to be taken multiple times daily, and niacin causes flushing particularly when administered in combination with statins. Certain fibrates use or activate the cytochrome P450 3A4 isoform as part of their catabolic process as do some statins, and administration of these drugs in combination can increase the risk of myalgia and muscle damage. Physicians may avoid combining a statin with fibrates because of concern over the higher risk of muscle damage with the combination.

Nonalcoholic fatty liver disease (NAFLD) is increasingly common around the world, especially in western nations. In the United States, it is the most common form of chronic liver disease, affecting an estimated 80 to 100 million people. Nonalcoholic fatty liver disease is an umbrella term for a range of liver conditions affecting people who drink little to no alcohol. As the name implies, the main characteristic of nonalcoholic fatty liver disease is too much fat stored in liver cells. It is normal for the liver to contain some fat. However, if more than 5%-10% percent of the liver's weight is fat, the condition is called a fatty liver (steatosis). NAFLD is strongly associated with features of metabolic syndrome, including obesity, insulin resistance, type-2 diabetes mellitus, and dyslipidemia; it is considered the hepatic manifestation of this syndrome.

Pediatric NAFLD is currently the primary form of liver disease among children. Studies have demonstrated that abdominal obesity and insulin resistance are thought to be key contributors to the development of NAFLD. Because obesity is becoming an increasingly common problem worldwide the prevalence of NAFLD has been increasing concurrently. The only treatment shown to be truly effective in pediatric NAFLD is weight loss.

The more severe form of NAFLD is called non-alcoholic steatohepatitis (NASH). NASH causes the liver to swell and become damaged. NASH tends to develop in people who are overweight or obese, or have diabetes, high cholesterol or high triglycerides or inflammatory conditions. NASH, a potentially serious form of the disease, is marked by hepatocyte ballooning and liver inflammation, which may progress to scarring and irreversible damage. This damage is similar to the damage caused by heavy alcohol use. Macro and microscopically, NASH is characterized by lobular and/or portal inflammation, varying degrees of fibrosis, hepatocyte death and pathological angiogenesis. At its most severe, NASH can progress to cirrhosis, hepatocellular carcinoma and liver failure. Currently NAFLD and NASH are being treated e.g., by diet, treatment of insulin resistance or vitamin administration, such as vitamins E or D. Unfortunately there are currently no drugs approved for the treatment of NAFLD or NASH.

NAFLD Activity score (NAS) can be calculated according to the criteria of Kleiner (Kleiner D E. et al., Hepatology, 2005; 41:1313). NAS scores 0-2 are not considered diagnostic for NASH, NAS scores of 3-4 are considered either not diagnostic, borderline or positive for NASH, while NAS scores of 5-8 are largely considered diagnostic for NASH. A treatment effect for NASH includes the regression, stabilization or a reduction in the rate of disease progression. Sequential liver biopsies from a patient that may have NASH can be used to assess the change in the NAS score and used as an indication of the change in the disease state. A score that increases suggests progression, an unchanged score suggests stabilization, while a decreased score suggests regression of NASH. In a controlled clinical trial, the difference in NAS scores between the placebo and the test article treatment group, assessed usually over a duration of 6 months to two years, can be indicative of a treatment effect, even if both groups are progressing. A defined point spread is usually required by a regulatory authority to demonstrate a meaningful change in NASH.

Fibrinogen (factor I) is a mammalian glycoprotein that plays a role in the in the formation of blood clots. Fibrinogen is converted to fibrin by thrombin during blood clot formation. Fibrinogen is synthesized in liver hepatocytes. A variety of diseases are associated with elevated levels of fibrinogen and include but are not limited to NASH, microvascular disease, peripheral vascular disease, peripheral artery disease, critical limb ischemia in peripheral arterial occlusive disease, new-onset coronary atherosclerosis, decreased survival in cancer, such as in breast cancer, renal cell carcinoma, prostate cancer patients. Increased fibrinogen levels are also associated with a negative sepsis outcome, diabetes, metabolic syndrome, and subacute thyroiditis, plasma triglyceride, obesity, ultrasound intra-abdominal fat, diastolic blood pressure, insulin resistance, LDL-cholesterol and cigarette smoking. Severity of obstructive sleep apnea is also associated with elevated plasma fibrinogen in otherwise healthy patients.

Fibrinogen therefore may be a prognostic indicator or blood marker for many disease and may also serve to effect the onset and progression of the disease state. There is a medical need to reduce fibrinogen in a subject with elevated levels.

Because the treatment options are limited for patient having type IIb hyperlipidemia and because the current treatments may increase the risk of serious side effects or may not be well tolerated, there is a need for additional treatments that are safe and effective for treating patients suffering from type IIb hyperlipidemia. Additionally, the current treatments for NAFLD and NASH are limited, there is a need for more treatment options that are safe and effective for treating patients suffering from NAFLD and NASH.

SUMMARY

The present invention addresses these needs. We have shown that treatment of patients with type IIb hyperlipidemia with a combination of certain doses of gemcabene and a low or moderate dose of a statin show a reduction in both LDL-C and an unexpected more than additive reduction of triglycerides (TG) when compared to the effects of each agent alone. Gemcabene does not significantly affect the activity or expression of the main cytochrome P450 enzymes involved in the metabolism of pharmaceutical agents. Gemcabene, therefore, may reduce the need for the use of high dose statins thereby reducing the risk of side effects.

The first aspect of the invention provides methods for treating a subject having type IIb hyperlipidemia comprising administering to the subject gemcabene in combination with a low or moderate dose of a statin. In some embodiments of the first aspect of the invention the gemcabene and the statin are administered as a fixed dose combination.

A second aspect of the present invention provides a method for reducing the accumulation of liver fat in the subject comprising administering gemcabene alone or in combination with a statin. In some embodiments of the second aspect of the invention, the method is a method of treating or preventing non-alcoholic fatty liver disease (NAFLD). In another embodiment of the second aspect is a method of treating or preventing steatosis. In some embodiments the method is a method of treating or preventing liver disease wherein the liver disease is non-alcoholic steatohepatitis (NASH).

A third aspect of the invention provides specific fixed dose combinations of gemcabene and a statin.

A fourth aspect provides for kits for treating a subject having type IIb hyperlipidemia and/or NASH comprising gemcabene, a statin and instructions for use.

A fifth aspect of the present invention provides methods for reducing fibrosis in a patient comprising administering gemcabene alone or in combination with a statin.

A sixth aspect of the present invention provides method for reducing fibrinogen levels in blood plasma levels of a subject having an elevated blood plasma fibrinogen level comprising administering gemcabene alone or in combination with a statin.

One embodiment of the first aspect is a method for treating a subject having type IIb hyperlipidemia comprising, administering to the subject gemcabene in combination with a low or moderate dose of a statin.

Another embodiment of the first aspect is a method of treating a subject having type IIb hyperlipidemia comprising administering to the subject a daily dose of gemcabene from about 50 mg to about 750 mg and a daily dose of a statin from about 1 mg to about 60 mg.

One embodiment of the second aspect is a method of reducing the accumulation of liver fat in a subject comprising administering to a subject in need thereof gemcabene in a daily dose of about 50 mg to about 750 mg and administering a statin in a daily dose from about 1 mg to about 80 mg.

An embodiment of the fourth aspect of the present invention provides a kit comprising fixed dose combination comprising from about 1 mg to about 60 mg of a statin and from about 300 mg to about 600 mg of gemcabene; and instructions for the use thereof. In some embodiments, the statin is selected from atorvastatin, rosuvastatin, simvastatin, pravastatin, lovastatin, fluvastatin, and pitavastatin; or any pharmaceutically acceptable salts thereof. In some embodiments, the statin is atorvastatin.

One embodiment of the fifth aspect is a method for reducing fibrosis in a subject comprising administering to a subject in need thereof gemcabene in a daily dose of about 50 mg to about 750 mg and administering a statin in a daily dose from about 1 mg to about 80 mg.

One embodiment of the sixth aspect of the invention is a method for reducing blood plasma levels of fibrinogen in a subject with a fibrinogen level above 300 mg/dL comprising administering to the subject, gemcabene alone or in combination with a statin. The subject may have high LDL-C level. The subject may be risk for developing coronary heart disease or have already had one or more cardiac events.

BRIEF DESCRIPTION OF THE DRAWINGS

The following figures are provided by way of example and are not intended to limit the scope of the claimed invention.

DETAILED DESCRIPTION

Definitions

Figure 1A:
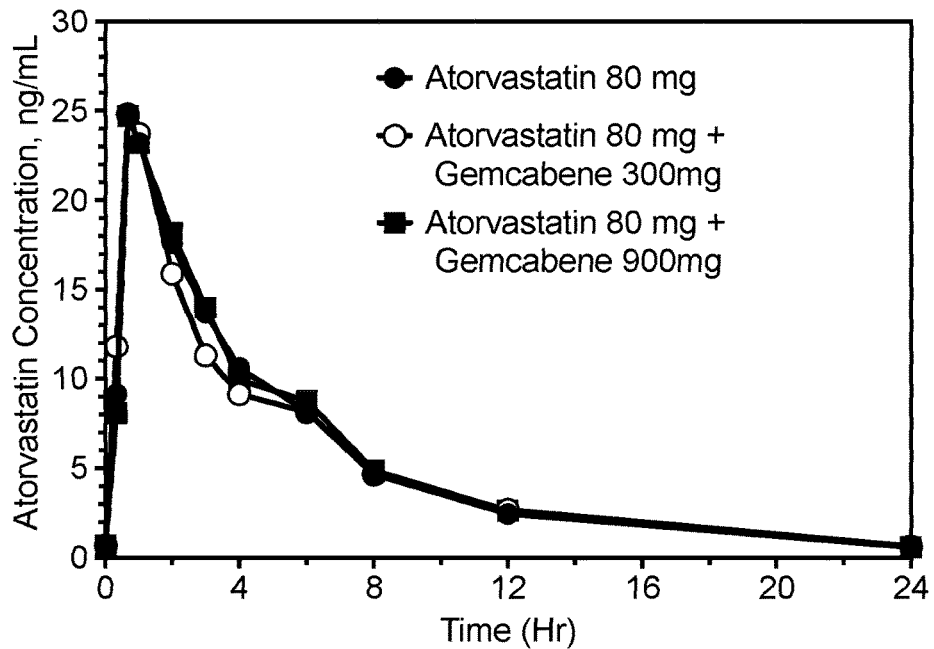
FIG. 1A is a graph showing the effect of gemcabene on concentration of atorvastatin where atorvastatin is administered alone at 80 mg (closed circles), and in combination with 300 mg gemcabene (open circles), or in combination with 900 mg of gemcabene (closed squares) in a crossover study in human subjects.
Figure 1B:
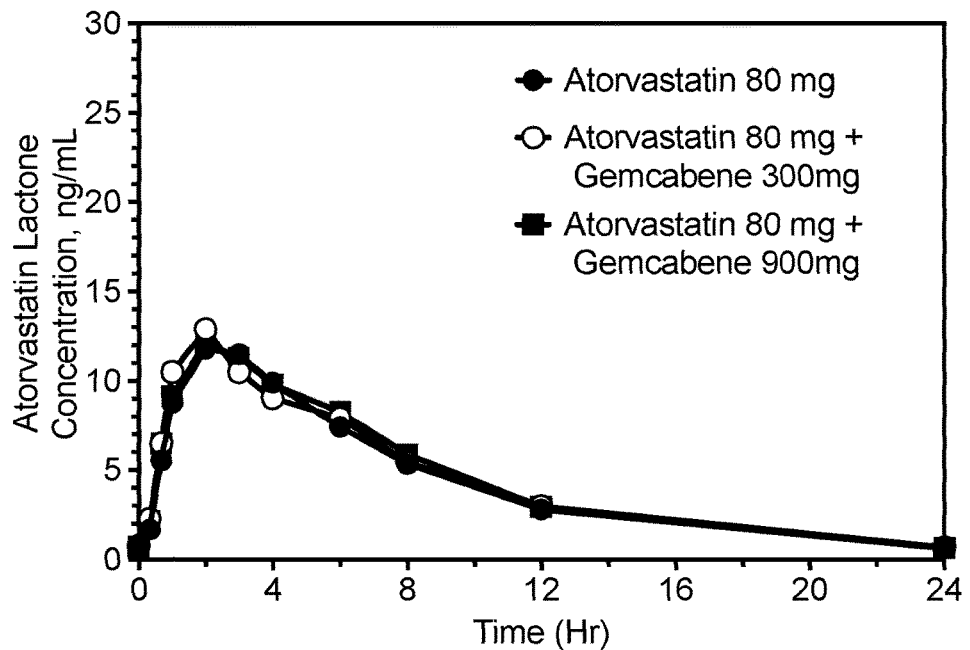
FIG. 1B is a graph showing the effect of gemcabene on concentration of atorvastatin lactone when atorvastatin is administered alone at 80 mg (closed circles), and in combination with 300 mg gemcabene (open circles), or in combination with 900 mg of gemcabene (closed squares) in a crossover study in human subjects.
Figure 1C:
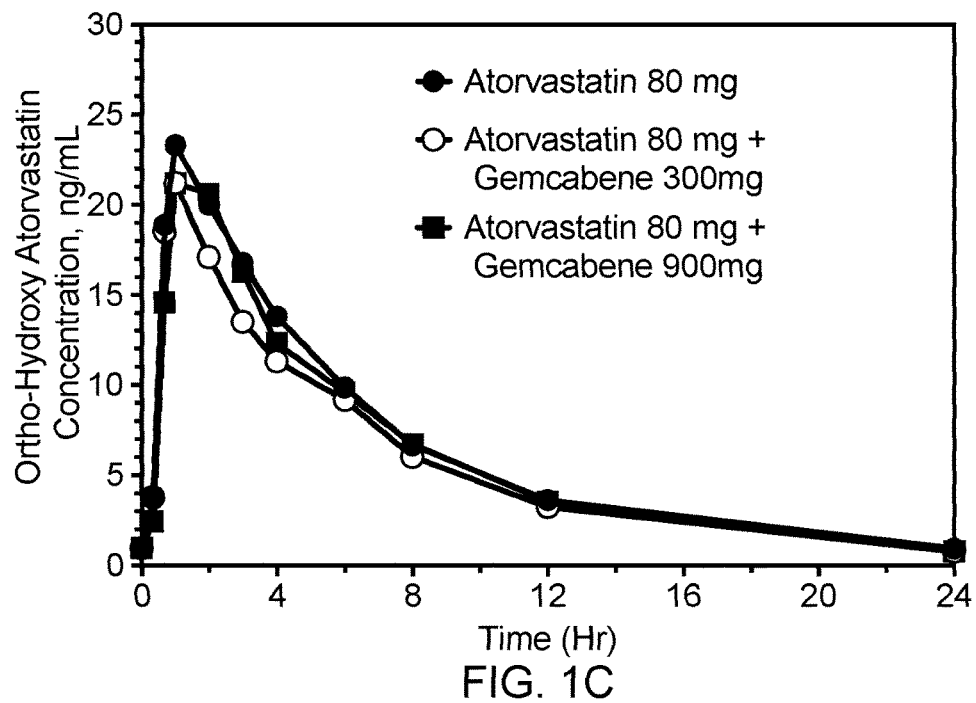
FIG. 1C is a graph showing the effect of gemcabene on concentration of ortho-hydroxy atorvastatin when atorvastatin is administered alone at 80 mg (closed circles), and in combination with 300 mg gemcabene (open circles), or in combination with 900 mg of gemcabene (closed squares) in a crossover study in human subjects.
Figure 1D:
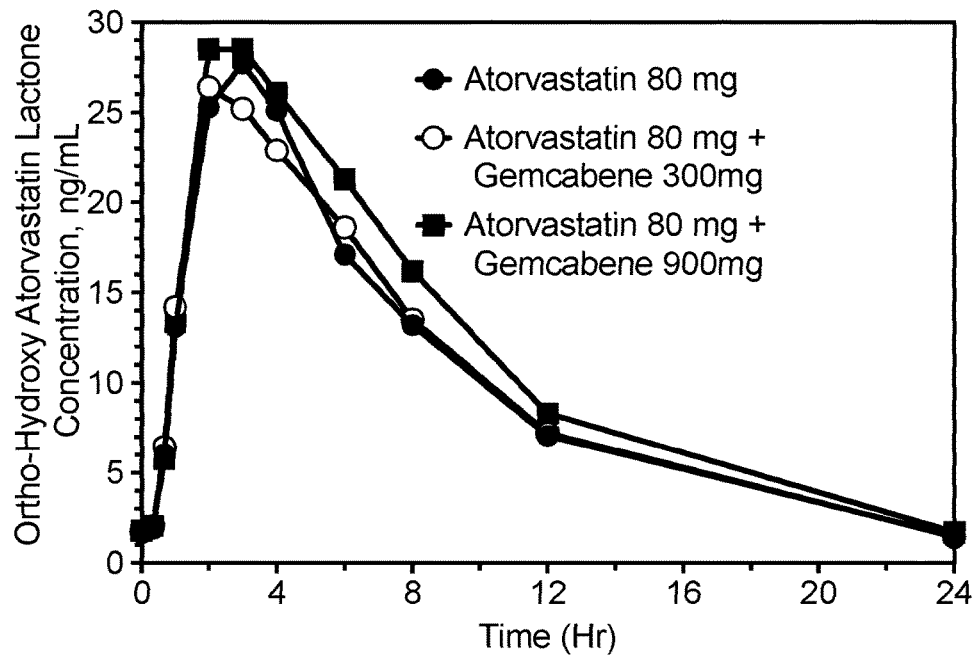
FIG. 1D is a graph showing the effect of gemcabene on concentration of ortho-hydroxy atorvastatin lactone when atorvastatin is administered alone at 80 mg (closed circles), and in combination with 300 mg gemcabene (open circles), or in combination with 900 mg of gemcabene (closed squares) in a crossover study in human subjects.
Figure 1E:
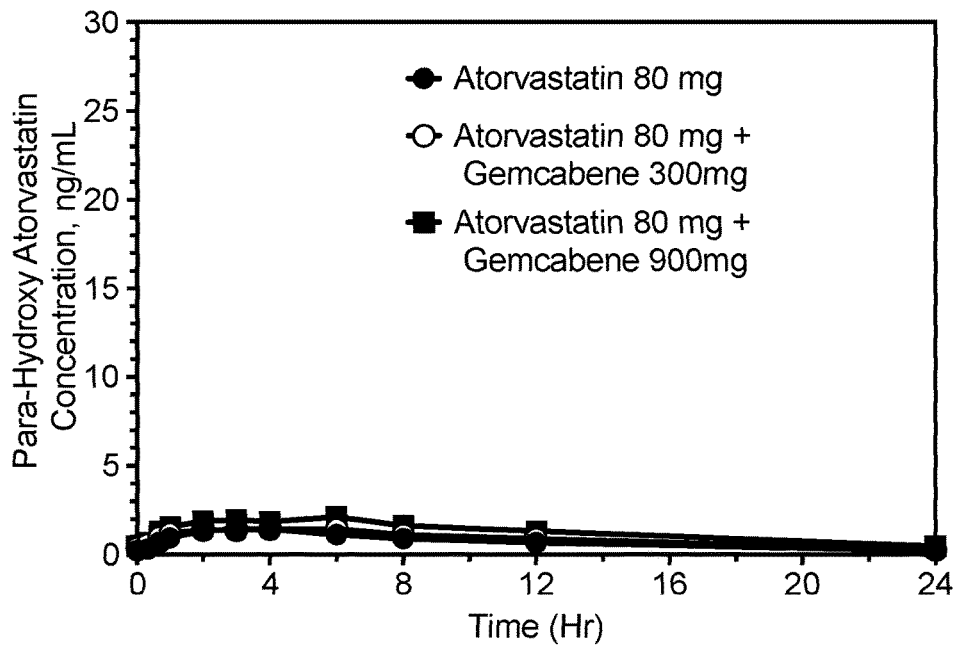
FIG. 1E is a graph showing the effect of gemcabene on concentration of para-hydroxy atorvastatin when atorvastatin is administered alone at 80 mg (closed circles), and in combination with 300 mg gemcabene (open circles), or in combination with 900 mg of gemcabene (closed squares) in a crossover study in human subjects.
Figure 1F:
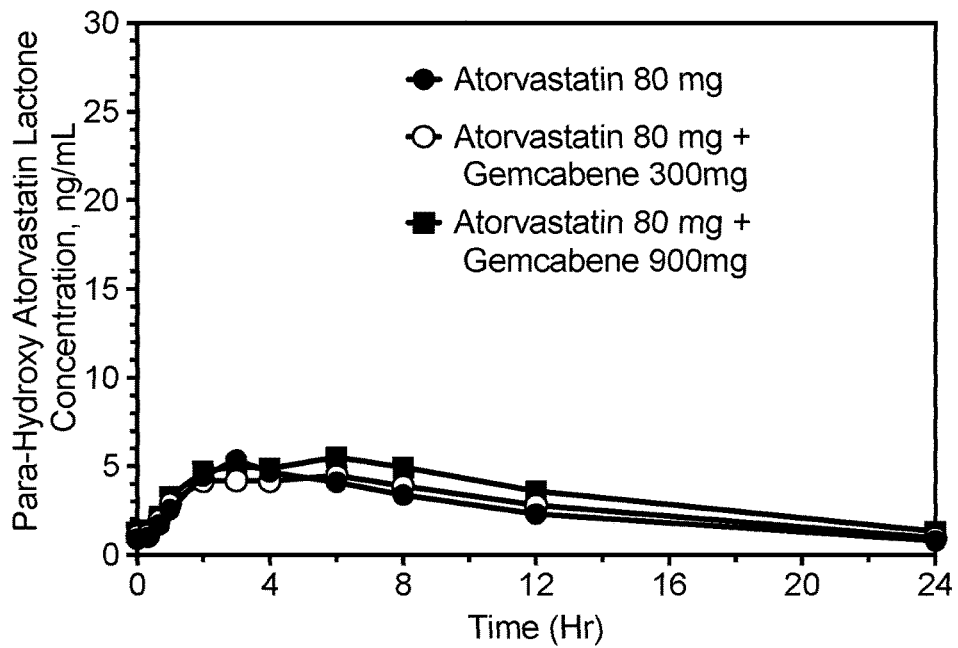
FIG. 1F is a graph showing the effect of gemcabene on concentration of para-hydroxy atorvastatin lactone when atorvastatin is administered alone at 80 mg (closed circles), and in combination with 300 mg gemcabene (open circles), or in combination with 900 mg of gemcabene (closed squares) in a crossover study in human subjects.

"API" is an abbreviation for active pharmaceutical ingredient.

Statins are a class of drugs that inhibit the enzyme HMG-CoA reductase and are generally known to lower LDL cholesterol in patients. Examples of statins include atorvastatin, rosuvastatin, simvastatin, pravastatin, lovastatin, fluvastatin, and pitavastatin.

As used herein "type IIb hyperlipidemia" or "type IIb" patient population means a patient population having a fasting LDL cholesterol blood plasma level ≥130 mg/dl and a fasting triglyceride blood plasma level ≥150 mg/dL. References to LDL-C, triglyceride or ApoB levels are fasting levels unless clearly indicated otherwise. Type IIb hyperlipidemia is also known as Type IIb hyperlipoproteinemia. In some references type IIb hyperlipidemia is referred to as mixed dyslipidemia or is described as a subset of mixed dyslipidemia.

As used herein, the term "gemcabene" refers to the compound 6,6'-oxybis(2,2-dimethylhexanoic acid) having the structure

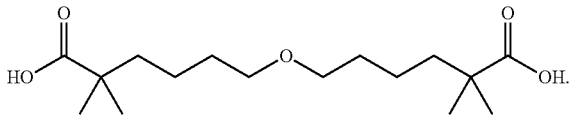 [SMILES: CC(C)(CCCCOCCCCC(C)(C)C(=O)O)C(=O)O]

Gemcabene calcium refers to the monocalcium salt of gemcabene. Gemcabene calcium is used interchangeable with gemcabene.

As used herein: "steatosis" is interchangeable with "fatty liver" which is an accumulation of fat in the liver.

When referring to dosages and doses, the dosage or dose is calculated on the weight of the API. In some embodiments, the API may be administered as a pharmaceutically acceptable salt. Where the API is administered as a salt, the dose is still calculated on the basis of the API. For example a reference to a dose of 80 mg of atorvastatin calcium means the dose of atorvastatin calcium that is equivalent to 80 mg of atorvastatin, and reference to a dose of 300 mg of gemcabene calcium means the dose of gemcabene calcium that is equivalent to 300 mg of gemcabene.

As used herein, the term "single dose formulation" or "fixed dose combination" refers to a pharmaceutical composition in the form in which it is marketed for use, formulated with mixture of two or more APIs and one or more excipients, along with other optional non-reusable material that may not be considered either ingredient or packaging (e.g., a capsule shell). As used herein, the terms "single dose formulation" and "fixed dose combination" are used interchangeably. Common single dose formulations include pills, tablets, or capsules.

As used herein "subject" and "patient" are used interchangeably. A subject is a mammal and the mammal may be, for example, a human, and human subjects include adult, adolescent and pediatric subjects.

"Steatosis" and "hepatic steatosis" are used interchangeably herein.

"Blood plasma" and "plasma" are used interchangeably herein.

The following table provides dose categories as used herein for a number of statins.

TABLE 1

| Low to Moderate Dose | High Dose |
|---|---|
| Atorvastatin 10-40 mg | Atorvastatin 80 |
| Fluvastatin 20-40 mg | Lovastatin 80 |
| Lovastatin 20-60 mg | Rosuvastatin 40 |
| Pitavastatin 1-4 mg | Simvastatin 80 |
| Pravastatin 10-40 mg | |
| Rosuvastatin 5-30 | |
| Simvastatin 5-60 mg | |

The present invention provides for methods for the treatment of subjects having type IIb hyperlipidemia. As described in further detail in Example 3, an 8-week, double-blind, randomized, placebo-controlled, dose-ranging study was done to evaluate the efficacy and safety of gemcabene administered as monotherapy or in combination with atorvastatin in the treatment of hypercholesterolemic patients. The primary objective was to evaluate the low-density lipoprotein cholesterol (LDL-C) lowering efficacy and dose response of gemcabene 300, 600, and 900 mg/day administered as a monotherapy or in combination with atorvastatin 10, 40, and 80 mg/day to hypercholesterolemia patients (Frederickson Types IIa and IIb). The secondary objective was to evaluate the modulation of high sensitivity c-reactive protein (hsCRP), high-density lipoprotein cholesterol (HDL), and triglycerides (TG), and apolipoprotein B (ApoB) by gemcabene.

Subjects were randomized to receive placebo, the agents as monotherapy, or the agents combined at various dose levels for 8 weeks. Before and at the end of the treatment period, safety and lipid variable were assessed including plasma triglyceride, LDL-C and apo B levels.

Subgroup analysis of LDL-C and TG in subjects with an LDL-C level ≥130 mg/dl and a triglyceride level ≥150 mg/dL. (Type IIb) revealed an unexpected reduction in triglycerides in patients given less than the maximum dose (80 mg) of atorvastatin plus gemcabene (300, 600, or 900 mg). At the other doses of atorvastatin tested, the reduction in triglycerides with combination therapy was much great than either the reduction with atorvastatin or gemcabene monotherapy. In addition, these combinations also caused further reductions in LDL-C and apo B over administration of atorvastatin or gemcabene alone.

The finding that using a low to moderate dose of a statin in combination with gemcabene resulted in the surprising lowering of TG in this group of subjects potentially provides for a safety advantage.

Cytochrome P450 enzymes mediate drug metabolism in humans. For example some statins and fibrates use or activate the cytochrome P450 3A4 isoform as part of their catabolic process. When given together, some statins and fibrates compete for the cytochrome P450 3A4 isoform resulting in a drug-drug interaction affecting the levels of each agent in blood plasma.

As an example, the statin marketed as Baycol was removed from the market following a severe drug-drug interaction (DDI) with gemfibrozil (a fibrate) resulting in rhabdomyolysis and patient deaths.

As described further in Example 1 below, no evidence of significant inhibition was observed for any of the cytochrome P450 isoforms tested up to a concentration of 1500 μM. suggesting that a metabolically based clinical interaction between gemcabene and statins are highly unlikely at therapeutic concentrations of gemcabene.

In addition, gemcabene monotherapy given to humans up to 1500 mg single dose and 900 mg in multiple doses, the number of musculoskeletal adverse event were similar or less than placebo, while statin monotherapy showed an increase in musculoskeletal adverse events compared to placebo. As shown in Table 2, co-administration of gemcabene and the statin did not increase the musculoskeletal adverse effects seen with the statin alone.

TABLE 2

| Patient type | Control | | | Gemcabene | | | Gemcabene + Statin | | | Statin | | |
|---|---|---|---|---|---|---|---|---|---|---|---|---|
| | n | No | % | n | No | % | n | No | % | n | No | % |
| A4141001 (IIa + IIb) | 17 | 1 | 5.9 | 51 | 0 | 0.0 | 157 | 13 | 8.3 | 52 | 7 | 13.5 |
| A4141001 (IIa) | 10 | 0 | 0.0 | 19 | 0 | 0.0 | 79 | 5 | 6.3 | 22 | 2 | 9.1 |
| A4141001 (IIb) | 7 | 1 | 14.3 | 32 | 0 | 0.0 | 78 | 8 | 10.3 | 30 | 5 | 16.7 |

"n" = number of patients in the group.
No = the number of muscle skeletal adverse events and
% = the percent of patients experiencing a musculoskeletal adverse event in the particular group.

Embodiments

The first aspect of the invention provides methods for treating a subject having type IIb hyperlipidemia comprising administering to the subject gemcabene in combination with a low or moderate dose of a statin. In some embodiments of the invention the gemcabene and the statin are administered as a fixed dose combination. A third aspect of the invention provides specific fixed dose combinations of gemcabene and a statin. A fourth aspect provides for kits for treating a subject having type IIb hyperlipidemia and/or NASH. A fifth aspect of the present invention provides a method for reducing fibrosis in a patient comprising administering gemcabene alone or in combination with a statin.

Gemcabene is generally administered as the monocalcium salt (gemcabene calcium).

One embodiment of the first aspect is a method for treating a subject having type IIb hyperlipidemia comprising, administering to the subject gemcabene in combination with a low or moderate intensity dose of a statin.

Another embodiment is a method of treating a subject having type IIb hyperlipidemia comprising administering to the subject a daily dose gemcabene from about 50 mg to about 750 mg and a daily dose of a statin from about 1 mg to about 60 mg.

Yet another embodiment is a method of treating a subject having type IIb hyperlipidemia comprising administering to the subject a daily dose of gemcabene from about 50 mg to about 900 mg and a daily dose of a statin wherein the statin is atorvastatin, rosuvastatin, simvastatin, pravastatin, lovastatin, fluvastatin, or pitavastatin. Another embodiment is a method of treating a subject having type IIb hyperlipidemia comprising administering to the subject a daily dose gemcabene from about 150 mg to about 600 mg and a daily dose of a statin wherein the statin is atorvastatin, rosuvastatin, simvastatin, pravastatin, lovastatin, fluvastatin Still another embodiment is a method of treating a subject having type IIb hyperlipidemia comprising administering to the subject a daily dose gemcabene from about 150 mg to about 450 mg and a daily dose of a statin wherein the statin is atorvastatin, rosuvastatin, simvastatin, pravastatin, lovastatin, fluvastatin.

Still another embodiment is a method of treating a subject having type IIb hyperlipidemia comprising administering to the subject, a daily dose of gemcabene.

Still another embodiment is a method of treating a subject having type IIb hyperlipidemia comprising administering to the subject, a daily dose of gemcabene from about 50 mg to about 600 mg, or about 150 mg to about 600, or from about 150 mg to about 450 mg, or from about 150 mg to about 300 mg and a daily dose of a statin wherein the statin is atorvastatin, rosuvastatin, simvastatin, pravastatin, lovastatin, fluvastatin, or pitavastatin and:

a. the statin is atorvastatin and daily dose of atorvastatin is from about 10 mg to about 60 mg or about 5 mg to about 60 mg;
b. the statin in rosuvastatin and the daily dose of rosuvastatin is from about 5 mg to about 20 mg or from about 2.5 mg to about 30 mg;
c. the statin is simvastatin and the daily dose of simvastatin is from about 10 mg to about 40 mg or from about 5 mg to about 60;
d. the statin is pravastatin and the daily dose of pravastatin is from about 10 mg to about 80 mg or from about 5 mg to about 60 mg;
e. the statin is lovastatin and the daily dose of lovastatin is from about 20 mg to about 40 mg or from about 10 mg to about 60 mg;
f. the statin is fluvastatin and the daily dose of fluvastatin is from about 20 mg to about 80 mg or from about 1 mg to about 60 mg; or
g. the statin is pitavastatin and the daily dose of pitavastatin is from about 1 mg to about 4 mg.

In any of the above embodiments the daily dose of gemcabene is from about 50 mg to about 600 mg. In some of the above embodiments the daily dose gemcabene is 50 mg, 75 mg, 100 mg, 150 mg, 300 mg, 400 mg, 450 mg, 500 mg, or 600 mg.

In some of the embodiments of the method of treating a subject having type IIb hyperlipidemia, the daily dose of atorvastatin is from about 10 mg to about 40 mg.

In some of the embodiments of the method of treating a subject having type IIb hyperlipidemia, the daily dose of rosuvastatin is from about 10 to about 20 mg.

In some of the embodiments of the method of treating a subject having type IIb hyperlipidemia, the daily dose of simvastatin is from about 10 mg to about 20 mg.

In some of the embodiments of the method of treating a subject having type IIb hyperlipidemia, the daily dose of pravastatin is from about 10 mg to about 40 mg.

In some of the embodiments of the method of treating a subject having type IIb hyperlipidemia, the daily dose of lovastatin is about 40 mg.

In some of the embodiments of the method of treating a subject having type IIb hyperlipidemia, the daily dose of fluvastatin is about 20 mg to about 40 mg.

In some of the embodiments of the method of treating a subject having type IIb hyperlipidemia, the daily dose of pitavastatin is from about 1 mg to about 3 mg.

In any of the embodiments of the method of treating a subject having type IIb hyperlipidemia, the statin and gemcabene may be administered as a fixed dose combination.

The some embodiments of the present invention the subject has familial combined hyperlipidemia (FCHL).

In some embodiments of the methods of treating a subject having type IIb hyperlipidemia, the subject's plasma triglyceride level is reduced to below 150 mg/dl within 8 weeks of administration of gemcabene and the statin.

In other embodiments of the methods of treating a subject having type IIb hyperlipidemia, the subject's plasma LDL cholesterol level is reduced to below 130 mg/dl within 8 weeks of administration of gemcabene and the statin.

In still other embodiments of the methods of treating a subject having type IIb hyperlipidemia, the subject's plasma triglyceride level is reduced to below 150 mg/dl and the subjects LDL cholesterol level is reduced to below 130 mg/dl within 8 weeks of administration of gemcabene and the statin.

In some embodiments of the method of treating a subject having type IIb hyperlipidemia, the subject's HDL cholesterol level is increased after treatment.

In some embodiment of the method of treating a subject having type IIb hyperlipidemia, the subject's risk of myopathy is reduced from the risk of administration of a high dose of a statin alone.

In some embodiments of the method of treating a subject having type IIb hyperlipidemia, the subject's risk of myositis is reduced from the risk of administration of a high dose of statin alone.

In some embodiments of the method of treating a subject having type IIb hyperlipidemia, the subject's risk of rhabdomyolysis is reduced from the risk of administration of a high dose of statin alone.

In any of the embodiments of the methods of the invention the subject may be administered an additional cholesterol lowering agent. In some embodiments the additional cholesterol lowering agent is a cholesterol absorption inhibitor. In some embodiments the cholesterol absorption inhibitor is ezetimibe. In some embodiments the cholesterol lowering agent is a PCKS9 inhibitor.

In some embodiments of the method of treating a subject having type IIb hyperlipidemia, the subject's risk of having a primary cardiovascular event is reduced.

In some embodiments of the method of treating a subject having type IIb hyperlipidemia, the subject's risk of having a secondary cardiovascular event is reduced. Another embodiment is a method for treating a patient having type IIb hyperlipidemia comprises administering to a subject a daily dose of gemcabene of about 150 mg and a daily dose of atorvastatin selected from the group consisting of 10 mg, 20 mg, 30 mg, 40 mg, 50 mg or 60 mg.

Yet another embodiment is a method for treating a patient having type IIb hyperlipidemia comprising administering to a subject a daily dose of gemcabene of about 300 mg and a daily dose of atorvastatin selected from the group consisting of 10 mg, 20 mg, 30 mg, 40 mg, 50 mg or 60 mg.

Still another embodiment is a method for treating a patient having type IIb hyperlipidemia comprising administering to a subject a daily dose of gemcabene of about 450 mg and a daily dose of atorvastatin selected from the group consisting of 10 mg, 20 mg, 30 mg, 40 mg, 50 mg or 60 mg.

Another embodiment is a method for treating a patient having type IIb hyperlipidemia comprising administering to a subject a daily dose of gemcabene of about 600 mg and a daily dose of atorvastatin selected from the group consisting of 10 mg, 20 mg, 30 mg, 40 mg, 50 mg or 60 mg.

A second aspect of the present invention provides a method for reducing the amount of liver fat or the accumulation of liver fat in the subject comprising administering gemcabene alone or in combination with a statin. In some embodiments of the second aspect, the method is a method of treating a subject to reduce or prevent steatosis comprising administering gemcabene alone or in combination with a statin. One embodiment of the second aspect is a method of treating fatty liver disease in the subject comprising administering gemcabene alone or in combination with a statin. Another embodiment is a method of treating a liver disease where in the liver disease is non-alcoholic fatty liver disease (NAFLD). In some embodiments of the second aspect, the method is a method of treating a subject to prevent or reduce the rate of progression of liver disease. In some embodiments the liver disease is non-alcoholic hepatic steatosis (NASH). In some embodiments the liver disease is alcoholic hepatic steatosis. In some embodiments of the second aspect of the invention, the subject has type IIb hyperlipidemia. In some embodiments the patient has FCHL. In any of the embodiments of the second aspect, the subject may have a risk factor for developing fatty liver (steatosis) wherein the risk factor is that the subject has metabolic syndrome, type-2 diabetes, impaired glucose tolerance, obesity, dyslipidemia, hepatitis B, hepatitis C, an HIV infection, or a metabolic disorder such as Wilson's disease, a glycogen storage disorder, or galactosemia. In some embodiments the patient has diabetes. In some embodiments the patient has an inflammatory condition. In some embodiments the patient has an elevated body mass index above what is normal for gender, age and height.

In some embodiments of the second aspect, the method is a method for reducing the accumulation of liver fat in a patient by administering gemcabene as a monotherapy to the patient. In some embodiments the gemcabene is administered with one or more additional therapeutic agents. In some embodiments the one or more additional therapeutic agent is a statin. In some embodiments the statin is atorvastatin, rosuvastatin, simvastatin, pravastatin, lovastatin, fluvastatin, or pitavastatin.

In any of the embodiments of the second aspect the method of preventing or reducing the accumulation of liver fat in a subject comprises administering to a subject in need thereof gemcabene in a daily dose of about 50 mg to about 900 mg Another embodiment of the second aspect is a method of preventing or reducing the accumulation of liver fat in a subject comprising administering to a subject in need thereof gemcabene in a daily dose of about 50 mg to about 900 mg in combination with a statin in a daily dose from about 1 mg to about 80 mg.

Another embodiment of the second aspect is a method of reducing the accumulation of liver fat in a subject comprising administering to a subject in need thereof gemcabene in combination with a statin, wherein the daily dose of gemcabene administered to the subject is from about 50 mg to about 900 mg per day and the statin is atorvastatin, rosuvastatin, simvastatin, pravastatin, lovastatin, fluvastatin, or pitavastatin.

In any of the embodiments of the methods of preventing or reducing the accumulation of liver fat in a subject, the daily dose gemcabene is from about 50 mg to about 900 mg.

In any embodiments of the methods of reducing the accumulation of liver fat in a subject, the daily dose of gemcabene is 150 mg, 300 mg, 450 mg, or 600 mg.

In any of the embodiments of the methods for reducing the accumulation of liver fat in a subject, the daily dose of atorvastatin is from about 10 mg to about 80 mg.

In any embodiments of the methods for reducing the accumulation of liver fat in a subject, the daily dose of rosuvastatin is from about 5 to about 40 mg.

In any embodiments of the methods for reducing the accumulation of liver fat, simvastatin is from about 10 mg to about 20 mg.

In any embodiments of the methods for reducing the accumulation of liver fat, the daily dose of pravastatin is from about 10 mg to about 40 mg.

In any embodiments of the methods for reducing the accumulation of liver fat, the daily dose of lovastatin is from about 20 to about 40 mg.

In any embodiments of the methods for reducing the accumulation of liver fat, the daily dose of fluvastatin is from about 20 mg to about 40 mg.

In any embodiments of the methods for reducing the accumulation of liver fat, the daily dose of pitavastatin is from about 1 mg to about 3 mg.

In any embodiments of the methods for reducing the accumulation of liver fat the statin and gemcabene may be administered as a fixed dose combination.

In some embodiments of the methods for reducing the accumulation of liver fat the subject's risk of developing a liver disease is reduced.

In some embodiments the methods for reducing the accumulation of liver fat, the subject has liver disease.

In some embodiments of the methods for reducing the accumulation of liver fat, the fat is triglyceride.

In some embodiments, the liver disease is nonalcoholic steatohepatitis (NASH).

In some embodiments, the liver disease is nonalcoholic fatty liver disease (NAFLD).

In some embodiments, the liver disease is liver fibrosis.

In some embodiments, the liver disease is inflammation of the liver.

In some embodiments, the liver disease is cirrhosis of the liver.

In one embodiment of the second aspect of the invention the subject is administered a daily dose of gemcabene of about 75 mg and a daily dose of a statin at a daily dose of from 1 to 80 mg.

In a particular embodiment of the second aspect the subject is administered a daily dose of gemcabene of about 150 mg and a daily dose of atorvastatin selected from the group consisting of 10 mg, 20 mg, 30 mg, 40 mg, 50 mg, 60 mg or 80.

In another particular embodiment of the second aspect the subject is administered a daily dose of gemcabene of about 300 mg and a daily dose of atorvastatin selected from the group consisting of 10 mg, 20 mg, 30 mg, 40 mg, 50 mg or 60 mg.

In a particular embodiment of the second aspect the subject is administered a daily dose of gemcabene of about 450 mg and a daily dose of atorvastatin selected from the group consisting of 10 mg, 20 mg, 30 mg, 40 mg, 50 mg or 60 mg.

In another particular embodiment of the second aspect the subject is administered a daily dose of gemcabene of about 600 mg and a daily dose of atorvastatin selected from the group consisting of 10 mg, 20 mg, 30 mg, 40 mg, 50 mg or 60 mg.

In another particular embodiment of the second aspect the subject is administered a daily dose of gemcabene of about 900 mg and a daily dose of atorvastatin selected from the group consisting of 10 mg, 20 mg, 30 mg, 40 mg, 50 mg or 60 mg.

In a preferred embodiment of the second aspect of the invention the subject is administered a daily dose of gemcabene of about 450 mg and a daily dose of atorvastatin selected of 10 mg. In another preferred embodiment the subject is administered a daily dose of gemcabene of about 450 mg and a daily dose of atorvastatin selected of 20 mg. In another preferred embodiment the subject is administered a daily dose of gemcabene of about 450 mg and a daily dose of atorvastatin selected of 40 mg.

In a preferred embodiment of the second aspect of the invention the subject is administered a daily dose of gemcabene of about 300 mg and a daily dose of atorvastatin selected of 10 mg. In another preferred embodiment the subject is administered a daily dose of gemcabene of about 300 mg and a daily dose of atorvastatin selected of 20 mg. In another preferred embodiment the subject is administered a daily dose of gemcabene of about 300 mg and a daily dose of atorvastatin selected of 40 mg.

In a preferred embodiment of the second aspect of the invention the subject is administered a daily dose of gemcabene of about 150 mg and a daily dose of atorvastatin selected of 10 mg. In another preferred embodiment the subject is administered a daily dose of gemcabene of about 150 mg and a daily dose of atorvastatin selected of 20 mg. In another preferred embodiment the subject is administered a daily dose of gemcabene of about 150 mg and a daily dose of atorvastatin selected of 40 mg.

In some embodiments of the second aspect the method further comprises administering an additional therapeutic agent and the additional agent is a drug for treating NASH. In some embodiments the additional agent is simtuzumab, GS-4997, GS-974, GS-0976, INT-47 obeticholic acid, or cenicriviroc.

In embodiment A of the second aspect, the invention includes a method for treating or preventing steatosis, NAFLD, or NASH, comprising administering to a subject in need thereof an effective amount of a compound of Formula (I):

$$Y^1\underset{(CH_2)_m}{\overset{R^1}{\diagdown}}\underset{(CH_2)_n}{\overset{R^2}{\diagup}}X\underset{(CH_2)_n}{\overset{R^{11}}{\diagdown}}\underset{(CH_2)_m}{\overset{R^{12}}{\diagup}}Y^2, \quad (I)$$

or a pharmaceutically acceptable salt, or hydrate wherein:
(a) each occurrence of m is independently an integer ranging from 0 to 5;
(b) each occurrence of n is independently an integer ranging from 3 to 7;
(c) X is —(CH$_2$)$_z$—, —O—, —CH(OH)—, CH(CH$_2$OH)—, —NH— or —S—, wherein z is an integer from 0 to 4;

(d) each occurrence of $R^1$ and $R^2$ is independently $(C_1-C_6)$alkyl, $(C_2-C_6)$alkenyl, $(C_2-C_6)$alkynyl, phenyl, benzyl, or $R^1$ and $R^2$ and the carbon to which they are both attached are taken together to form a $(C_3-C_7)$cycloakyl group;

(e) each occurrence of $R^{11}$ and $R^{12}$ and the carbon to which they are both attached are taken together to form a $(C_3-C_7)$cycloakyl group;

(f) each occurrence of $Y^1$ and $Y^2$ is independently $(C_1-C_6)$alkyl, OH, COOH, COOR$^3$, SO$_3$H,

[chemical structures]

wherein:
(i) $R^3$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups,
(ii) each occurrence of $R^4$ is independently H, $(C_1-C_6)$alkyl, $(C_2-C_6)$alkenyl, $(C_2-C_6)$alkynyl and is unsubstituted or substituted with one or two halo, OH, $C_1-C_6$ alkoxy, or phenyl groups; and
(iii) each occurrence of $R^5$ is independently H, $(C_1-C_6)$alkyl, $(C_2-C_6)$alkenyl, $(C_2-C_6)$alkynyl.

In an exemplary compound of formula (I), each occurrence of Y is independently OH, COOR$^3$, or COOH.

Other compounds of formula (I) are those wherein m is 0.
Other compounds of formula (I) are those wherein m is 1.
Other compounds of formula (I) are those wherein n is 4.
Other compounds of formula (I) I are those wherein n is 5.
Other compounds of formula (I) are those wherein z is 0.
Other compounds of formula (I) are those wherein z is 1.
Other compounds of formula (I) are those wherein $Y^1$ and $Y^2$ are each independently $(C_1-C_6)$alkyl.
Other compounds of formula (I) are those wherein $Y^1$ and $Y^2$ are each methyl.
Other compounds of formula (I) are those wherein each occurrence $R^1$ and $R^2$ and the carbon to which they are both attached are taken together to form a $(C^3-C^7)$ cycloakyl group.

Embodiment B of the second aspect of the invention is a method treating or preventing steatosis, NAFLD, or NASH, comprising administering to a subject in need thereof an effective amount of a compound of Formula (II):

(II)

$$Y^1 \underset{O}{\overset{R^1 \; R^2}{\underset{|}{\text{C}}}}(CH_2)_n\text{—X—}(CH_2)_n\underset{O}{\overset{R^{11} \; R^{12}}{\underset{|}{\text{C}}}}Y^2,$$

or a pharmaceutically acceptable salt, or hydrate, wherein:
(a) each occurrence of m is independently an integer ranging from 0 to 5;
(b) each occurrence of n is independently an integer ranging from 3 to 7;
(c) X is —(CH$_2$)$_z$—, —O—, —CH(OH)—, CH(CH$_2$OH)—, —NH— or —S—, wherein z is an integer from 0 to 4;
(d) each occurrence of $R^1$ and $R^2$ is independently $(C_1-C_6)$alkyl, $(C_2-C_6)$alkenyl, $(C_2-C_6)$alkynyl, phenyl, benzyl, or $R^1$ and $R^2$ and the carbon to which they are both attached are taken together to form a $(C_3-C_7)$cycloakyl group;
(e) each occurrence of $R^{11}$ and $R^{12}$ and the carbon to which they are both attached are taken together to form a $(C_3-C_7)$cycloakyl group;

(f) each occurrence of $Y^1$ and $Y^2$ is independently $(C_1$-$C_6)$alkyl, OH, COOH, COOR$^3$, SO$_3$H,

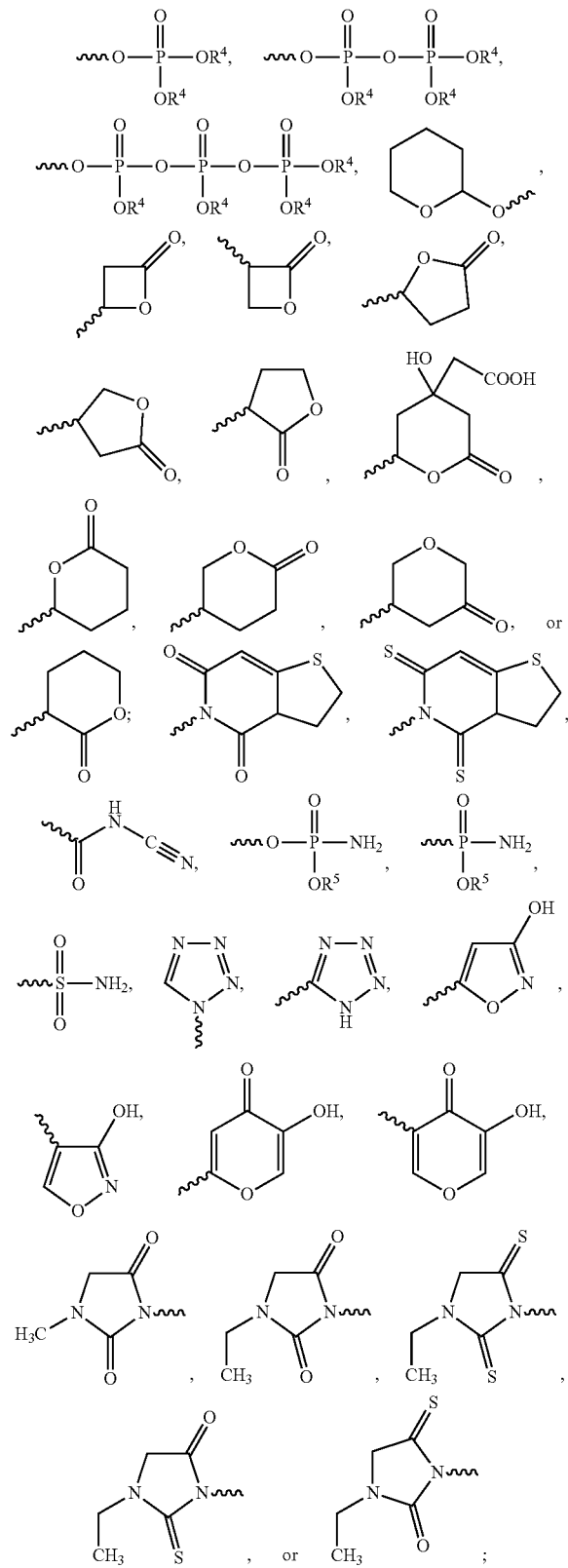

wherein:
(i) $R^3$ is $(C_1$-$C_6)$alkyl, $(C_2$-$C_6)$alkenyl, $(C_2$-$C_6)$alkynyl, phenyl, or benzyl and is unsubstituted or substituted with one or more halo, OH, $(C_1$-$C_6)$alkoxy, or phenyl groups,
(ii) each occurrence of $R^4$ is independently H, $(C_1$-$C_6)$ alkyl, $(C_2$-$C_6)$alkenyl, $(C_2$-$C_6)$alkynyl and is unsubstituted or substituted with one or two halo, OH, $C_1$-$C_6$ alkoxy, or phenyl groups; and
(iii) each occurrence of $R^5$ is independently H, $(C_1$-$C_6)$ alkyl, $(C_2$-$C_6)$alkenyl, $(C_2$-$C_6)$alkynyl.

In an exemplary compound of formula (II), each occurrence of Y is independently OH, COOR$^3$, or COOH.

Other compounds of formula (II) are those wherein n is 4.
Other compounds of formula (II) are those wherein n is 5.
Other compounds of formula (II) are those wherein z is 0.
Other compounds of formula (II) are those wherein z is 1.
Other compounds of formula (II) are those wherein $Y^1$ and $Y^2$ are each independently $(C_1$-$C_6)$alkyl.
Other compounds of formula (II) are those wherein $Y^1$ and $Y^2$ are each methyl.
Other compounds of formula (II) are those wherein each occurrence $R^1$ and $R^2$ and the carbon to which they are both attached are taken together to form a $(C^3$-$C^7)$cycloakyl group.

In one embodiment according to embodiment B, the compounds is bempedoic acid.

In one embodiment according to embodiment B, the compound has the structure:

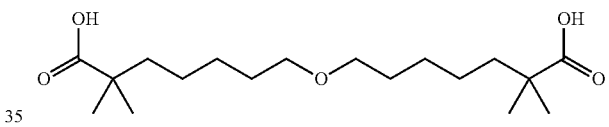

or a pharmaceutically acceptable salt or hydrate thereof.

In another embodiment according to embodiment B, the compound is gemcabene or a pharmaceutically acceptable salt thereof.

In another embodiment according to embodiment B, the compound is the monocalcium salt of gemcabene.

In yet another embodiment according to embodiment B, the compound is a hydrate of the monocalcium salt of gemcabene.

In another embodiment according to embodiment B, the compound or pharmaceutically acceptable salt thereof is present in a composition that further comprises a pharmaceutically acceptable vehicle or carrier.

In a further embodiment according to embodiment B, the composition is formulated for oral administration.

In still a further embodiment according to embodiment B, the composition is in the form of a tablet or capsule.

In one embodiment according to embodiment B, the compound or pharmaceutically acceptable salt thereof is present in the composition in an amount of about 50 mg to about 900 mg.

In one embodiment according to embodiment B, the compound or pharmaceutically acceptable salt thereof is present in the composition in an amount of about 1 mg to about 1,000 mg.

A third aspect of the present invention is a fixed dose combination of gemcabene and a statin.

Fixed dose combinations of a statin plus gemcabene are useful for the prevention and treatment of subjects having one or more of type IIb hyperlipidemia, high liver fat, NAFLD, or NASH, and complications associated with these conditions as well as other conditions requiring the lowering of LDL-C and/or triglyceride levels. By using a fixed dose combination the rate of release of each component of the dose can be controlled. In that statins, especially high dose statins, can lead to complication related to safety, the regulated and slow release of a statin benefits and can mitigate the risk of skeletal muscle safety associated with higher doses of statins. Fixed dose combinations also are convenient to take and reduce the risk of incorrectly dosing when taking multiple medications and may increase compliance.

Fixed dose combinations of the present disclosure comprise a pharmaceutical composition comprising gemcabene and a statin in specific amounts. The fixed dose combinations of the present invention provide the same dosages of the APIs as administered separately as described herein.

One embodiment of the third aspect of the present invention is a fixed dose combination comprising an amount of gemcabene from about 50 mg to about 750 mg and an amount of a statin from about 1 mg to about 60 mg.

In one embodiment the fixed dose combination wherein the amount of gemcabene is from about 150 mg to about 600 mg and the statin is atorvastatin, rosuvastatin, simvastatin, pravastatin, lovastatin, fluvastatin, or pitavastatin wherein:

a. the amount of atorvastatin is from about 10 mg to about 60 mg;
b. the amount of rosuvastatin is from about 5 mg to about 20 mg;
c. the amount of simvastatin is from about 10 mg to about 40 mg;
d. the amount of pravastatin is from about 10 mg to about 80 mg;
e. the amount of lovastatin is from about 20 mg to about 40 mg;
f. the amount of fluvastatin is from about 20 mg to about 80 mg; or
g. the amount of pitavastatin is from about 1 mg to about 4 mg.

In some embodiments of the third aspect of the invention amount of gemcabene is from about 300 mg to about 600 mg.

In some embodiments the amount of gemcabene is 300 mg or 600 mg.

In some embodiments the amount of atorvastatin is from about 10 mg to about 40 mg.

In other embodiments the amount of rosuvastatin is from about 10 to about 20 mg.

In still other embodiments the amount of simvastatin is from about 10 mg to about 20 mg.

In some embodiments the amount of pravastatin is from about 10 mg to about 20 mg.

In other embodiments the amount of lovastatin is about 40 mg.

In other embodiments the amount of fluvastatin is from about 20 mg to about 40 mg.

In other embodiments the amount of pitavastatin is from about 1 mg to about 3 mg.

In some embodiments the fixed dose combination comprises 300 mg gemcabene and 10 mg of atorvastatin. In some embodiments the fixed dose combination comprises 300 mg gemcabene and 20 mg of atorvastatin. In some embodiments the fixed dose combination comprises 300 mg gemcabene and 40 mg of atorvastatin.

In some embodiments the fixed dose combination comprises 600 mg gemcabene and 10 mg of atorvastatin. In some embodiments the fixed dose combination comprises 600 mg gemcabene and 20 mg of atorvastatin. In some embodiments the fixed dose combination comprises 600 mg gemcabene and 40 mg of atorvastatin.

In some embodiments the fixed dose combination comprises 900 mg gemcabene and 10 mg of atorvastatin. In some embodiments the fixed dose combination comprises 900 mg gemcabene and 20 mg of atorvastatin. In some embodiments the fixed dose combination comprises 900 mg gemcabene and 40 mg of atorvastatin. In some embodiments, the fixed dose combination is in the form of a tablet.

Formulations.

Compounds useful in the present invention can be formulated as pharmaceutical compositions and administered to a subject, such as a human subject in a variety of forms adapted to the chosen route of administration, i.e., orally, transdermal, and parenterally. Such compositions and methods for their preparation are well known and may be found, for example, in Remington's Pharmaceutical Sciences, 19th Edition (Mack Publishing Company, 1995). For example, typical formulations for gemcabene are described in U.S. Pat. No. 5,648,387. In one embodiment, gemcabene is formulated alone or in combination with a statin with common excipients and carriers such as starch, binders, diluents and the like, and molded into tablets, or encapsulated into gelatin capsules for convenient oral administration.

A fourth aspect of the present invention provides a kit comprising fixed dose combination comprising from about 1 mg to about 60 mg of a statin and from about 150 mg to about 900 mg of gemcabene; and instructions for the use thereof. In some embodiments, the statin is selected from atorvastatin, rosuvastatin, simvastatin, pravastatin, lovastatin, fluvastatin, and pitavastatin; or any pharmaceutically acceptable salts thereof. In some embodiments, the statin is atorvastatin.

A fifth aspect of the present invention provides methods for reducing fibrosis in a patient comprising administering gemcabene alone or in combination with a statin. One embodiment of the fifth aspect is a method of reducing hepatic fibrosis in a subject in need thereof, comprising administering to the subject gemcabene. Another embodiment of the fifth aspect is a method of reducing hepatic fibrosis in a subject in need thereof, comprising administering to the subject gemcabene wherein the subject has NASH. In some embodiments of the fifth aspect the daily dose of the gemcabene administered is from about 50 mg to about 900 mg. In another embodiment the daily dose gemcabene is of from about 150 mg to about 600 mg. In still another embodiment the daily dose gemcabene is 150 mg, 300 mg, 450, or 600 mg. Another embodiment of the fifth aspect is method of reducing hepatic fibrosis in a subject in need thereof, comprising administering to the subject gemcabene in combination with a statin. In various embodiments the statin is atorvastatin, rosuvastatin, simvastatin, pravastatin, lovastatin, fluvastatin, or pitavastatin.

A sixth aspect of the present invention provides method for reducing plasma fibrinogen levels in a subject, comprising administering to the subject gemcabene. One embodiment of the sixth aspect of the invention is a method for reducing blood plasma fibrinogen levels in a subject in need thereof, wherein the subject's fibrinogen level is greater than 300 mg/dL comprising administering gemcabene to the subject. In another embodiment of the sixth aspect of the invention is a method for reducing blood plasma fibrinogen levels in a subject in need thereof, wherein the subject's fibrinogen level is greater than 400 mg/dL comprising administering gemcabene to the subject. In some embodiments of the sixth aspect the method comprises administering to the subject a dose of gemcabene from 50 mg to 900 mg. In some embodiments gemcabene is administered at a dose of from 150 to 600 mg. In some embodiments the dose of gemcabene is 50, 75, 150, 300, 450, 600 or 900 mg. An embodiment of the sixth aspect is a method of reducing blood plasma fibrinogen levels in a subject in need thereof, comprising administering to the subject gemcabene in combination with a statin. Another embodiment is a method of reducing a subject's plasma fibrinogen level comprising administering gemcabene in combination with a statin where the statin is atorvastatin, rosuvastatin, simvastatin, pravastatin, lovastatin, fluvastatin, or pitavastatin. Another embodiment of the sixth aspect is a method of reducing plasma fibrinogen levels in a subject in need thereof, comprising administering to the subject gemcabene at a daily dose of from 50 mg to 900 mg and a statin at a daily dose from 1 mg to 80 mg. Yet another embodiment is a method of reducing plasma fibrinogen levels in a subject in need thereof, comprising administering to the subject gemcabene at a daily dose of 300 mg, 600 mg or 900 mg and atorvastatin at a daily dose of 10 mg, 40 mg, or 80 mg. In still another embodiment is a method of reducing plasma fibrinogen levels in a subject in need thereof, comprising administering to the subject gemcabene at a daily dose of 600 mg and atorvastatin at a daily dose of 10 mg.

In some of the embodiments of the sixth aspect the subject has a reduction in the subject's risk for a primary cardiovascular event. In other embodiments of the sixth aspect the subject has a reduction in the subject's risk for a secondary cardiovascular event. In any of the embodiments of the sixth aspect, the subject may be administered an additional therapeutic agent. In some embodiments the additional therapeutic agent is an anti-coagulation agent or a lipid regulating agent. In some embodiments the anti-coagulation agent is aspirin, dabigatran, rivaroxaban, apixaban clopidogrel, thienopyridine, warfarin (Coumadin) acenocoumarol, phenprocoumon, atromentin, phenindione, edoxaban betrixaban, letaxaban eribaxaban hirudin, lepirudin, bivalirudin, argatroban, dabigatran. ximelagatran, batroxobin, hementin, heparin(s) and vitamin E. In another embodiment of the sixth aspect is a method of reducing plasma fibrinogen levels in a subject in need thereof, comprising administering to the subject gemcabene at a daily dose of from 50 mg to 900 mg and a statin at a daily dose from 1 mg to 80 mg to prophylactically reduce or treat coagulation complications in subject's having diabetes, impaired glucose tolerance, metabolic syndrome, obesity, cancer, sepsis, sleep apnea, atrial fibrillation, deep vein thrombosis, stroke, hypercoaguable states, myocardial infarction, pulmonary embolism, restenosis, hypertriglyceridemia, hypertension, NAFLD, NASH or cardiovascular diseases.

Another embodiment of the sixth aspect, is the method of reducing plasma fibrinogen in a subject in need thereof, to reduce blood clotting, comprising administering to the subject gemcabene in a daily dose from 50 mg to 900 mg. Another embodiment of the sixth aspect, is the method of reducing plasma fibrinogen in a subject in need thereof, to prophylactically reduce blood clotting, comprising administering to the subject gemcabene in a daily dose from 50 mg to 900 mg. In some embodiments gemcabene is administered in combination with a statin. In some embodiments the statin is atorvastatin, rosuvastatin, simvastatin, pravastatin, lovastatin, fluvastatin, or pitavastatin and the daily dose of the statin is from 1 mg to 80 mg. One embodiment of the sixth aspect, is the method of reducing plasma fibrinogen in a subject in need thereof, comprising administering to the subject gemcabene in a daily dose from 50 mg to 900 mg to treat peripheral vascular disease, peripheral artery disease, microvascular disease, peripheral arterial occlusive disease or critical limb ischemia.

EXAMPLES

Example 1

Cytochrome P450 Enzymes Mediate Drug and Xenobiotic Metabolism in Humans.

For example some statins and fibrates use or activate the cytochrome P450 3A4 isoform as part of their catabolic process. When given together, statins and fibrates compete for the cytochrome P450 3A4 isoform resulting in a drug-drug interaction affecting the levels of each agent in blood plasma.

In order to investigate whether or not gemcabene might have similar drug-drug interactions, the ability of gemcabene at 100, 300, and 1500 mM to inhibit seven major cytochrome P450 enzymes, CYP1A2, CYP2A6, CYP2C9, CYP2C19, CYP2D6, CYP2E1, and CYP3A4, which mediate drug and xenobiotic metabolism in humans, was investigated using isoform selective marker substrates and human liver microsomal preparations.

A series of probe substrates was used to assess the inhibitory activity of gemcabene on a cytochrome P450 dependent, isoform selective metabolic pathway of the probe substrate. Human livers, HLM141, HLM143, and HLM144 were selected from the University of Washington Human Liver Bank for this study. Microsomes were prepared, and the ability of gemcabene (100, 300, and 1500 mM or 30.2, 90.7, and 453.6 mg/mL) to inhibit the defining metabolic pathway of each of the probe substrates at its Km was determined. The only exception was CYP1A2 where the concentration used, 0.5 mM, was below the Km, about 1.5 mM. The actual concentrations used for each of the other probes are specified below. The experimental control consisted of a complete microsomal incubation with the probe substrate in the absence of gemcabene. Determinations were done in triplicate for the control and for each of the different gemcabene concentrations. The concentrations of gemcabene chosen for the initial investigation were designed to insure that the microsomal concentrations would encompass a range that would equal and significantly exceed concentrations of gemcabene that would be expected to be encountered in vivo. The seven isoforms and the metabolic pathway of each of the probes used to monitor specific isoform activity are listed below.

CYP1A2: The 6-hydroxylation of high concentrations (0.5 mM) of (R)-warfarin. The reaction is monitored by quantitative gas chromatographic/mass spectrometric (GC/MS) using 6-hydroxywarfarin-(d5-phenyl) as the internal standard.

CYP2A6: The 7-hydroxylation of coumarin (4 µM). The reaction is monitored by HPLC using florescence detection.

CYP2C9: The 7-hydroxylation of (S)-warfarin (4 µM). The reaction is monitored by quantitative GC/MS using 7-hydroxywarfarin-(d5-phenyl) as the internal standard.

CYP2C19: The 4'-hydroxylation of (S)-mephenytoin (50 µM). The reaction is monitored by quantitative GC/MS using mephenytoin-(d3-methyl) as the internal standard.

CYP2D6: The O-demethylation of dextromethorphan (5 µM). The reaction is monitored by high performance liquid chromatography (HPLC) using florescence detection.

CYP2E1: The formation of p-nitrocatechol from p-nitrophenol (40 µM). Amounts of product formed are monitored by HPLC.

CYP3A4: The 10-hydroxylation of (R)-warfarin (0.5 mM). The reaction is monitored by quantitative GC/MS using 10-hydroxywarfarin-(d5-phenyl) as the internal standard.

Gemcabene appeared not to significantly inhibit any of the seven human cytochrome P450 isoforms examined at the three concentrations (100, 300, and 1500 µM or 30.2, 90.7, and 453.6 µg/mL, respectively). While plasma-protein binding is nonlinear in humans, the concentrations of gemcabene used in this study exceed those used in binding studies by a 4-fold factor. At the highest concentration used (1500 µM), there appeared to be some marginal (10%-20%) inhibitory activity toward CYP2A6, CYP2D6, and CYP2C9. In contrast, CYP2E1 appeared to be slightly (about 20%) enhanced. These results suggest that a metabolically based clinical interaction between gemcabene and other drugs whose clearance are dependent upon one of the cytochrome P450 isoforms tested is highly unlikely at therapeutic concentrations of gemcabene.

As shown in Table 3, the IC50 values for the major human liver cytochrome P450 isoforms are greater than 1500 µM (453.6 µg/ml).

TABLE 3

| CYP450 | Approximate $IC_{50}$ |
| --- | --- |
| CYP1A2 | >1.5 mM |
| CYP2A6 | >1.5 mM |
| CYP2C9 | >1.5 mM |
| CYP2C19 | >1.5 mM |
| CYP2D6 | >1.5 mM |
| CYP2E1 | >1.5 mM |
| CYP3A4 | >1.5 mM |

Example 2

Distribution of Radiolabeled Gemcabene in Tissues of Male Rats.

Absorption, distribution, metabolism and elimination studies in rats administered radiolabeled gemcabene demonstrate that almost all drug was distributed in liver and kidney, the organs involved in gemcabene metabolism and elimination, with little or no distribution to muscle.

The study was performed with [$^{14}$C] gemcabene having a specific activity of 47.3 µCi/mg). The structure of [$^{14}$C] gemcabene showing the position of label (*) is shown below.

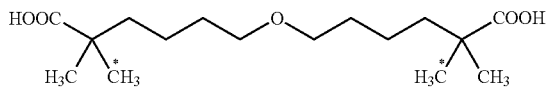

Dose solution was prepared by dissolving labeled drug in 0.45 mL ethanol and 4.05 mL 0.5% methylcellulose in water. Unlabeled gemcabene, was added to yield a 10 mg/kg solution. Final specific activity of dose solution was 10.37 µCi/mg.

Male Wistar rats with an average weight of 202 g were fasted overnight prior to dosing. Animals were given a single per oral (PO) dose of 10.0 mg/kg [$^{14}$C] gemcabene (approximately 21 µCi/rat), and two animals/time point were sacrificed at 1, 4, 8, 24, 48, 96, or 192 hours postdose by overwhelming halothane anesthesia. Carcasses were rapidly frozen in dry ice/hexane mixture and prepared for whole body sectioning and autoradiography. Sections of 50 m thickness were air dried at −20° C. and applied to BioMax scientific imaging film (Eastman Kodak, Rochester, N.Y.) or phosphor imaging plates for autoradiographic exposure (Molecular Dynamics, Sunnyvale, Calif.). Carbon-14 standards (American Radiolabeled Chemicals, St. Louis) were included on representative films and plates for calibration of the analyzer. Processed films were digitized with the analyzer scanner (Loats INQUIRY image analysis system, Loats Associates, Westminster, Md.), and radioactivity remaining in tissues was determined by quantitative video densitometric analysis of digital images. Imaging plates were scanned after 1-week exposure. Resulting electronic images were used for preliminary evaluation of distribution.

Table 4 shows the [14C]gemcabene radioequivalents remaining in tissue following a 10 mg/kg PO dose.

TABLE 4

| | µg equivalents/g | | | | | | |
| --- | --- | --- | --- | --- | --- | --- | --- |
| Time (hr) | 1 | 4 | 8 | 24 | 48 | 96 | 192 |
| Blood | 15.46 | 13.65 | 9.75 | 4.69 | 0.44 | BLQ | BLQ |
| Liver | 35.78 | 37.08 | 27.42 | 24.35 | 3.64 | 0.24 | BLQ |
| Kidney | 18.75 | 17.84 | 16.44 | 17.45 | 7.23 | 0.83 | 0.24 |
| Muscle | 1.35 | 1.40 | 0.99 | 0.45 | BLQ | BLQ | BLQ |
| Adrenal | 6.05 | 4.76 | 4.29 | 1.42 | 0.22 | BLQ | BLQ |
| Brain | 0.41 | 0.47 | 0.43 | 0.24 | BLQ | BLQ | BLQ |
| Lung | 11.69 | 10.15 | 7.59 | 3.58 | 0.36 | BLQ | BLQ |

Lower limit of quantitation = 0.10 µg/g.
BLQ—below level of quantitation

Example 3

Potential Interaction Between Statins and Gemcabene on Pharmacokinetics of Atorvastatin.

To further investigate potential interaction between statins and gemcabene, the effect of multiple-dose gemcabene (300 and 900 mg once daily [QD]) on the steady-state pharmacokinetics of atorvastatin (80 mg QD) was studied.

The trial was an open-label, multiple dose, 1-sequence, 3 treatment, crossover study in healthy subjects.

Twenty subjects received the following treatments (treatment 1) 80 mg atorvastatin QD for 5 days; (treatment 2) 80 mg atorvastatin QD with 300 mg gemcabene QD for 11 days (Days 6-16); and (treatment 3) 80 mg atorvastatin QD with 900 mg gemcabene QD for 11 days (Days 17-27). Medication was administered orally at approximately the same time of day for each treatment. Each dose was administered with 8 oz. of water.

Following the dose(s) on Days 5, 16, and 27, serial blood samples for atorvastatin and atorvastatin metabolite assays were collected for 24 hours. Three milliliters of venous blood was withdrawn in blood collection tubes containing sodium heparin. Blood samples were withdrawn before dosing and at 0.33, 0.66, 1, 2, 3, 4, 6, 8, 12, and 24 hours after the dose on days 5, 16, and 27. Following each collection blood samples were centrifuged as soon as possible, plasma separated and stored frozen at 70° C. until assayed for atorvastatin concentration.

Administration of 80 mg atorvastatin dosed alone or in combination with 300 and 900 mg gemcabene was well-tolerated by healthy volunteers. Based on comparisons of Cmax, tmax, AUC(0-24) and t1/2 values for atorvastatin, as well as for atorvastatin metabolites, gemcabene has no clinically important effect on atorvastatin pharmacokinetics. Pharmacokinetics data for atorvastatin are shown in Table 5 and the pharmacokinetic data for atorvastatin total analytes (atorvastatin plus its metabolites) are shown in Table 6.

TABLE 5

Least-Squares Mean Values

| Parameter | Atorvastatin Alone (Reference) | Atorvastatin With Gemcabene (Test) | Ratio | 90% Confidence Interval |
|---|---|---|---|---|
| 300 mg Gemcabene Once Daily | | | | |
| Cmax, ng/mL | 26.5 | 24.6 | 92.8 | 78.2 to 110 |
| tmax, hr | 1.03 | 0.752 | 72.7 | Not Applicable |
| AUC(0-24), ng · hr/mL | 119 | 113 | 94.9 | 85.8 to 105 |
| t½,* hr | 6.44 | 6.23 | 96.7 | 82.9 to 111 |
| 900 mg Gemcabene Once Daily | | | | |
| Cmax, ng/mL | 26.5 | 24.7 | 93.3 | 78.3 to 111 |
| tmax, hr | 1.03 | 1.07 | 103 | Not Applicable |
| AUC(0-24), ng · hr/mL | 119 | 114 | 96.0 | 86.6 to 106 |
| t½,* hr | 6.44 | 6.33 | 98.2 | 84.1 to 112 |

Ratio = Ratio of treatment mean values, expressed as a percentage (100% × test/reference).
90% Confidence Interval = 90% confidence interval estimate for the ratio (test/reference) of treatment mean values, expressed as a percentage of the reference mean.
*= Values for t½ are based on 0 to 24 hour data only and underestimate the true terminal half-life. Therefore, these values are substantially lower than those reported in previous studies.

In addition to determining the effect of gemcabene on the pharmacokinetics of atorvastatin, the effect of gemcabene on pharmacokinetics of the metabolites was determined as well. Based on AUC(0-24) values, exposure to atorvastatin total analytes following administration of 80 mg of atorvastatin with either 300 or 900 mg gemcabene was similar to that of 80 mg of atorvastatin alone. Differences in mean AUC(0-24) values were less than 7%. The 90% confidence intervals for the ratios of test/reference treatment AUC(0-24) values, based on log transformation, were within the 80% to 125% range indicating absence of an interaction of gemcabene on total analyte pharmacokinetics. Similar results were observed when total analyte concentrations were expressed in M or when only active analytes atorvastatin, o-hydroxy atorvastatin, and p-hydroxy atorvastatin were combined prior to analysis.

TABLE 6

Least-Squares Mean Values

| Parameter | Atorvastatin Alone (Reference) | Atorvastatin With Gemcabene (Test) | Ratio | 90% Confidence Interval |
|---|---|---|---|---|
| 300 mg Gemcabene Once Daily | | | | |
| Cmax, ng/mL | 83.5 | 74.3 | 89.0 | 76.7 to 103 |
| tmax, hr | 1.92 | 1.77 | 92.2 | Not Applicable |
| AUC(0-24), ng · hr/mL | 668 | 646 | 96.7 | 87.6 to 107 |
| t½*, hr | 6.13 | 5.97 | 97.3 | 89.4 to 105 |
| 900 mg Gemcabene Once Daily | | | | |
| Cmax, ng/mL | 83.5 | 82.8 | 99.1 | 85.2 to 115 |
| tmax, hr | 1.92 | 1.73 | 90.1 | Not Applicable |
| AUC(0-24), ng · hr/mL | 668 | 713 | 107 | 96.5 to 118 |
| t½*, hr | 6.13 | 6.20 | 101 | 93.0 to 109 |

Ratio = Ratio of treatment mean values, expressed as a percentage (100% test/reference).
90% Confidence Interval = 90% confidence interval estimate for the ratio (test/reference) of treatment mean values, expressed as a percentage of the reference mean.
*= Values for t½ are based on 0 to 24 hour data only and underestimate the true terminal half-life. Therefore, these values are substantially lower than those reported in previous studies.

Figure 1G:
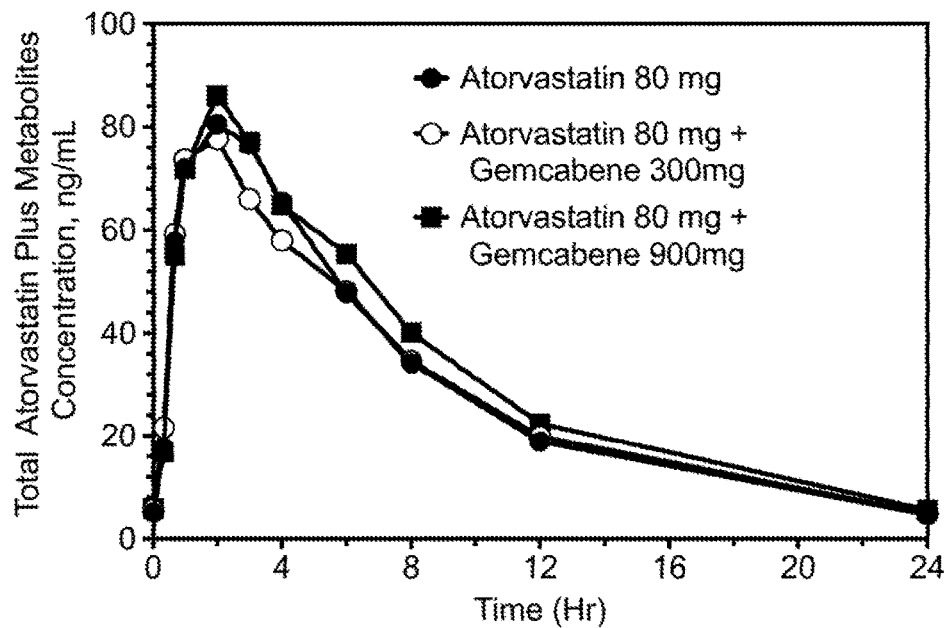
FIG. 1G is a graph showing the effect of gemcabene on the pharmacokinetics of atorvatatin administered alone at 80 mg (closed circles) and in combination with 900 mg gemcabene (open circles) as measured by activity of HMG-Co A reductase inhibitor concentration in a crossover study in human subjects.

The mean steady-state atorvastatin plasma concentration-time profiles for atorvastatin plasma concentration, atorvastatin lactone concentration, ortho-hydroxy atorvastatin, ortho-hydroxy atorvastatin lactone, para-hydroxy atorvastatin and para-hydroxy atorvastatin lactone are shown in graphical form in FIGS. 1A-1E. The mean steady-state atorvastatin plus metabolites plasma concentration-time profiles is shown in graphical form in FIG. 1G. (80 mg atorvastatin alone (closed circles), 80 mg atorvastatin with 300 mg gemcabene (open circles) and 80 mg atorvastatin with 900 mg gemcabene (closed squares)).

Effect of Gemcabene on Simvastatin Pharmacokinetics.

Healthy adult male and female subjects were treated once-daily oral simvastatin doses for 15 days and once-daily oral simvastatin and gemcabene doses for 15 days, separated by a 4-week washout period.

Blood Collection (Simvastatin)—Ten milliliters of venous blood were collected in vacuum blood collection tubes containing EDTA before and at 0.5, 1, 2, 3, 4, 6, 8, 12, and 24 hours after the simvastatin dose on Days 15 and 57. At each time point, plasma was harvested and separated into 2 aliquots, one for LC/MS/MS assay, and the other for EIA assay. Following collection of blood, samples were centrifuged, and plasma separated and stored frozen at −80° C. until analysis of drug concentration.

Blood Collection (gemcabene)—Five milliliters of venous blood were withdrawn in glass vacuum blood collection tubes containing 72 USP units of sodium heparin before, and at 0.5, 1, 2, 3, 4, 8, 12, and 24 hours after the gemcabene doses on Days 15 or 57. Following collection of blood, samples were centrifuged, and plasma separated and stored frozen at −20° C. until analysis.

Table 7 provides a summary of HMG-Co-A Reductase inhibitor pharmacokinetic parameter values following administration of 80 mg simvastatin alone (reference) and 900 mg gemcabene (CI-1027) (Test)

TABLE 7

Least-Squares Mean Values

| Parameter | Simvastatin Alone (Reference) | Simvastatin and CI-1027 (Test) | Ratio | 90% Confidence Interval |
|---|---|---|---|---|
| Cmax, ng equi/mL | 37.6 | 29.3 | 77.9 | 66.9 to 90.6 |
| tmax, hr | 1.55 | 1.95 | 126 | Not Applicable |
| AUC(0-24), ng equi · hr/mL | 211 | 219 | 104 | 93.9 to 116 |
| t½, hr | 8.15 | 8.73 | 107 | 96.6 to 118 |
| Cmin, ng equi/mL | 1.69 | 2.13 | 126 | 97.1 to 162 |

Parameters are described in Table 4.
Ratio = Ratio of treatment mean values, expressed as a percentage (100% × test/reference).
90% Confidence Interval = 90% confidence interval estimate for the ratio (test/reference) of treatment mean values, expressed as a percentage of the reference mean.

Figure 1H:
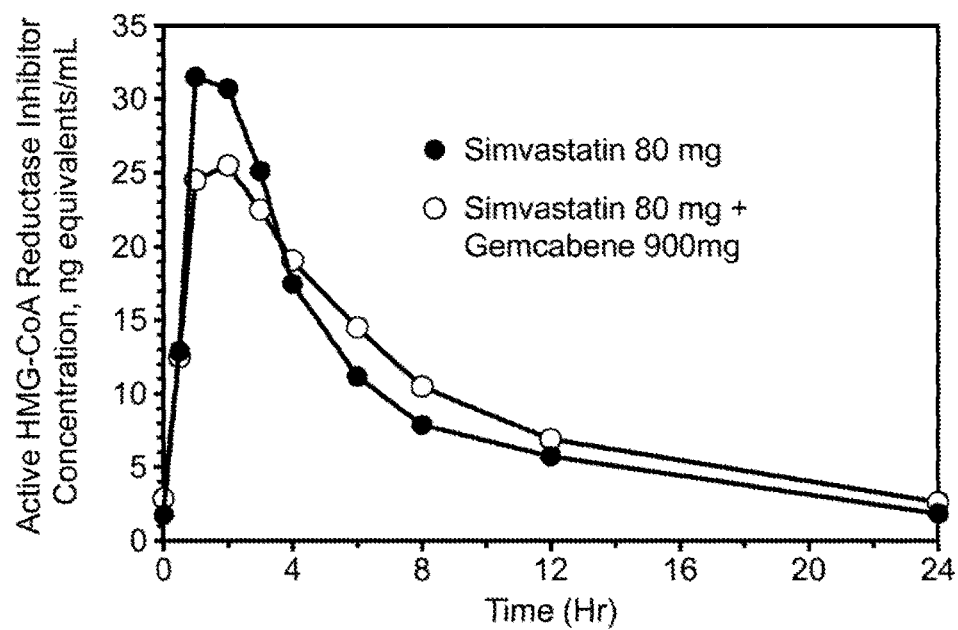
FIG. 1H is a graph showing the effect of gemcabene on the pharmacokinetics of simvastatin administered alone at 80 mg (closed circles) and in combination with 900 mg gemcabene (open circles) as measured by activity of HMG-Co A reductase inhibitor concentration in a crossover study in human subjects.
Figure 2A:
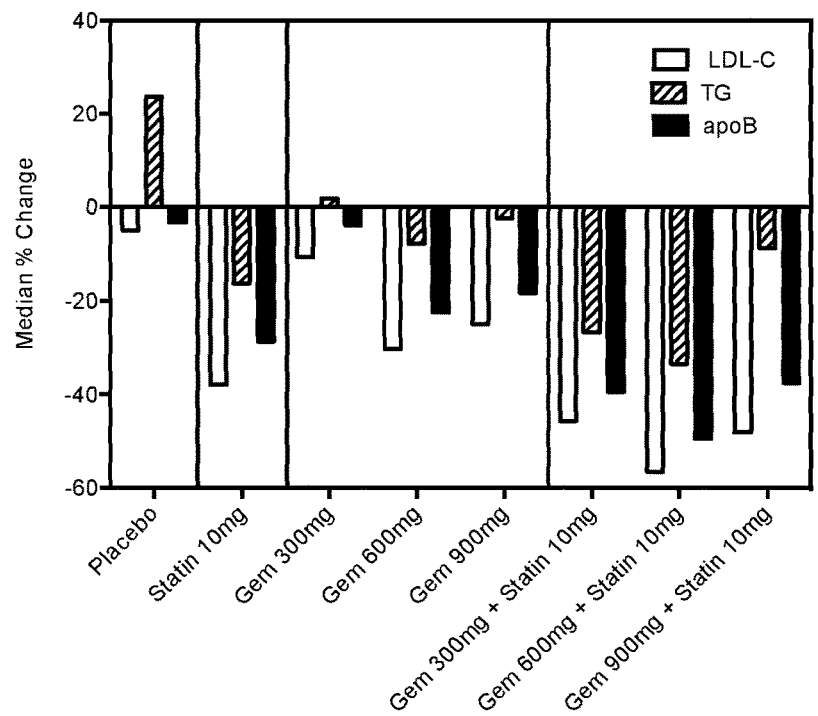
FIGS. 2A and 2B are bar graphs illustrating the median percent (2A) and mean percent (2B) change from baseline of LDL, baseline triglycerides, and baseline ApoB levels in type IIb patients that were administered placebo; 10 mg atorvastatin (statin); 300 mg, 600 mg, or 900 mg of gemcabene (gem); or 10 mg atorvastatin and 300 mg, 600 mg, or 900 mg of gemcabene, according to the study described in Example 4.
Figure 2B:
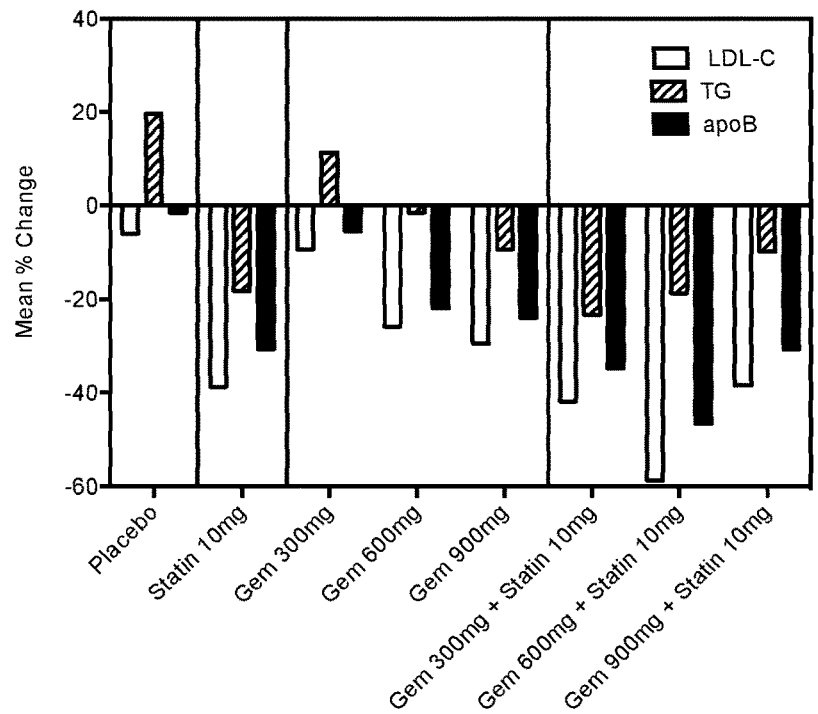
Figure 2C:
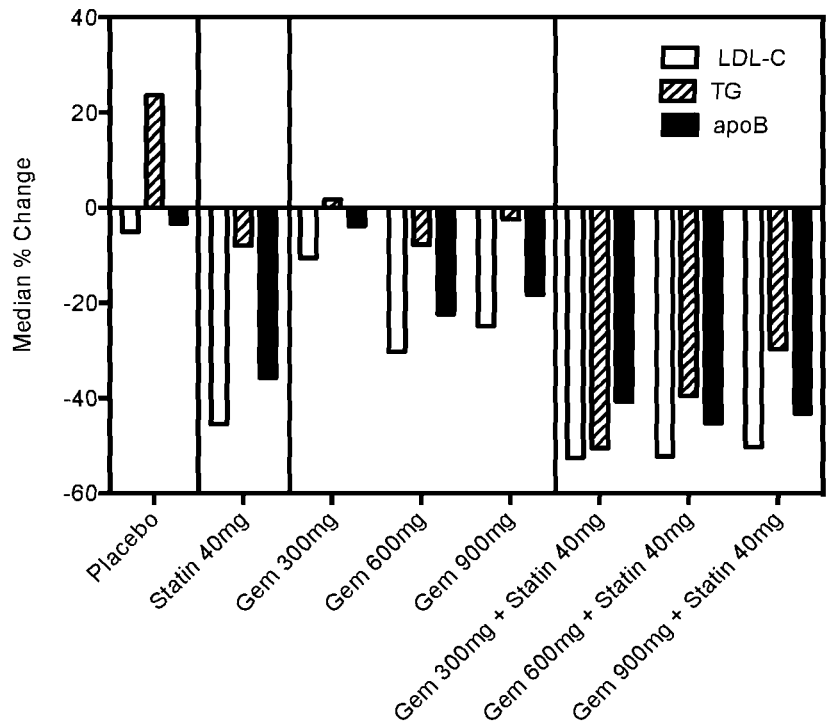
FIGS. 2C and 2D are bar graphs illustrating the median percent (2C) and mean percent (2D) change from baseline of LDL, baseline triglycerides, and baseline ApoB levels in type IIb patients that were administered placebo; 40 mg atorvastatin (statin); 300 mg, 600 mg, or 900 mg of gemcabene (gem); or 40 mg atorvastatin and 300 mg, 600 mg, or 900 mg of gemcabene, according to the study described in Example 4.
Figure 2D:
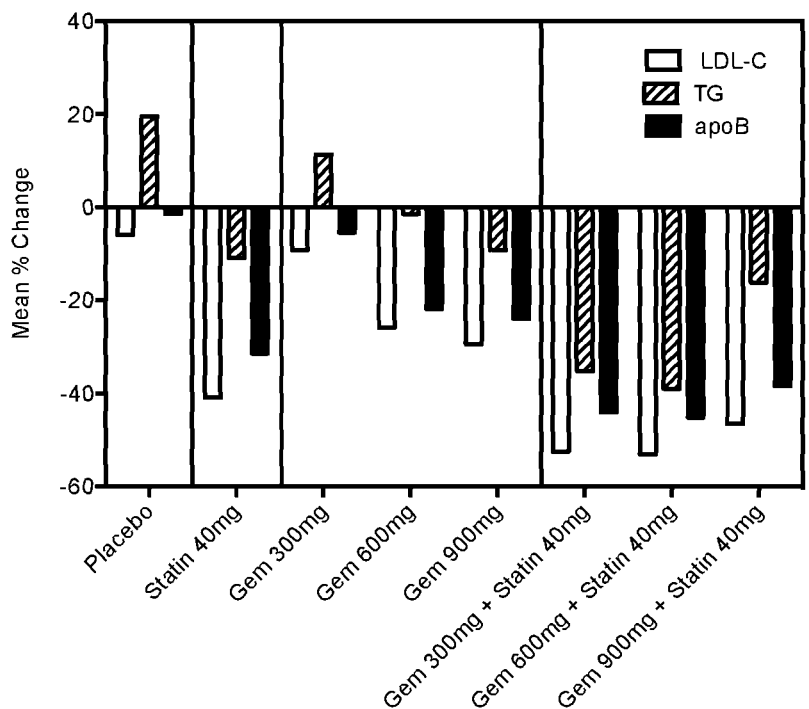
Figure 2E:
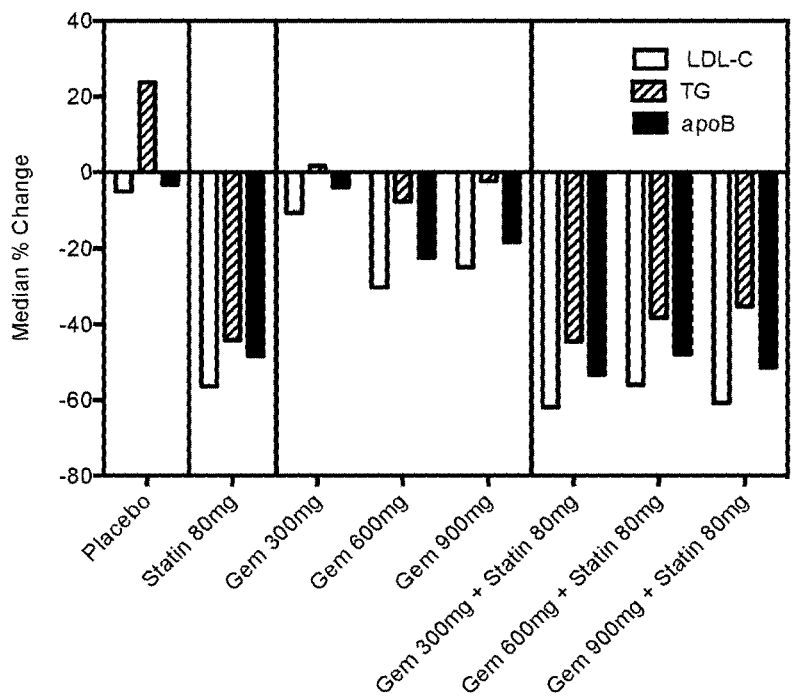
FIGS. 2E and 2F are bar graphs illustrating the median percent (2E) and mean percent (2F) change from baseline of LDL, baseline triglycerides, and baseline Apo B levels in type IIb patients that were administered placebo; 80 mg atorvastatin (statin); 300 mg, 600 mg, or 900 mg of gemcabene (gem); or 80 mg atorvastatin and 300 mg, 600 mg, or 900 mg of gemcabene, according to the study described in Example 4.
Figure 2F:
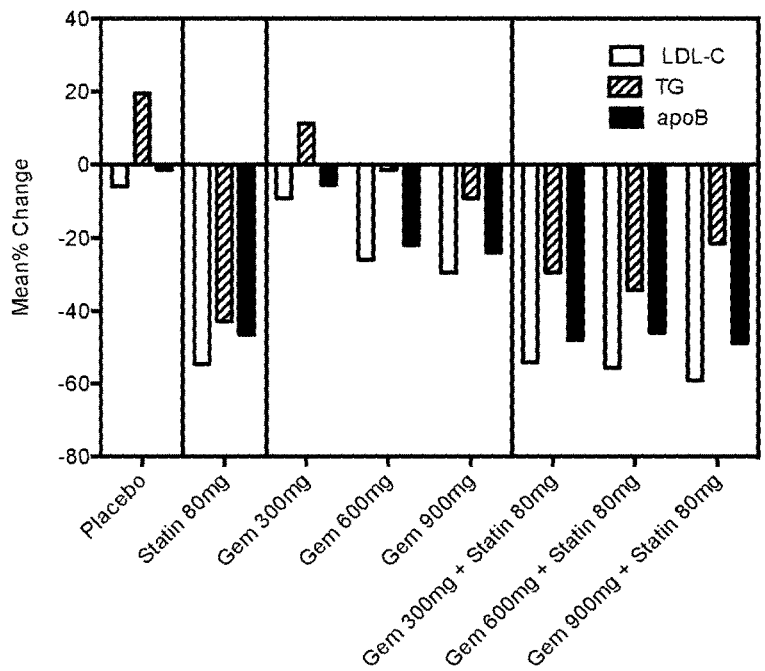

FIG. 1H show the mean active HMG-Co-A reductase inhibitor concentration after the administration of simvastatin (80 mg) alone (closed symbols) or in combination with gemcabene (600 mg) (open symbols). The results show that gemcabene lowers Cmax but has no effect on AUC. Little effect was observed on the catabolism of simvastatin or simvastatin metabolites when a high intensity dose of simvastatin (Concentration and parameter values for active HMG-Co-A reductase inhibitors are reported as ng-equivalents/mL, relative to simvastatin acid, the standard used in this assay.)

Example 4

Effect of the Combination of Gemcabene and a Statin in Lowering Levels of Plasma LDL-C, TG, and ApoB.

An 8-week, double-blind, randomized, placebo-controlled, dose-ranging study was done to evaluate the efficacy and safety of gemcabene administered as monotherapy or in combination with atorvastatin in the treatment of hypercholesterolemic patients. The primary objective was to evaluate the low-density lipoprotein cholesterol (LDL-C) lowering efficacy and dose response of gemcabene 300, 600, and 900 mg/day administered as a monotherapy or in combination with atorvastatin 10, 40, and 80 mg/day to hypercholesterolemia patients (Frederickson Types IIa and IIb). The secondary objective was to evaluate the modulation of high sensitivity c-reactive protein (hsCRP), high-density lipoprotein cholesterol (HDL), and triglycerides (TG), and apolipoprotein B (apo B) by gemcabene.

Subjects were randomized to receive placebo, the agents as monotherapy, or the agents combined as various dose levels for 8 weeks. Before and at the end of the treatment period, safety and lipid variable were assessed including plasma triglyceride, LDL-C and apo B levels.

Subgroup analysis of LDL-C and TG in subjects with an LDL-C level ≥130 mg/dl and a triglyceride level ≥150 mg/dL. (Type IIb) revealed a more than additive reduction in triglycerides in patients given less than 80 mg atorvastatin plus gemcabene (300, 600, or 900 mg). The reduction in triglycerides with combination therapy was much great than either the reduction with atorvastatin or gemcabene monotherapy. In addition, these combinations also caused further reductions in LDL-C and apo B.

The study was a parallel group, 4×4 factorial design, randomized, double-blinded, placebo-controlled multicenter study in hypercholesterolemic patients. The following table reflects the subset of subjects classified as having type IIb hypercholesterolemia.

Table 8 shows the 4×4 Factorial Design Used in 8-Week, Double-Blind Treatment Period.

TABLE 8

| Placebo<br>n = 10 | Gemcabene 300 mg<br>n = 7 | Gemcabene 600 mg<br>n = 14 | Gemcabene 900 mg<br>n = 13 |
|---|---|---|---|
| Atorvastatin 10 mg<br>n = 9 | Gemcabene 300 mg<br>Atorvastatin 10 mg<br>n = 11 | Gemcabene 600 mg<br>Atorvastatin 10 mg<br>n = 9 | Gemcabene 900 mg<br>Atorvastatin 10 mg<br>n = 11 |
| Atorvastatin 40 mg<br>n = 12 | Gemcabene 300 mg/<br>Atorvastatin 40 mg<br>n = 9 | Gemcabene 600 mg<br>Atorvastatin 40 mg<br>n = 8 | Gemcabene 600 mg<br>Atorvastatin 40 mg<br>n = 9 |
| Atorvastatin 80 mg<br>n = 8 | Gemcabene 300 mg<br>Atorvastatin 80 mg<br>n = 10 | Gemcabene 600 mg<br>Atorvastatin 80 mg<br>n = 8 | Gemcabene 900 mg<br>Atorvastatin 80 mg<br>n = 13 |

The study had 3 periods: (1) a lipid medication washout visit if needed; (2) a qualifying period; and (3) an 8-week double-blind treatment period. Patients were randomized with equal probability to receive 1 of 16 drug treatments comprising varying doses of gemcabene and/or atorvastatin and/or placebo as detailed above (Table 6). Study medication was taken orally once daily (QD) in the morning. Patients, site personnel, and the sponsor were blinded to treatment and plasma lipid levels during the 8-week treatment period. The "n" in the table above represents the number of patients in the study that had LDL-C≥130 mg/dL and TG>150 mg/dL at baseline (type IIb patients).

Study medication was dispensed at 4-week intervals in 7-day trays with separate daily allotments. Patients were instructed to take all tablets corresponding with the appropriate daily allotment in the morning. Gemcabene was supplied as a 300-mg tablet with matching placebo. Atorvastatin was supplied as 10- or 40-mg tablets with matching placebo. Study medication was packaged in 7-day blister packages with separate daily allotments containing 6 tablets per day.

Basic lipid assessments were performed on blood samples collected at each clinic visit. For total cholesterol, LDL-C, HDL-C, and triglycerides, baselines and percent changes from baseline were analyzed using a crossover ANOVA model. Due to potential period effects, the first and second period data were also analyzed separately using an ANOVA model consistent of treatment effects only.

Results are shown in FIGS. 2A through 2F.

The combination of 10 mg atorvastatin and gemcabene at 300 and 600 mg lowered TG levels an additional 10.5% and 17.3% respectively over atorvastatin alone. (median % change) Gemcabene at doses of 300, 600 and 900 further lowered LDL-C and ApoB as compared to 10 mg of atorvastatin alone.

The combination of 40 mg atorvastatin and gemcabene at 300, 600 and 900 mg lowered TG levels an additional 42.6%, 31.7% and 21.8%, respectively over atorvastatin alone. (median % change)

Example 5

Effect of Gemcabene, Atorvastatin and an Acetyl-CoA Carboxylase (ACC) Inhibitor on Cholesterol and Triglyceride Synthesis in Primary Rat Hepatocyte Cultures All experiments used cultures of primary rat hepatocytes (Sprague-Dawley) that were isolated and cultured as adapted from Ramharack R., et al., J Lipid Res 1995; 36:1294-304. One day after plating, cells were incubated with compound, in triplicate, at the indicated concentrations in parenchymal cell media minus fetal bovine serum, 1.0 mL per well in 6-well plates, with DMSO at a final concentration of 1%. Cells were incubated for 2 hours at 37° C. in a 95% $O_2$/5% $CO_2$ tissue culture incubator. At the end of incubation period, media was changed to labeling media consisting of compound, at the indicated concentrations, in parenchymal cell media minus fetal bovine serum and 30 µCi of 1-[$^{14}$C] acetate (Amersham), 1.0 mL per well and incubated for 4 hours at 37° C. in a tissue culture incubator. At end of labeling period, cells were washed with room temperature D-PBS, 2.0 mL per well and the reaction is stopped with 1.0 mL 0.75 N HCl. Cells were scraped and transferred to 15×45 mm glass vial (1 dram size). Wells were washed with 1.0 mL of methanol and added to scraped cells, followed by the addition of 2.0 mL of chloroform. Vials were capped and vortexed for 5 seconds and centrifuged in a Beckman GS 6KR centrifuge at 3,600 rpm for 15 minutes at room temperature to separate phases. The bottom chloroform phase was transferred to new 15×45 mm glass vial, dried down in a ReactiVap evaporator at 37° C. under nitrogen gas. Vials were cooled to room temperature and samples resuspended in 130 µL of n-heptane:chloroform, 4:1 by vortexing for 5 seconds. Samples were spotted onto 20×20 cm Whatman LK6D Silica Gel 60 A TLC plates and dried for 15 to 20 minutes in an 80° C. gravity convection oven. Plates were cooled to room temperature and chromatographed for 60 minutes at room temperature in isooctane: diethyl ether:glacial acetic acid, 75:25:2. Plates were dried for 30 minutes in an 80° C. gravity convection oven, cooled to room temperature, and wrapped in Saran™ Wrap. Plates were exposed overnight to phosphorimager plates, scanned on Typhoon Phosporlmager (Molecular Dynamics), and analyzed using Imagequant software (Molecular Dynamics).

Results

Treatment of primary rat hepatocytes with gemcabene significantly and concentration-dependently decreased cholesterol synthesis by 61.5±1.8 (SEM) %, ($p<1.8\times10^{-8}$), and 90.0±0.8%, ($p<1.0\times10^{-10}$), at concentrations of 10 µM and 30 µM, respectively (Table 7). Triglyceride synthesis was also dose-dependently reduced by 8.9±4.5%, ($p<0.12$) and 72.1±2.9%, ($p<4.1\times10^{-8}$), at concentrations of 10 µM and 30 µM, respectively, however, only the 30 µM dose reached statistical significance. In these cells the HMG-CoA reductase inhibitor, atorvastatin significantly reduced cholesterol synthesis by 93.7±0.4%, ($p<3.0\times10^{-10}$) at a dose of 1 µM without effecting triglyceride synthesis. The acetyl CoA carboxylase (ACC) inhibitor, CE 156860, did not significantly inhibit cholesterol synthesis at 3 µM, but significantly decreased triglyceride synthesis by 87.6±0.6%, ($p<0.0031$). (Table 7)

The data show that gemcabene is effective at inhibiting the synthesis of both cholesterol and triglyceride in primary rat hepatocyte cultures. This effect of gemcabene is different from the statin, atorvastatin, which inhibits cholesterol synthesis and an ACC inhibitor, CE 156860, which inhibits triglyceride synthesis. The inhibitory profile of gemcabene suggests that it may be individually affecting the cholesterol and triglyceride synthetic pathways or a common pathway that affects both synthetic pathways.

TABLE 9

| Compound | Dose (µM) | % Change in Synthesis | |
| --- | --- | --- | --- |
| | | Cholesterol ± SEM | Triglyceride ± SEM |
| Gemcabene | 10 | −61.5 ± 1.8%* | −8.9 ± 4.5%[ns] |
| Gemcabene | 30 | −90.0 ± 0.8%** | −72.1 ± 2.9%† |
| Atorvastatin | 1 | −93.7 ± 0.4%*** | 8.4 ± 4.0%[ns] |
| CE 156860 | 3 | −17.0 ± 2.8% | −87.6 ± 0.6%†† |

% Change calculated relative to vehicle cells. Each n represents a separate experiment, done in triplicate, using hepatocyes isolated from an individual animal. P-value calculated from a two-tailed, t-test.
*($p < 1.8 \times 10^{-8}$), n = 3;
**($p < 1.0 \times 10^{-10}$), n = 3;
***($p < 3.0 \times 10^{-10}$), n = 3;
†($p < 4.1 \times 10^{-8}$), n = 3;
††($p < 0.0031$), n = 1;
ns = not significant.

Example 6

Inhibition of Plasma and Hepatic Cholesterol and Triglyceride Synthesis in C57/BL6, apoB100/Lp(a) Mice.

Male mice 8 to 12 weeks of age were used in all studies. The apoB100/Lp(a) (cross of mice transgenic for human apoB100 and human apo(a)) mice) were obtained from Charles River. There were 8 animals per treatment group.

In this study gemcabene was dosed at 30 and/or 100 mg/kg. Simvastatin was dosed at 3 mg/kg. Drugs were prepared in vehicle (1.5% carboxymethylcellulose, 0.15% Tween 20™, balance in water) by polytron and vortex missing and orally administered using a dose volume of 0.1 mL/10 g body weight.

Mice were acclimated for a minimum of 7 days to a reverse 12 hour light/12 hour dark cycle prior to administration of the first dose of test drug or vehicle. Test drugs and vehicle were administered by oral gavage about 2 hours prior to the middle of the dark period. Test drugs and vehicle were given once daily. Thirty minutes after the eighth dose, 12.5 µCi [$^{14}$C] sodium acetate was administered. At 4 hours post [$^{14}$C] sodium acetate administration, mice were euthanized and exsanguinated by cardiac puncture for plasma collection. Individual plasma samples were acquired by placing whole blood samples into EDTA loaded centrifuge tubes and centrifuged. Plasma was transferred to new tubes and stored at −20° C. until assayed for [$^{14}$C] labeled cholesterol.

Liver samples were flash frozen in liquid nitrogen and stored at −80° C. until assayed for [$^{14}$C] labeled cholesterol and triglycerides.

Assay for Plasma [$^{14}$C] Labeled Cholesterol.

Frozen plasma samples (0.2-0.4 mL volume) were allowed to thaw, and were adjusted to 1 mL total volume with physiological saline. Additionally, 0.025 µCi [$^{14}$H] cholesterol (Perkin Elmer Life Sciences Inc. Boston, Mass.) was added to each sample, and to 2 or 3 spike controls in 7-mL scintillation vials, as an extraction internal standard. Freshly prepared 10% KOH solution was then added at 2.5 mL per sample. Samples were vortexed and saponified at 75° C. for 1 hour. After the samples cooled µCi [$^{14}$C] labeled cholesterol was extracted with 2.5 mL petroleum ether per sample and shaken for 10 minutes, and then centrifuged for 10 minutes at 0° C. The organic phase was then transferred to scintillation vials and evaporated at 37° C. head block under nitrogen gas. Each sample was then dissolved in in 0.25 mL of 2 parts chloroform to 1 part per methanol by sonication. Five mL scintillant was added to each sample and the spike controls for direct [$^{3}$H] and [$^{14}$C] deteriorations per minute (DPM) recording using a Packard 2500TR Tri-Carb Liquid Scintillation Analyzer. The recovery of [$^{3}$H] cholesterol in each sample was compared to the mean total in the spike controls to determine the percent correction of the [$^{14}$C] counts extraction variance.

Assay for Liver [$^{14}$C] Labeled Cholesterol and Triglycerides.

Frozen liver samples were kept on dry ice during sample weighing procedures and assay preparations. Each sample was homogenized in a solution of ice-cold methanol; 0.5 N acetic acid. The homogenized samples were transferred to glass vials and 50 µL [$^{3}$H] in ethanol for a total of 1×10$^{5}$ DPM and 15 mL chloroform was added to each sample. Samples were then vortexed and centrifuged for 20 minutes at 3000 rpm at room temperature to separate the phases. The lower chloroform layer was transferred to new vials. The remaining upper aqueous phase was extracted in like manner with 15 mL chloroform 2 more times. The chloroform phases were pooled for each sample then washed 2 times with 15 mL 0.88% KCL, vortexed 20 seconds, and centrifuged for 20 minutes. The aqueous phase was discarded and the chloroform phase was washed 2 times in like manner with 15 mL 1 part methanol to 1 part water, discarding the aqueous phase. The chloroform samples were evaporated under nitrogen gas, and resuspended in 600 µL chloroform and 30 µL removed for scintillation counting. Sample volumes were adjusted for corrected percent recovery and a calculated volume to load based on total liver weight. Calculated volumes were spotted onto TLC plates and dried in an 80° C. oven. After the plates had cooled to room temperature, they were developed in 102 mL isooctane: diethyl ether:glacial acetic acid, 75:25:2, respectively. Plates were dried in an 80° C. oven and allowed to cool to room temperature, wrapped in plastic wrap, and exposed to the phosphorimager screen. Imagequant software was used to quantitate cholesterol and triglyceride bands.

Figure 3:
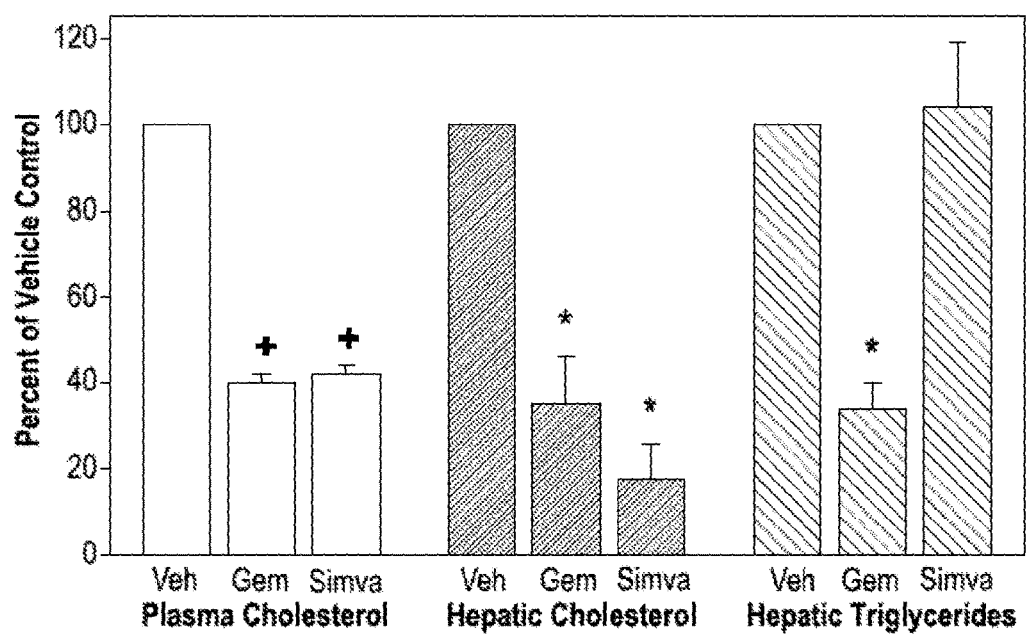
FIG. 3 is a bar graph illustrating the effect of gemcabene (Gem) at 100 mg/kg and simvastatin (Simva) at 3 mg/kg on plasma cholesterol, hepatic cholesterol and hepatic triglyceride synthesis.

As measured in plasma, gemcabene at 100 mg/kg significantly inhibited cholesterol synthesis by 60% and 3 mg/kg of simvastatin inhibited cholesterol synthesis by 59% (FIG. 3) The results show that in liver tissue gemcabene at 100 mg/kg inhibited both newly synthesized cholesterol by 65% and triglycerides by 66%, while simvastatin at 3 mg/kg only lowered cholesterol synthesis by 82% (FIG. 3 and Table 10).

The values shown in FIG. 3 are mean±SEM, n=8 per group. Veh=vehicle control, Gem=100 mg/kg gemcabene, simva=3 mg/kg simvastatin. +p-value <0.05 based on a 2-tailed t-test within one-factor ANOVA for % change, *p-value <0.05 based on a 2-tailed t-test versus vehicle on [$^{14}$C] cholesterol. The data showing the effect of gemcabene and simvastatin on apoB100/Lp(a) mouse hepatic triglyceride and cholesterol synthesis ([$^{14}$C] sodium acetate) are provided in Table 10.

TABLE 10

| Treatment | Parameter | % Change from Vehicle | p-value |
|---|---|---|---|
| Gemcabene 100 mg/kg | Triglycerides | −66 ± 6* | <0.040 |
| Gemcabene 100 mg/kg | Cholesterol | −65 ± 11* | <0.006 |
| Simvastatin 3 mg/kg | Triglycerides | 4.0 ± 15 | ns |
| Simvastatin 3 mg/kg | Cholesterol | −82 ± 8* | <0.004 |

*p-value <0.05 based on 2-tailed Student t-test versus vehicle on [$^{14}$C] cholesterol n = 8 mice per group;
ns = not significant.

The reduction of hepatic lipid, especially the reduction of hepatic TG, is useful in the treatment or prevention of NASH. In addition, gemcabene increases the oxidation of fatty acids further reducing the propensity for development of a fatty liver.

Example 7

In Vivo Efficacy Study of Gemcabene in STAM Model of Non-Alcoholic Steatohepatitis (NASH)
Materials and Methods
Test Substances:
Gemcabene was provided by Gemphire Therapeutics Inc. To prepare dosing solution, gemcabene was weighed and dissolved with vehicle [pure water] according to the formulation instructions. Telmisartan (Micardis®) was purchased from Boehringer Ingelheim GmbH (Germany) and dissolved in pure water.
Induction of NASH
NASH was induced in 40 male mice by a single subcutaneous injection of 200 µg streptozotocin (STZ, Sigma-Aldrich, USA) solution 2 days after birth and feeding with high fat diet (HFD, 57 kcal % fat, Cat# HFD32, CLEA Japan, Japan) after 4 weeks of age.
Route of Drug Administration
Vehicle (control) was administered orally in a volume of 10 mL/kg.

Gemcabene was administered orally in a volume of 10 mL/kg.
Telmisartan was administered orally in a volume of 10 mL/kg.
Treatment Doses:
Gemcabene was administered at doses of 30, 100 and 300 mg/kg once daily.
Telmisartan was administered at a dose of 10 mg/kg once daily.
Animals:
C57BL/6 mice (14-day-pregnant female) were obtained from Japan SLC, Inc. (Japan). All animals used in the study were housed and cared for in accordance with the Japanese Pharmacological Society Guidelines for Animal Use.
Environment:
The animals were maintained in a SPF facility under controlled conditions of temperature (23±2° C.), humidity (45±10%), lighting (12-hour artificial light and dark cycles; light from 8:00 to 20:00) and with room air exchange. The experimental room was pressurized to prevent contamination of the facility.
Animal Husbandry:
The animals were housed in TPX cages (CLEA Japan) with a maximum of 4 mice per cage. Sterilized Paper-Clean (Japan SLC) was used for bedding and replaced once a week.
Food and Drink:
A sterilized solid high-fat diet (HFD) was provided ad libitum, being placed in a metal lid on the top of the cage. Pure water was provided ad libitum from a water bottle equipped with a rubber stopper and a sipper tube. Water bottles were replaced once a week cleaned and sterilized in autoclave and reused.
Animal and Cage Identification:
Mice were identified by ear punch. Each cage was labeled with a specific identification code.
Measurement of Whole Blood and Plasma Biochemistry:
Eight-hour fasting blood samples were collected from facial vein at 3 days prior to termination.
Eight-hour fasting blood glucose was measured in whole blood using Life Check (EIDIA Co. Ltd., Japan). For plasma biochemistry, eight-hour fasting blood was collected in polypropylene tubes with anticoagulant (Novo-Heparin, Mochida Pharmaceutical, Japan) and centrifuged at 1,000×g for 15 minutes at 4° C. The supernatant was collected and stored at −80° C. until use. Plasma insulin levels were quantified by Ultra Sensitive Mouse Insulin ELISA kit (Morinaga Institute of Biological Science, Inc., Japan).
On the day of termination, non-fasting blood glucose was measured in whole blood using Life Check. For plasma biochemistry, non-fasting blood was collected in polypropylene tubes with anticoagulant (Novo-Heparin) and centrifuged at 1,000×g for 15 minutes at 4° C. The supernatant was collected and stored at −80° C. until use. Plasma ALT, AST, ALP, GGT, BUN, creatinine and total bilirubin levels were measured by FUJI DRI-CHEM 7000 (Fujifilm Corporation, Japan). Plasma ketone body levels were quantified by EnzyChrom™ Ketone Body Assay Kit (BioAssay Systems, USA).
Measurement of Liver Biochemistry
Measurement of Liver Triglyceride Content:
Liver total lipid-extracts were obtained by Folch's method (Folch J. et al., J. Biol. Chem. 1957; 226: 497). Liver samples were homogenized in chloroform-methanol (2:1, v/v) and incubated overnight at room temperature. After washing with chloroform-methanol-water (8:4:3, v/v/v), the extracts were evaporated to dryness, and dissolved in isopropanol. Liver triglyceride content was measured by Triglyceride E-test (Wako Pure Chemical Industries).

Measurement of Liver Hydroxyproline Content:

To quantify liver hydroxyproline content, frozen liver samples were processed by an alkaline-acid hydrolysis method as follows. Liver samples were defatted with 100% acetone, dried in the air, dissolved in 2N NaOH at 65° C., and autoclaved at 121° C. for 20 minutes. The lysed samples (400 µL) were acid-hydrolyzed with 400 µL of 6N HCl at 121° C. for 20 minutes, and neutralized with 400 µL of 4N NaOH containing 10 mg/mL activated carbon. AC buffer (2.2M acetic acid/0.48M citric acid, 400 µL) was added to the samples, followed by centrifugation to collect the supernatant. A standard curve of hydroxyproline was constructed with serial dilutions of trans-4-hydroxy-L-proline (Sigma-Aldrich) starting at 16 µg/mL. The prepared samples and standards (each 400 4) were mixed with 400 µL chloramine T solution (Wako Pure Chemical Industries) and incubated for 25 minutes at room temperature. The samples were then mixed with Ehrlich's solution (400 µL) and heated at 65° C. for 20 minutes to develop the color. After samples were cooled on ice and centrifuged to remove precipitates, the optical density of each supernatant was measured at 560 nm. The concentrations of hydroxyproline were calculated from the hydroxyproline standard curve. Protein concentrations of liver samples were determined using a BCA protein assay kit (Thermo Fisher Scientific, USA) and used to normalize the calculated hydroxyproline values. Liver hydroxyproline levels were expressed as µg per mg protein.

Histological Analyses:

For HE staining, sections were cut from paraffin blocks of liver tissue prefixed in Bouin's solution and stained with Lillie-Mayer's Hematoxylin (Muto Pure Chemicals Co., Ltd., Japan) and eosin solution (Wako Pure Chemical Industries). NAFLD Activity score (NAS) was calculated according to the criteria of Kleiner (Kleiner D E. et al., Hepatology, 2005; 41:1313). To visualize collagen deposition, Bouin's fixed liver sections were stained using picro-Sirius red solution (Waldeck, Germany).

For quantitative analysis of fibrosis area, bright field images of Sirius red-stained sections were captured around the central vein using a digital camera (DFC295; Leica, Germany) at 200-fold magnification, and the positive areas in 5 fields/section were measured using ImageJ software (National Institute of Health, USA).

Statistical analyses were performed using Bonferroni Multiple Comparison Test on GraphPad Prism 6 (GraphPad Software Inc., USA). P values <0.05 were considered statistically significant. Results were expressed as mean±SD.

Experimental Design and Treatment

Study Groups

Group 1: Vehicle in Normal

Eight normal mice (not administered streptozotocin) were orally administered vehicle [pure water] in a volume of 10 mL/kg once daily from 6 to 9 weeks of age.

Group 2: Vehicle in streptozotocin induced model of NASH

Eight NASH mice were orally administered vehicle in a volume of 10 mL/kg once daily from 6 to 9 weeks of age.

Group 3: Gemcabene 30 mg/kg in streptozotocin induced model of NASH

Eight NASH mice were orally administered vehicle supplemented with gemcabene at a dose of 30 mg/kg once daily from 6 to 9 weeks of age.

Group 4: Gemcabene 100 mg/kg in streptozotocin induced model of NASH

Eight NASH mice were orally administered vehicle supplemented with gemcabene at a dose of 100 mg/kg once daily from 6 to 9 weeks of age.

Group 5: Gemcabene 300 mg/kg in streptozotocin induced model of NASH

Eight NASH mice were orally administered vehicle supplemented with gemcabene at a dose of 300 mg/kg once daily from 6 to 9 weeks of age.

Group 6: Telmisartan 10 mg/kg in streptozotocin induced model of NASH

Eight NASH mice were orally administered pure water supplemented with Telmisartan at a dose of 10 mg/kg once daily from 6 to 9 weeks of age.

Table 11 below summarizes the treatment schedule:

TABLE 11

| Group | No. mice | Mice | Test substance | Dose (mg/kg) | Volume (mL/kg) | Regimen | Sacrifice (wks) |
|---|---|---|---|---|---|---|---|
| 1 | 8 | Normal | Vehicle | — | 10 | PO, QD, 6 wks-9 wks | 9 |
| 2 | 8 | STAM | Vehicle | — | 10 | PO, QD, 6 wks-9 wks | 9 |
| 3 | 8 | STAM | Gemcabene | 30 | 10 | PO, QD, 6 wks-9 wks | 9 |
| 4 | 8 | STAM | Gemcabene | 100 | 10 | PO, QD, 6 wks-9 wks | 9 |
| 5 | 8 | STAM | Gemcabene | 300 | 10 | PO, QD, 6 wks-9 wks | 9 |
| 6 | 8 | STAM | Telmisartan | 10 | 10 | PO, QD, 6 wks-9 wks | 9 |

Animal Monitoring and Sacrifice

The viability, clinical signs and behavior were monitored daily. Body weight was recorded before the treatment. Mice were observed for significant clinical signs of toxicity, moribundity and mortality approximately 60 minutes after each administration. The animals were sacrificed by exsanguinations through direct cardiac puncture under isoflurane anesthesia (Pfizer Inc.) at 9 weeks of age.

Results

Body Weight Changes and General Condition

Figure 4:
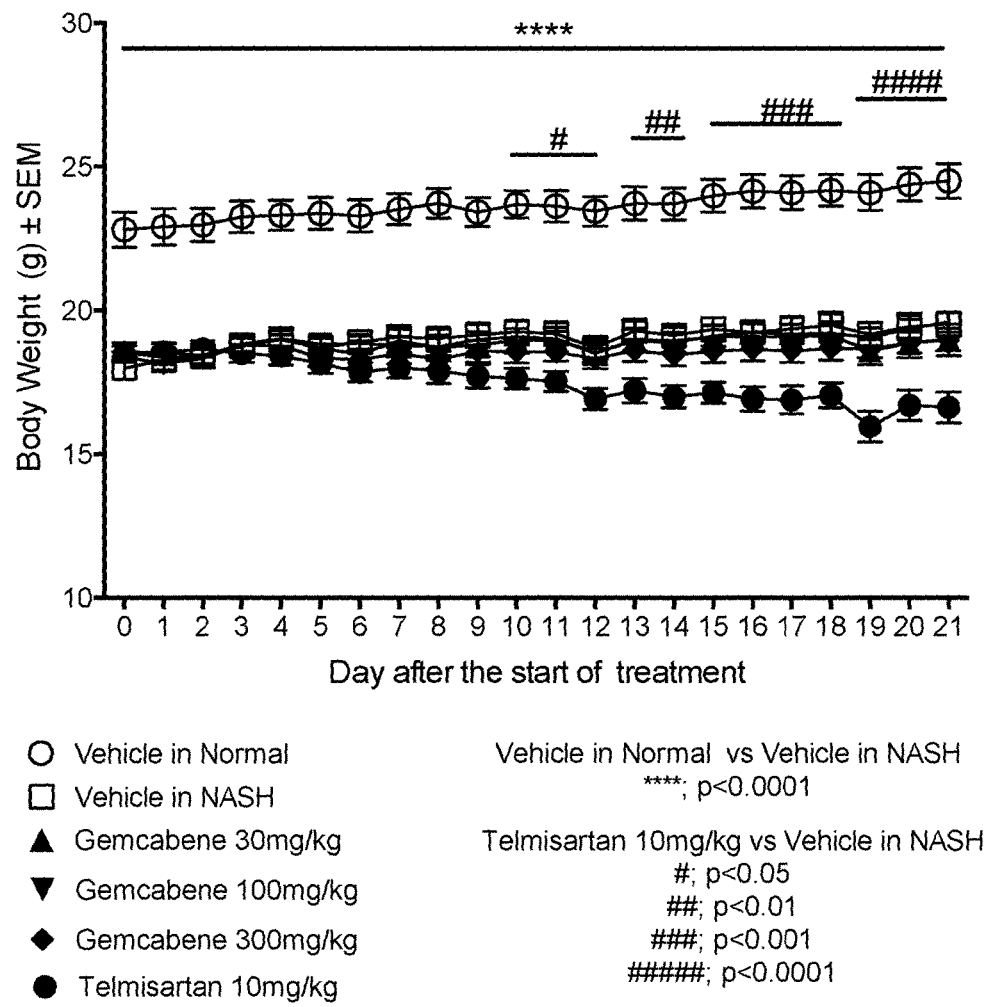
FIG. 4 is a graph showing the changes in mean body weight of the diabetic mouse NASH model as a function of the number of days after the start of treatment and the dose administered.

Mean body weight of the Vehicle in NASH group was significantly lower than that of the Vehicle in Normal group during the treatment period. Mean body weight of the telemisartan group was significantly lower than that of the Vehicle in NASH group from Day 10 to Day 21. There were no significant changes in mean body weight during the treatment period between the Vehicle in NASH group and the gemcabene treatment groups (FIG. 4). During the treatment period, one mouse was found dead before reaching Day 21 in the telemisartan group.

Body Weight on the Day of Termination

Figure 5B:
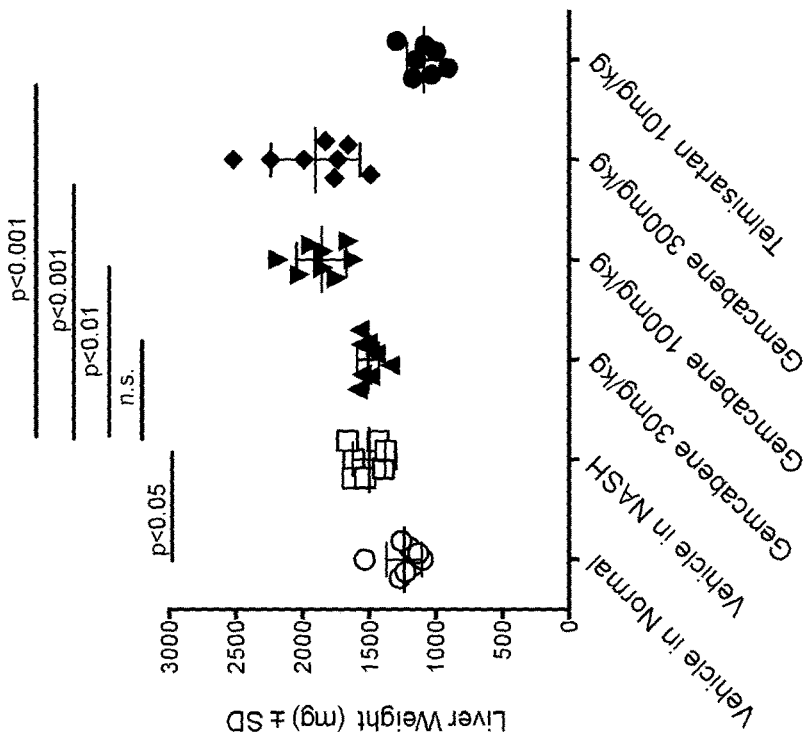
FIG. 5B is a plot showing the liver weight of the diabetic mouse NASH model on the day of termination of the treatment.
Figure 5A:
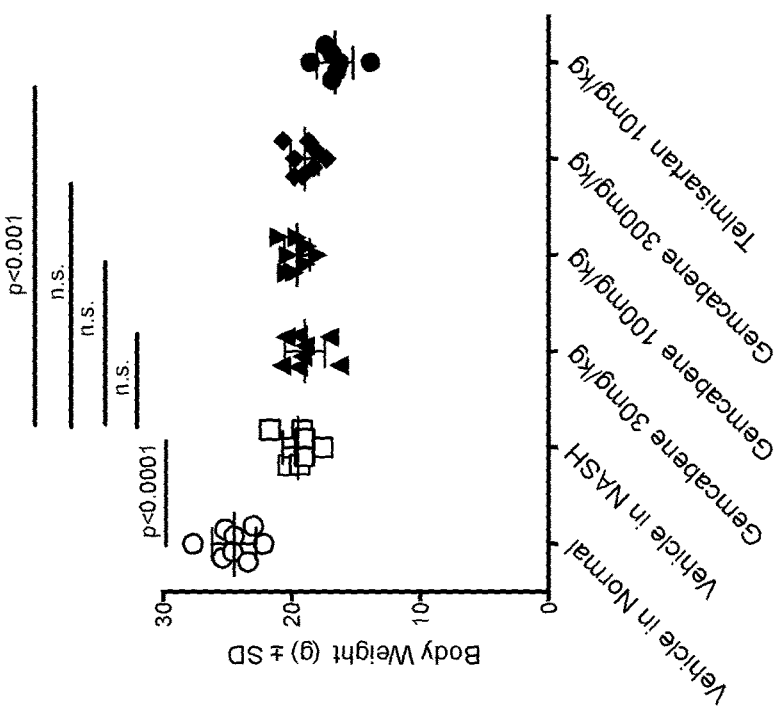
FIG. 5A is a plot showing the body weight of the diabetic mouse NASH model on the day of termination of the treatment.

The Vehicle in NASH group showed a significant decrease in mean body weight on the day of termination compared with the Vehicle in Normal group. The telemisartan group showed a significant decrease in mean body weight on the day of termination compared with the Vehicle in NASH group. There were no significant differences in mean body weight on the day of termination between the Vehicle in NASH group and the gemcabene treatment groups (FIG. 5A and Table 13).

Liver Weight and Liver-to-Body Weight Ratio

The Vehicle in NASH group showed a significant increase in mean liver weight compared with the Vehicle in Normal group. The gemcabene 100 and 300 mg/kg groups showed significant increases in mean liver weight compared with the Vehicle in NASH group. The telemisartan group showed a significant decrease in mean liver weight compared with the Vehicle in NASH group. There was no significant difference in mean liver weight between the Vehicle in NASH group and the gemcabene 30 mg/kg group (FIG. 5B and Table 13).

Figure 5C:
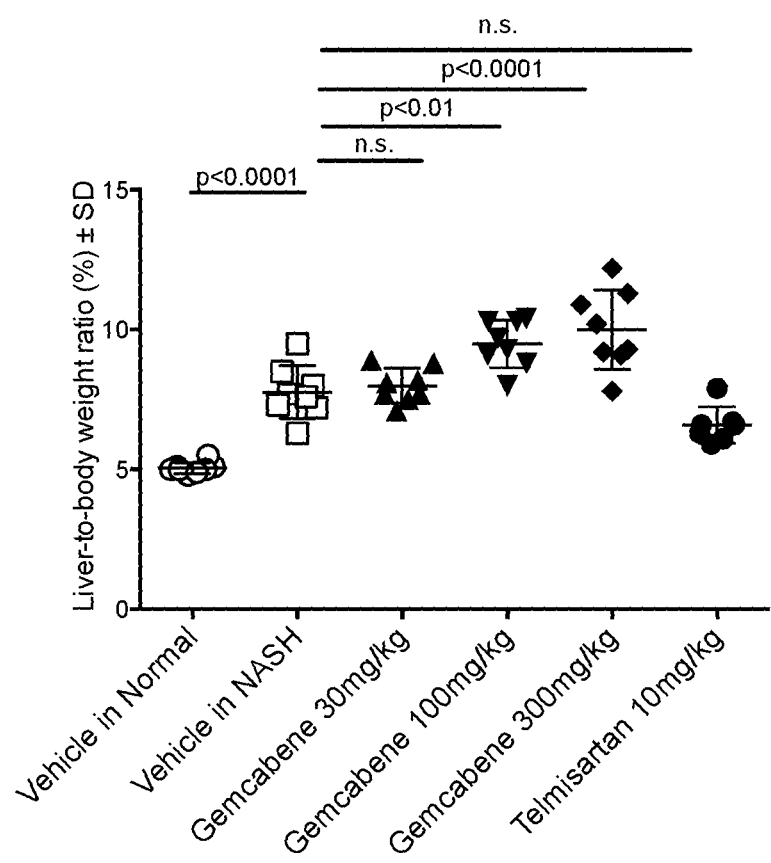
FIG. 5C is a plot showing the liver-to-body weight ratio of the diabetic mouse NASH model on the day of termination of the treatment.

The Vehicle in NASH group showed a significant increase in mean liver-to-body weight ratio compared with the Vehicle in Normal group. The gemcabene 100 and 300 mg/kg groups showed significant increases in mean liver-to-body weight ratio compared with the Vehicle in NASH group. There were no significant differences in mean liver-to-body weight ratio between the Vehicle in NASH group and any of the other treatment groups (FIG. 5C and Table 12).

At Termination

Figure 7B:
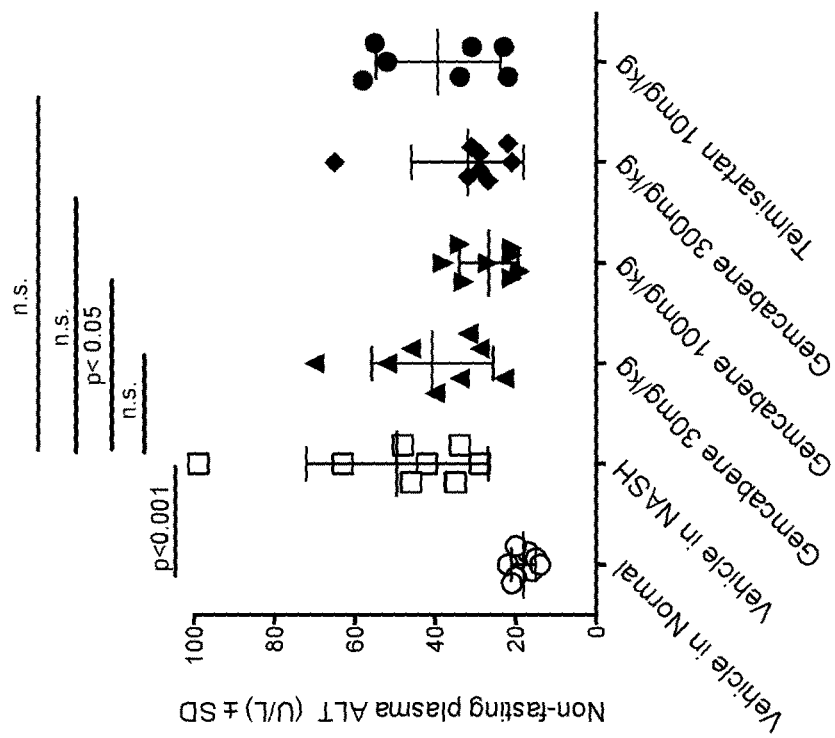
FIG. 7B is a plot showing the plasma alanine aminotransferase (ALT) levels of the diabetic mouse NASH model at termination.
Figure 7A:
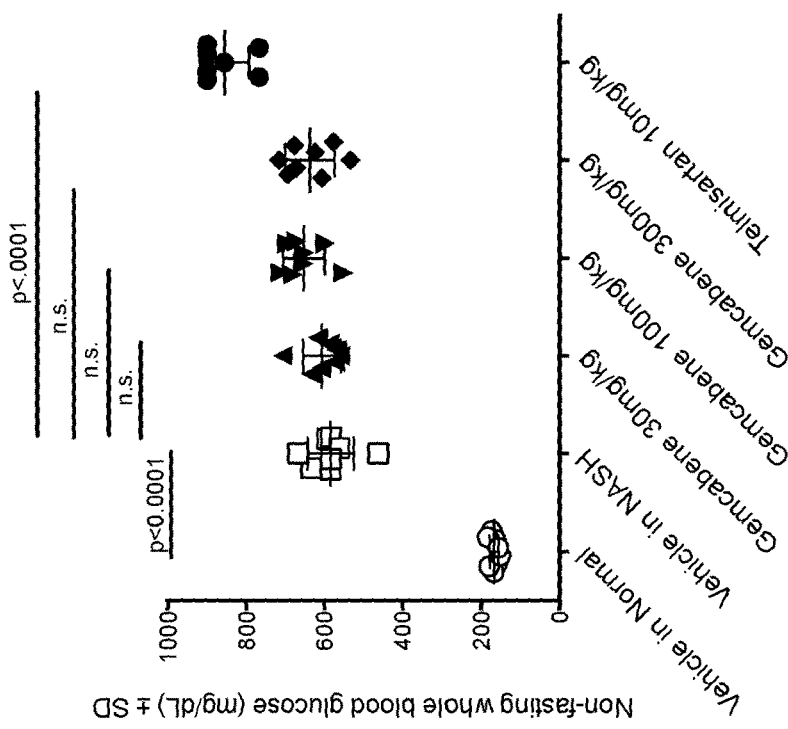
FIG. 7A is a plot showing the whole blood glucose levels of the diabetic mouse NASH model at termination.

Whole Blood Glucose:

The Vehicle in NASH group showed a significant increase in whole blood glucose levels compared with the Vehicle in Normal group. The telemisartan group showed a significant increase in whole blood glucose levels compared with the Vehicle in NASH group. There were no significant differences in whole blood glucose levels between the Vehicle in NASH group and the gemcabene treatment groups (FIG. 7A and Table 13).

Plasma ALT:

The Vehicle in NASH group showed a significant increase in plasma ALT levels compared with the Vehicle in Normal group. The gemcabene 100 mg/kg group showed a significant decrease in plasma ALT levels compared with the Vehicle in NASH group. There were no significant differences in plasma ALT levels between the Vehicle in NASH group and any of the other treatment groups (FIG. 7B and Table 13).

Figure 7D:
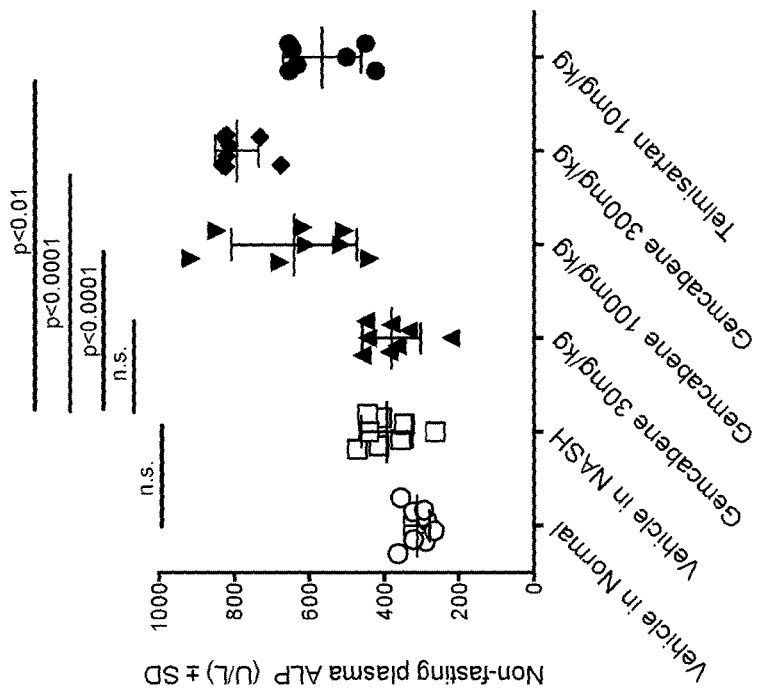
FIG. 7D is a plot showing the plasma alpha lipoic acid (ALP) levels of the diabetic mouse NASH model at termination.
Figure 7C:
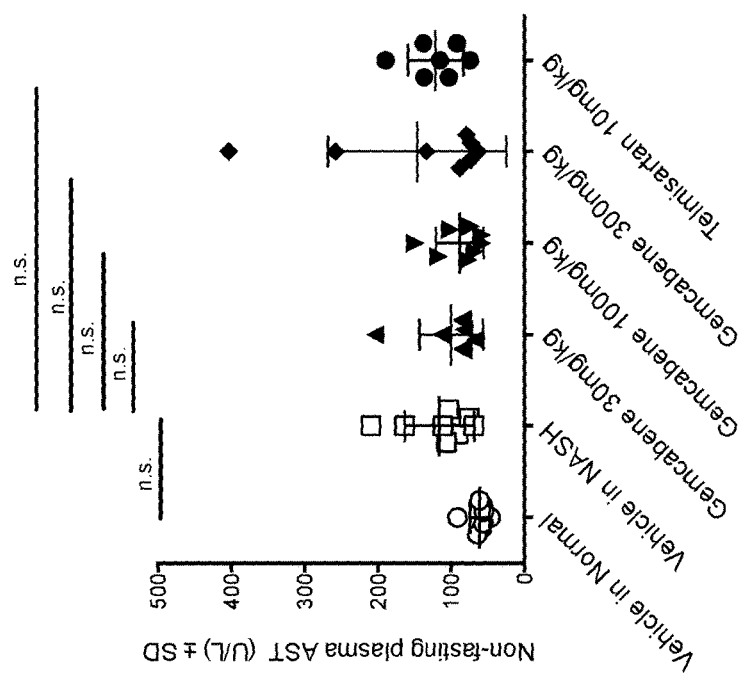
FIG. 7C is a plot showing the plasma aspartate aminotransferase (AST) levels of the diabetic mouse NASH model at termination.

Plasma AST:

There were no significant differences in plasma AST levels between the Vehicle in NASH group and any of the treatment groups (FIG. 7C and Table 13).

Plasma ALP:

The gemcabene 100 and 300 mg/kg groups and telemisartan group showed significant increases in plasma ALP levels compared with the Vehicle in NASH group. There were no significant differences in plasma ALP levels between the Vehicle in NASH group and any of the other treatment groups (FIG. 7D and Table 13).

Figure 7F:
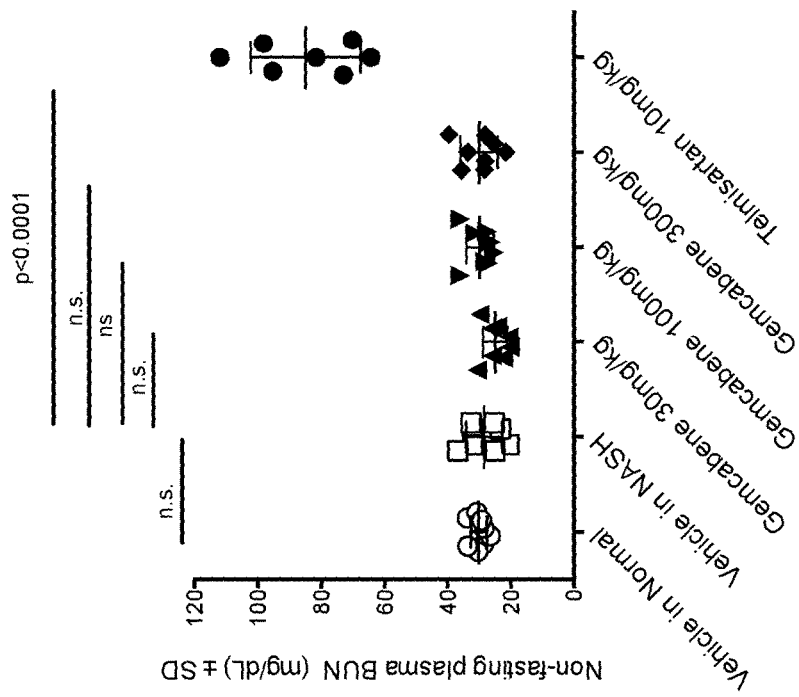
FIG. 7F is a plot showing the blood urea nitrogen (BUN) levels of the diabetic mouse NASH model at termination.
Figure 7E:
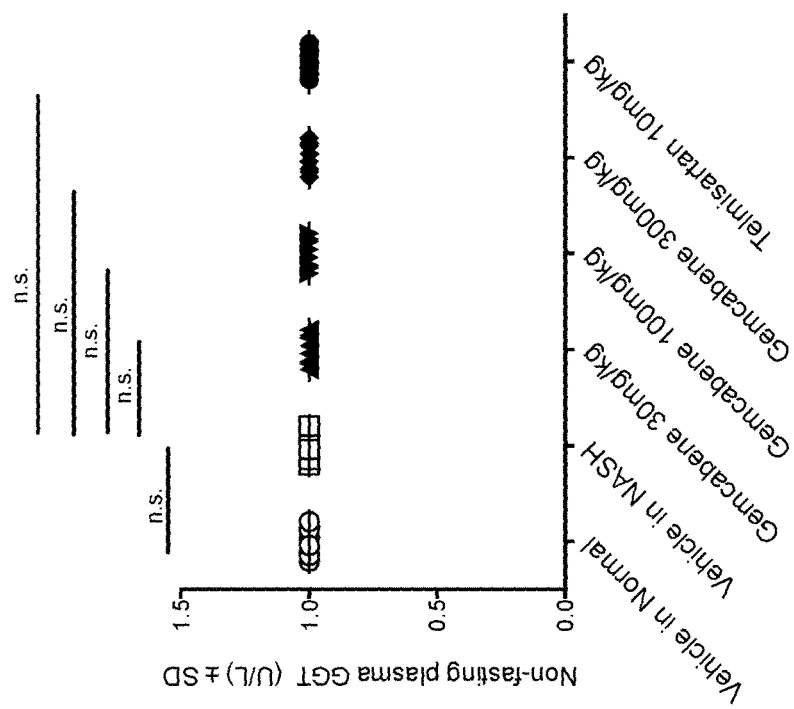
FIG. 7E is a plot showing the plasma gamma glutamyl transferase (GGT) levels of the diabetic mouse NASH model at termination.

Plasma GGT:

There were no significant differences in plasma GGT levels between the Vehicle in NASH group and any of the treatment groups (FIG. 7E and Table 13).

TABLE 12

Body weight and liver weight

| Parameter (mean ± SD) | Vehicle in Normal (n = 8) | Vehicle in NASH (n = 8) | Gemcabene 30 mg/kg (n = 8) | Gemcabene 100 mg/kg (n = 8) | Gemcabene 300 mg/kg (n = 8) | Telmisartan 10 mg/kg (n = 7) |
|---|---|---|---|---|---|---|
| Body weight (g) | 24.5 ± 1.7 | 19.5 ± 1.2 | 19.0 ± 1.6 | 19.6 ± 1.0 | 19.0 ± 1.1 | 16.6 ± 1.4 |
| Liver weight (g) | 1240 ± 133 | 1503 ± 122 | 1512 ± 82 | 1859 ± 189 | 1906 ± 0334 | 1094 ± 126 |
| Liver-to-body weight ratio (%) | 5.1 ± 0.2 | 7.8 ± 1.0 | 8.0 ± 0.6 | 9.5 ± 0.9 | 10.0 ± 1.4 | 6.6 ± 0.6 |

Biochemistry

At 3 Days Prior to Termination after 8 Hours of Fasting

Figure 6B:
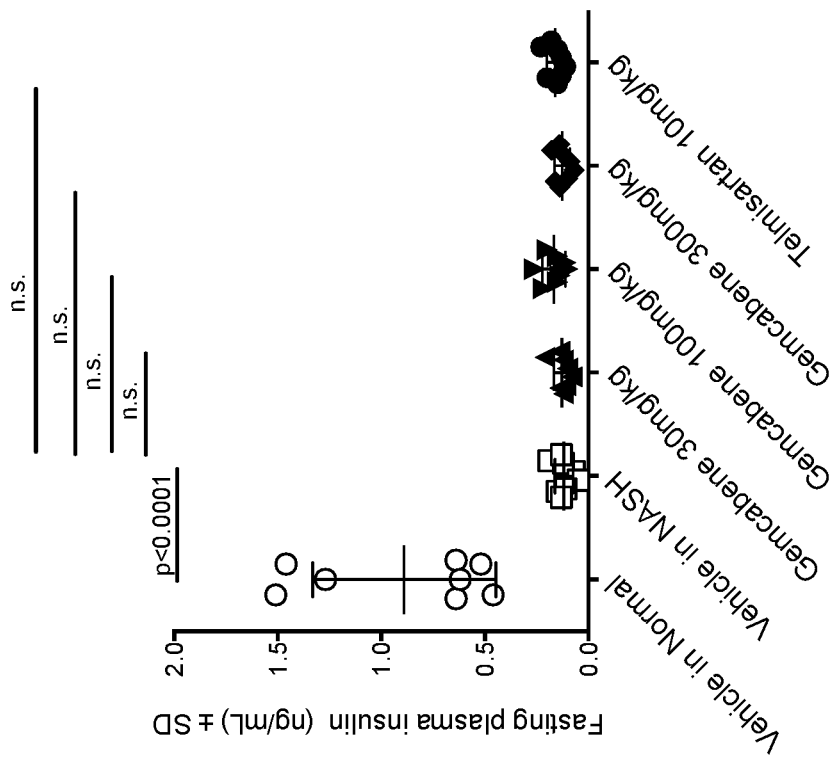
FIG. 6B is a plot showing the fasting plasma glucose levels of the diabetic mouse NASH model 3 days prior to termination, and after 8 hours of fasting.
Figure 6A:
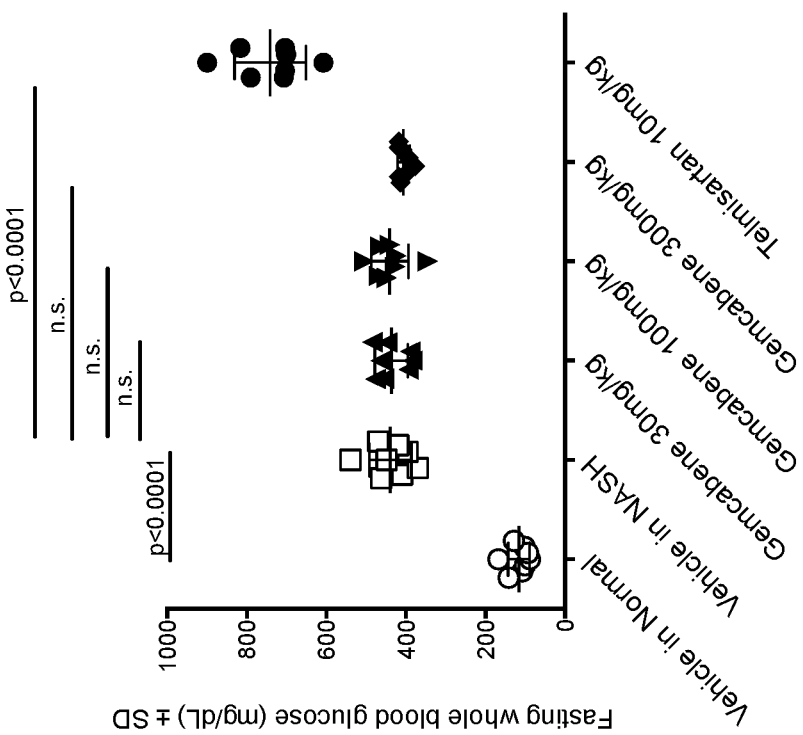
FIG. 6A is a plot showing the fasting whole blood glucose levels of the diabetic mouse NASH model 3 days prior to termination, and after 8 hours of fasting.

Fasting whole blood glucose:

The Vehicle in NASH group showed a significant increase in fasting whole blood glucose levels compared with the Vehicle in Normal group. The telemisartan group showed a significant increase in fasting whole blood glucose levels compared with the Vehicle in NASH group. There were no significant differences in fasting whole blood glucose levels between the Vehicle in NASH group and the gemcabene treatment groups (FIG. 6A and Table 13).

Fasting Plasma Insulin:

The Vehicle in NASH group showed a significant decrease in fasting plasma insulin levels compared with the Vehicle in Normal group. There were no significant differences in fasting plasma insulin levels between the Vehicle in NASH group and any of the other treatment groups (FIG. 6B and Table 13).

Plasma BUN:

The telemisartan group showed a significant increase in plasma BUN levels compared with the Vehicle in NASH group. There were no significant differences in plasma BUN levels between the Vehicle in NASH group and any of the other treatment groups (FIG. 7F and Table 13).

Plasma Creatinine:

The Vehicle in NASH group showed a significant decrease in plasma creatinine levels compared with the Vehicle in Normal group. The gemcabene 300 mg/kg group showed a significant increase in plasma creatinine levels compared with the Vehicle in NASH group. There were no significant differences in plasma creatinine levels between the Vehicle in NASH group and any of the other treatment groups (FIG. 7G and Table 13).

Figure 7H:
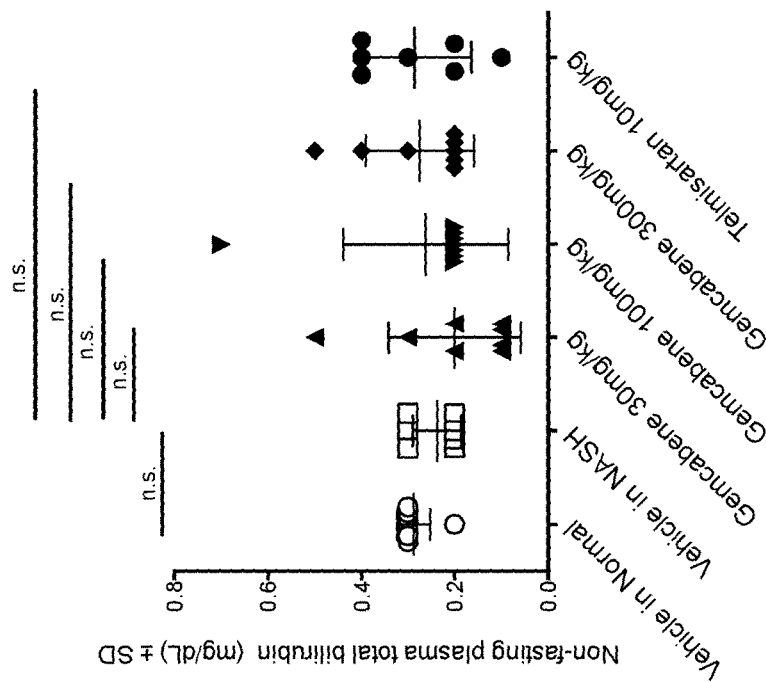
FIG. 7H is a plot showing the plasma whole bilirubin levels of the diabetic mouse NASH model at termination.
Figure 7G:
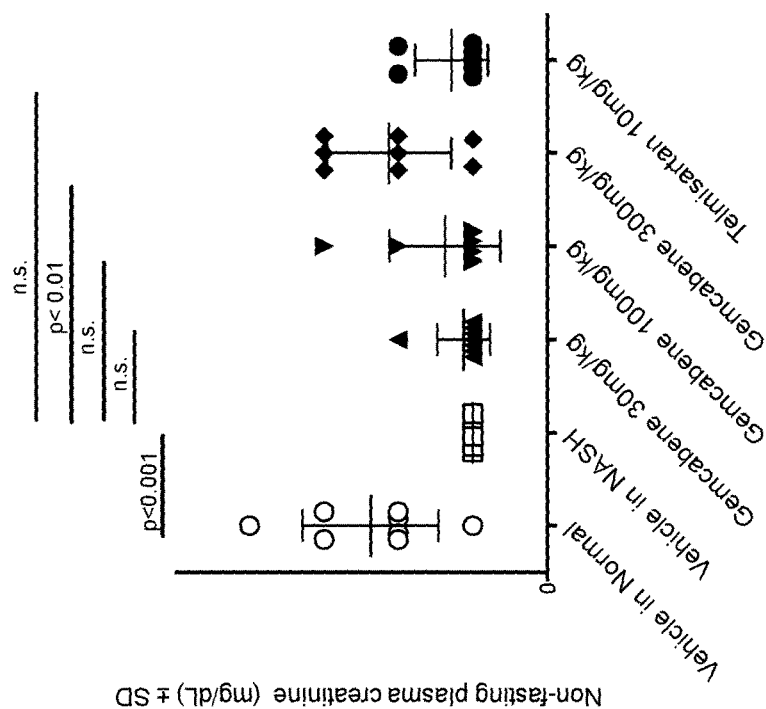
FIG. 7G is a plot showing the plasma creatinine levels of the diabetic mouse NASH model at termination.

Plasma Total Bilirubin:

There were no significant differences in plasma total bilirubin levels between the Vehicle in NASH group and any of the treatment groups (FIG. 7H and Table 13).

Figure 7J:
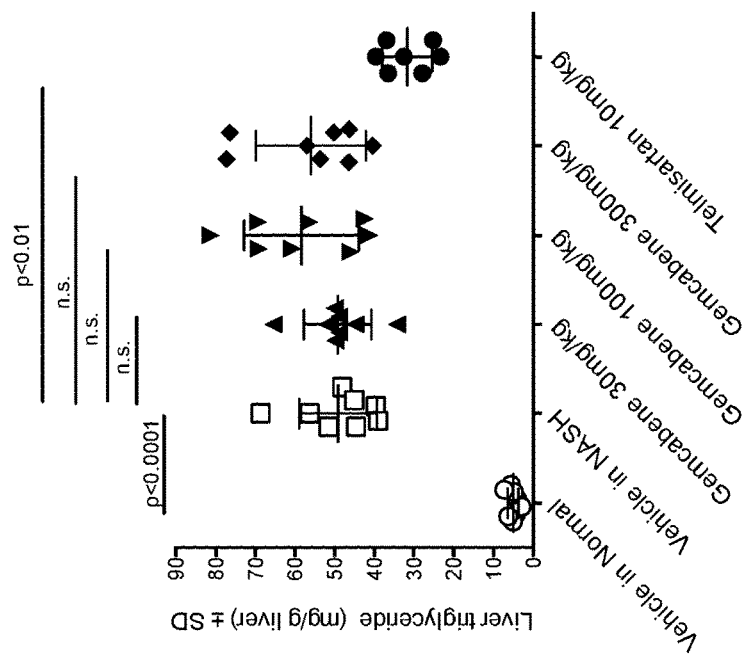
FIG. 7J is a plot showing the liver triglyceride levels of the diabetic mouse NASH model at termination.
Figure 7I:
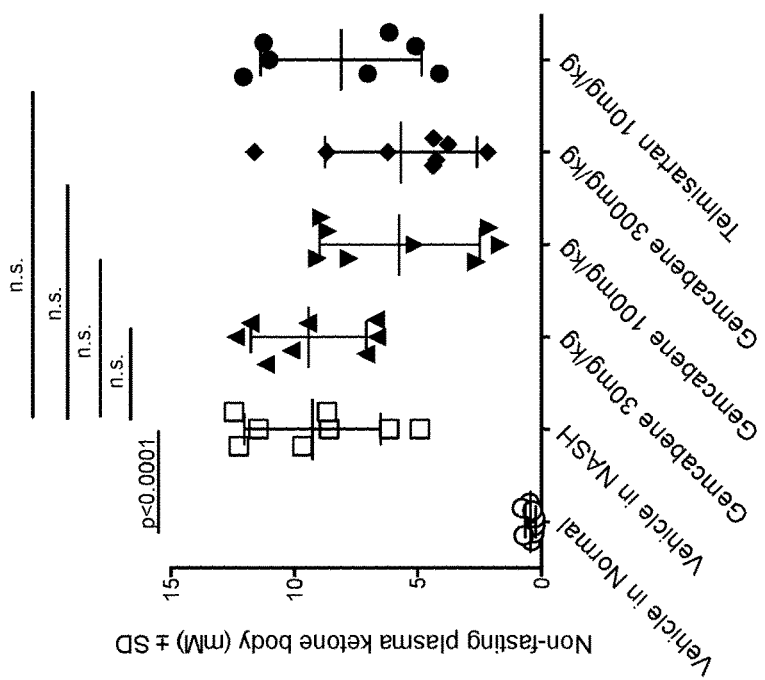
FIG. 7I is a plot showing the plasma ketone body levels of the diabetic mouse NASH model at termination.
Figure 8:
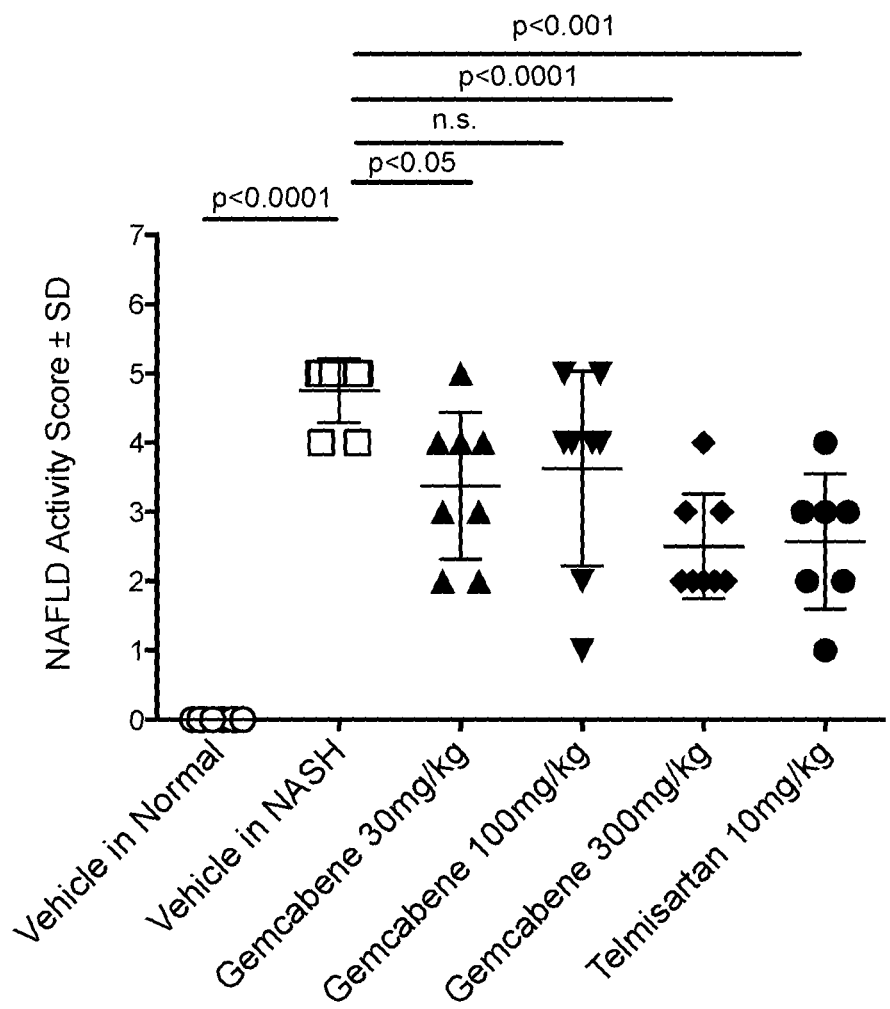
FIG. 8 is a plot showing the non-alcoholic fatty liver disease (NAFLD) score of the diabetic mouse NASH model at termination.
Figure 9B:
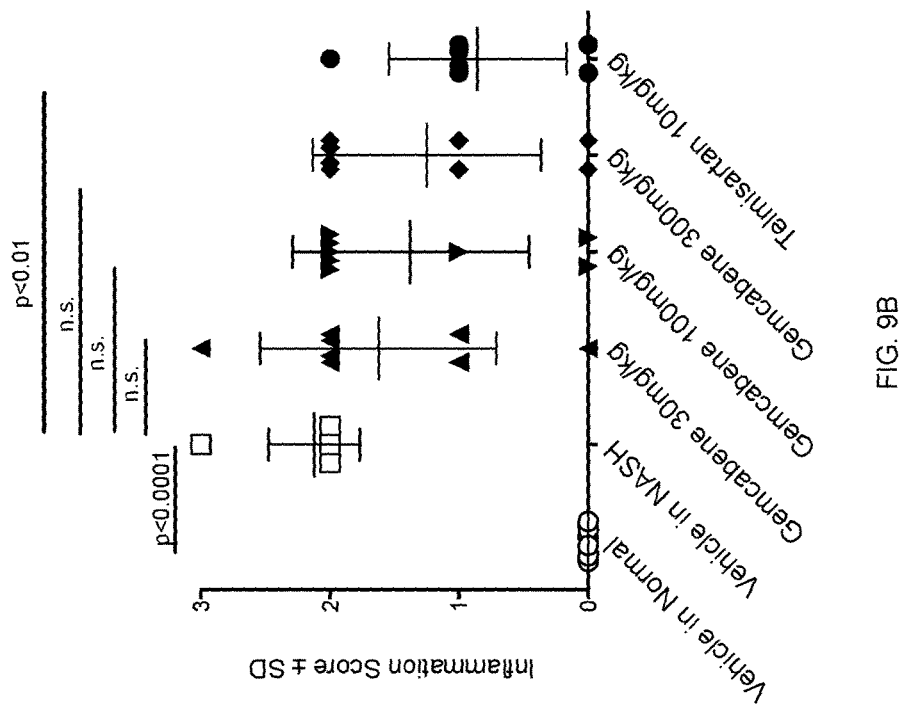
FIG. 9B is a plot showing the lobular inflammation score of the diabetic mouse NASH model at termination.
Figure 9A:
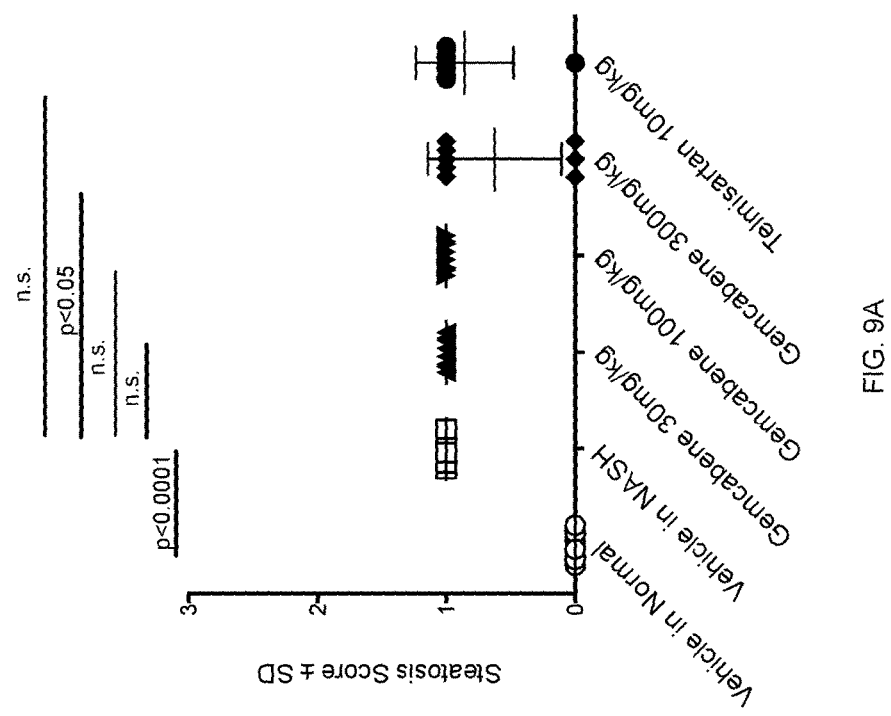
FIG. 9A is a plot showing the steatosis score of the diabetic mouse NASH model at termination.

Plasma Ketone Body:

The Vehicle in NASH group showed a significant increase in plasma ketone body levels compared with the Vehicle in Normal group. There were no significant differences in plasma ketone body levels between the Vehicle in NASH group and any of the other treatment groups (FIG. 7I and Table 13).

Liver Triglyceride:

The Vehicle in NASH group showed a significant increase in liver triglyceride contents compared with the Vehicle in Normal group. The telemisartan group showed a significant decrease in liver triglyceride contents compared with the Vehicle in NASH group. There were no significant differences in liver triglyceride contents between the Vehicle in NASH group and gemcabene treatment groups (FIG. 7J and Table 13).

Liver Hydroxyproline:

There were no significant differences in liver hydroxyproline contents between the Vehicle in NASH group and any of the treatment groups (FIG. 7K and Table 13).

Histological Analyses

HE Staining and NAFLD Activity Score

NASH is defined by the presence and pattern of specific histological abnormalities on liver biopsy. The NAFLD Activity Score (NAS), is a composite score that was developed as a tool to measure changes in NAFLD during therapeutic trials. NAS is a composite score comprised of three components that includes scores for steatosis, lobular inflammation and hepatocyte ballooning (Table 14). NAS score was defined as the unweighted sum of the scores for steatosis, lobular inflammation and hepatocyte ballooning. Steatosis grade is quantified as the percentage of hepatocytes that contain fat droplets. The fibrosis stage of the liver is evaluated separately from NAS by histological evaluation of the intensity of sinus red staining of collagen in the pericentral region of liver lobules.

Liver sections from the Vehicle in NASH group exhibited micro- and macrovesicular fat deposition, hepatocellular ballooning and inflammatory cell infiltration compared with the Vehicle in Normal group. The Vehicle in NASH group showed a significant increase in NAS compared with the Vehicle in Normal group. The gemcabene 30 and 300 mg/kg groups and telmisartan group showed significant reduction in NAS compared with the Vehicle in NASH group (FIGS. 8 and 9A-9C, and Table 14).

TABLE 13

Biochemistry

| Parameter (mean ± SD) | Vehicle in Normal Day 18: n = 8 Day 21: n = 8 | Vehicle in NASH Day 18: n = 8 Day 21: n = 8 | Gemcabene 30 mg/kg Day 18: n = 8 Day 21: n = 8 | Gemcabene 100 mg/kg Day 18: n = 8 Day 21: n = 8 | Gemcabene 300 mg/kg Day 18: n = 8 Day 21: n = 8 | Telmisartan 10 mg/kg Day 18: n = 8 Day 21: n = 7 |
|---|---|---|---|---|---|---|
| At 3 days prior to termination after 8 hours of fasting (Day 18) | | | | | | |
| Fasting blood glucose (mg/dL) | 117 ± 27 | 440 ± 53 | 437 ± 42 | 441 ± 46 | 407 ± 15 | 742 ± 90 |
| Plasma insulin (ng/mL) | 0.89 ± 0.44 | 0.12 ± 0.04 | 0.13 ± 0.04 | 0.17 ± 0.06 | 0.13 ± 0.04 | 0.16 ± 0.04 |
| At termination (Day 21) | | | | | | |
| Non-fasting blood glucose (mg/dL) | 168 ± 11 | 584 ± 60 | 607 ± 48 | 653 ± 53 | 638 ± 63 | 856 ± 62 |
| Plasma ALT (U/L) | 18 ± 3 | 50 ± 23 | 41 ± 15 | 27 ± 7 | 32 ± 14 | 39 ± 15 |
| Plasma AST (U/L) | 61 ± 13 | 116 ± 48 | 100 ± 44 | 88 ± 32 | 147 ± 122 | 121 ± 38 |
| Plasma ALP (U/L) | 313 ± 35 | 394 ± 68 | 382 ± 78 | 642 ± 167 | 794 ± 57 | 567 ± 104 |
| Plasma GGT (U/L) | 1 ± 0 | 1 ± 0 | 1 ± 0 | 1 ± 0 | 1 ± 0 | 1 ± 0 |
| Plasma BUN (mg/dL) | 30.2 ± 2.6 | 28.5 ± 5.7 | 25.0 ± 3.9 | 29.8 ± 4.3 | 30.1 ± 5.8 | 85.0 ± 17.4 |
| Plasma creatinine (mg/dL) | 0.2 ± 0.1 | 0.1 ± 0.0 | 0.1 ± 0.0 | 0.1 ± 0.1 | 0.2 ± 0.1 | 0.1 ± 0.0 |
| Plasma total bilirubin (mg/dL) | 0.3 ± 0.0 | 0.2 ± 0.1 | 0.2 ± 0.1 | 0.3 ± 0.2 | 0.3 ± 0.1 | 0.3 ± 0.1 |
| Plasma ketone body (mM) | 0.44 ± 0.21 | 9.28 ± 2.77 | 9.43 ± 2.35 | 5.75 ± 3.24 | 5.68 ± 3.08 | 8.11 ± 3.27 |
| Liver triglyceride (mg/g liver) | 5.1 ± 1.4 | 49.1 ± 9.8 | 49.2 ± 8.6 | 58.4 ± 14.5 | 56.0 ± 13.9 | 31.7 ± 6.4 |
| Liver hydroxylproline (µg/mg total protein) | 0.71 ± 0.11 | 0.74 ± 0.10 | 0.66 ± 0.12 | 0.74 ± 0.38 | 0.70 ± 0.10 | 0.91 ± 0.21 |

TABLE 14

NAFLD Activity score

| Group | n | Steatosis 0 | 1 | 2 | 3 | Lobular inflammation 0 | 1 | 2 | 3 | Hepatocyte ballooning 0 | 1 | 2 | NAS (mean ± SD) |
|---|---|---|---|---|---|---|---|---|---|---|---|---|---|
| Vehicle in Normal | 8 | 8 | — | — | — | 8 | — | — | — | 8 | — | — | 0.0 ± 0.0 |
| Vehicle in NASH | 8 | — | 8 | — | — | — | — | 7 | 1 | — | 3 | 5 | 4.8 ± 0.5 |
| Gemcabene 30 mg/kg | 8 | — | 8 | — | — | 1 | 2 | 4 | 1 | 4 | 2 | 2 | 3.4 ± 1.1 |
| Gemcabene 100 mg/kg | 8 | — | 8 | — | — | 2 | 1 | 5 | — | 1 | 4 | 3 | 3.6 ± 1.4 |
| Gemcabene 300 mg/kg | 8 | 3 | 5 | — | — | 2 | 2 | 4 | — | 4 | 3 | 1 | 2.5 ± 0.8 |
| Telmisartan 10 mg/kg | 7 | 1 | 6 | — | — | 2 | 4 | 1 | — | 2 | 4 | 1 | 2.6 ± 1.0 |

| Item | Score | Extent |
|---|---|---|
| Steatosis | 0 | <5% |
|  | 1 | 5-33% |
|  | 2 | >33-66% |
|  | 3 | >66% |
| Lobular Inflammation | 0 | No foci |
|  | 1 | <2 foci/200x |
|  | 2 | 2-4 foci/200x |
|  | 3 | >4 foci/200x |
| Hepatocyte Ballooning | 0 | None |
|  | 1 | Few balloon cells |
|  | 2 | Many cells/prominent ballooning |

Liver Fibrosis

Sirius Red Staining

Figure 10:
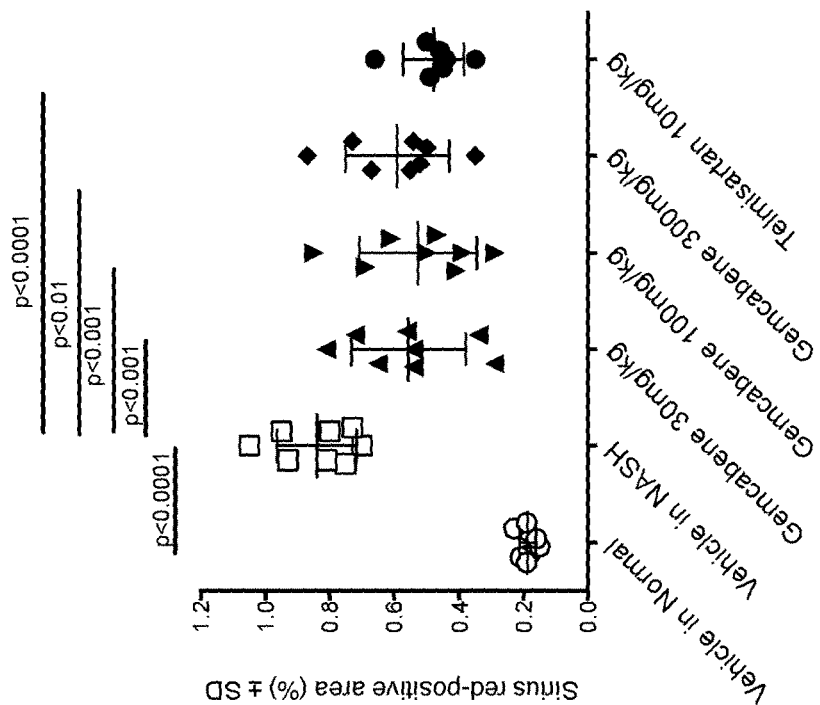
FIG. 10 is a plot showing the fibrosis area (% sirius red-positive area) of the diabetic mouse NASH model at termination.
Figure 9C:
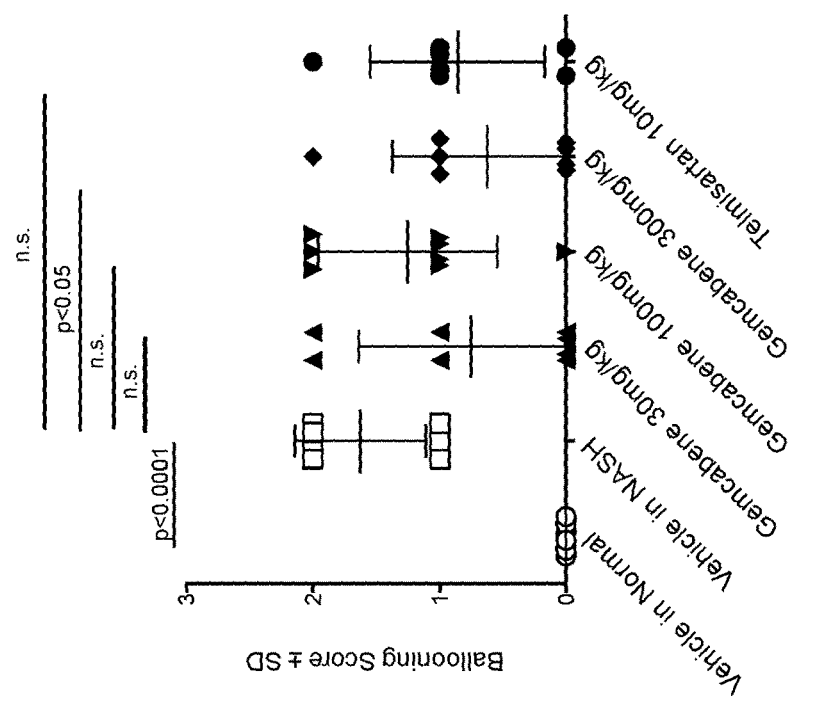
FIG. 9C is a plot showing the ballooning degeneration score of the diabetic mouse NASH model at termination.

Sirius red-stained liver sections were evaluated to determine liver fibrosis. Liver sections from the Vehicle in NASH group showed increased collagen deposition in the pericentral region of liver lobule compared with the Vehicle in Normal group. All groups showed significant decreases in fibrosis area compared with the Vehicle in NASH group (FIG. 10 and Table 15).

TABLE 15

Histological analysis

| Parameter (mean ± SD) | Vehicle in Normal (n = 8) | Vehicle in NASH (n = 8) | Gemcabene 30 mg/kg (n = 8) | Gemcabene 100 mg/kg (n = 8) | Gemcabene 300 mg/kg (n = 8) | Telmisartan 10 mg/kg (n = 7) |
|---|---|---|---|---|---|---|
| Sirius Red positive area (%) | 0.19 ± 0.03 | 0.84 ± 0.12 | 0.56 ± 0.18 | 0.53 ± 0.18 | 0.59 ± 0.16 | 0.48 ± 0.09 |

Summary and Discussion

Telmisartan has been shown to have anti-steatotic, -inflammatory and -fibrotic effects in STAM mice and therefore was used as the positive control in the present study. Treatment with telmisartan significantly decreased liver triglyceride contents, NAS and the fibrosis area compared with the Vehicle in NASH group in agreement with SMC Laboratories' historical data.

Gemcabene significantly reduced the fibrosis area compared with the Vehicle in NASH group, demonstrating an anti-fibrosis effect in the present study. The middle and high doses of gemcabene increased plasma ALP levels compared with the Vehicle in NASH group. The high dose of gemcabene also increased plasma creatinine levels compared with the Vehicle in NASH group. Plasma ALT levels were decreased in the gemcabene treatment groups, with statistical significance in the middle dose of gemcabene group. The low and high doses of gemcabene reduced NAS compared with the Vehicle in NASH group. Among NAS, the high dose of gemcabene reduced steatosis and ballooning scores at a degree comparable to telmisartan. Since hepatocyte ballooning is thought to be derived from oxidative stress-induced hepatocellular damage and is associated with disease progression of NASH (Fujii H et al. J. Atheroscler. Thromb. 2009; 16:893, Rangwala F et al. J. Pathol. 2011; 224:401), it suggests gemcabene improves NASH pathology by inhibiting hepatocyte damage and ballooning cell formation. Together, in the present study gemcabene has shown an anti-fibrotic effect at all the tested doses, as well demonstrating anti-NASH and hepatoprotective effects on the liver pathology of STAM mice. These data suggest gemcabene lead to liver improvements, and may positively affect inflammatory- and/or metabolism-related molecules which can be assessed by hepatic gene expression analyses or immunohistochemistry for specific targets Example 8

Hepatic Lipids in Male Sprague-Dawley Rats Treated with Gemfibrozil or Gemcabene.

Fifty-Six male Sprague-Dawley rats were obtained from Charles River Laboratories. All animals were allowed normal rat chow (Ralston-Purina) and water ad libitum in temperature-controlled rooms, under a 12-hour light, 12-hour dark cycle beginning with lights on at 6 AM. Rats were distributed to 7 groups of 8 rats per group. Rats were dosed daily between 6 and 10 AM by oral gavage using a suspension vehicle of 1.5% carboxymethyl cellulose plus 0.2% Tween-20 (Vehicle). Control animals received vehicle alone. The dosing vehicle volume represented 0.25% of body weight. PD 72953 is gemcabene. CI-719 is gemfibrozil. Compounds were administered daily to the seven treatment groups for fourteen consecutive days shown in table 16.

TABLE 16

| Group | Drug | Dose |
|---|---|---|
| 1 | Control | — |
| 2 | gemfibrozil | 100 mg/kg/day |
| 3 | PD 72953 | 1 mg/kg/day |
| 4 | PD 72953 | 3 mg/kg/day |
| 5 | PD 72953 | 10 mg/kg/day |
| 6 | PD 72953 | 30 mg/kg/day |
| 7 | PD 72953 | 100 mg/kg/day |

On the last day animals were sacrificed and the liver lipids were extracted and the content of triglyceride and cholesterol determined by the method of Homan and Anderson, Journal of Chromatography B, 708 (1998), 21-26. Liver pieces of approximately 500 mg were extracted for lipids and for determination of liver protein.

Figure 11A:
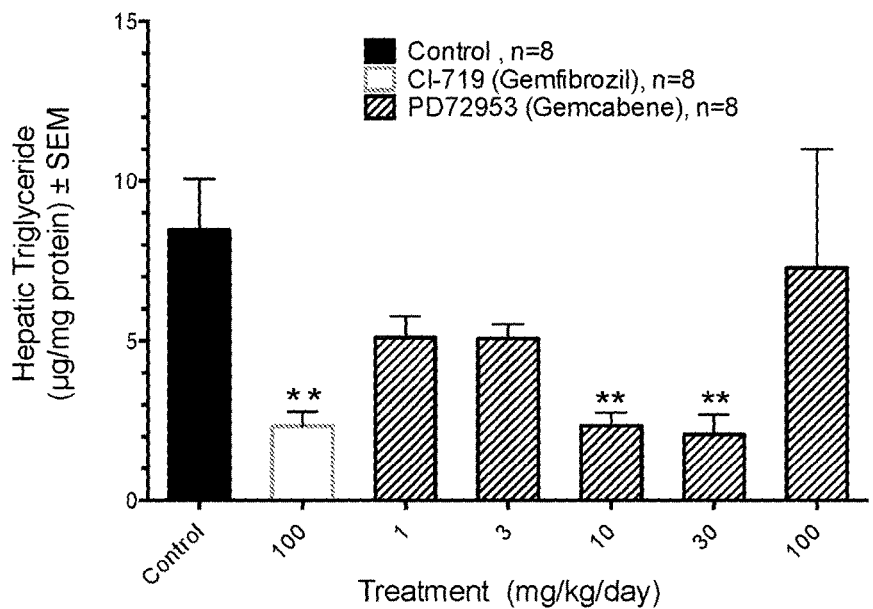
FIG. 11A is a bar graph showing the hepatic triglyceride levels in male Sprague-Dawley rats after treatment with gemfibrozil or gemcabene.
Figure 11B:
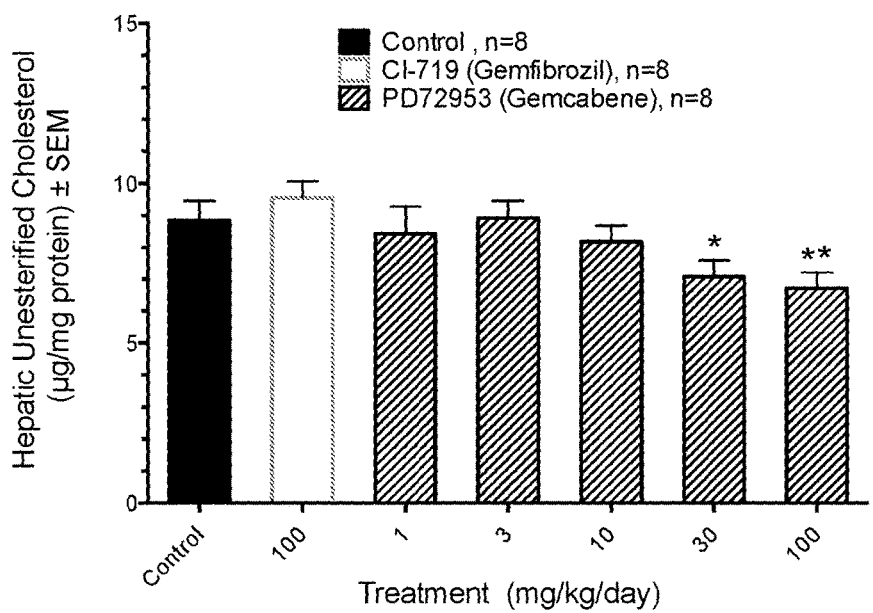
FIG. 11B is a bar graph showing the levels of hepatic unesterified cholesterol in male Sprague-Dawley rats after treatment with gemfibrozil or gemcabene.

Data are shown as mean±SEM of µg hepatic triglyceride/mg liver protein (FIG. 11A) or µg liver unesterified cholesterol/mg liver protein (FIG. 11B) for the rats treated with vehicle (control) or the indicated dose of gemfibrozil or gemcabene. Statistical analysis was ANOVA with post-hoc Fisher's PLSD (*p<0.05, **p<0.01).

Example 9

Fibrinogen Levels in Rats

Figure 12:
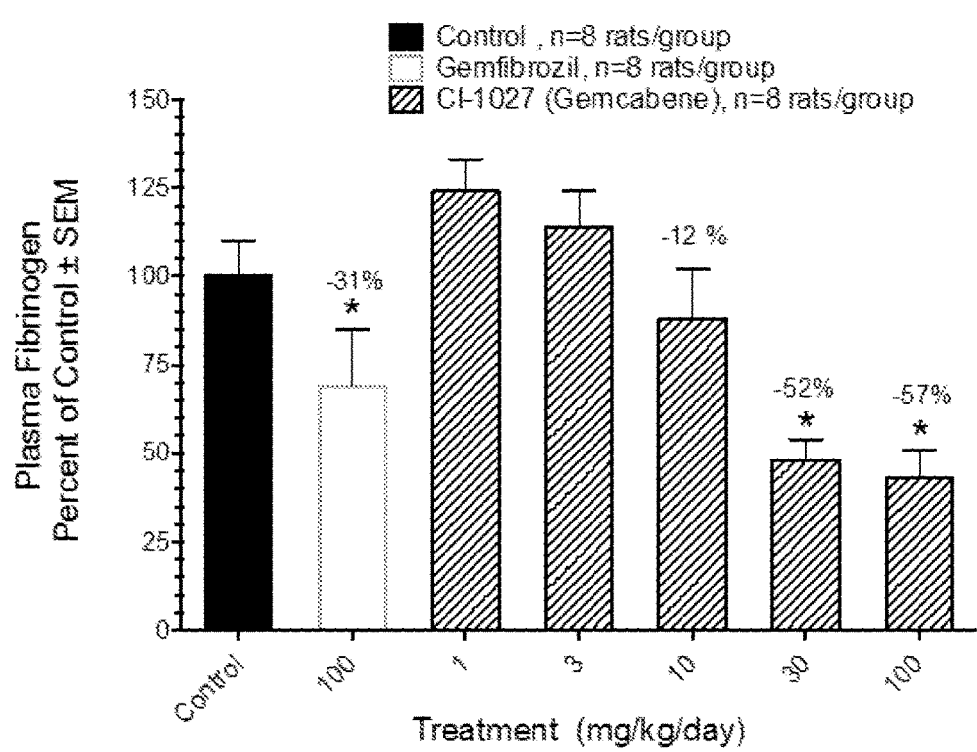
FIG. 12 is a bar graph showing the levels of plasma fibrinogen levels in male Sprague-Dawley rats after treatment with gemfibrozil or gemcabene.

Blood plasma was collected upon sacrifice from the rats in EXAMPLE 8. The plasma fibrinogen plasma levels were determined by electro immunoassay. Gemfibrozil at 100 mg/kg/day and PD 72953 at 30 mg/kg/day and 100 mg/kg/day showed significant reductions in plasma fibrinogen levels of 31, 52 and 57 percent respectively compared with control. Data are shown in FIG. 12 as mean±SEM of as percent of control fibrinogen levels. *p<0.001, two-sided unpaired t-test, compared to control.

Example 10

Fibrinogen Levels in Humans

In a post hoc analysis of fibrinogen from an 8-week, double-blind, randomized, placebo-controlled, dose-ranging study of the efficacy and safety of gemcabene (CI-1027) administered as monotherapy or in combination with atorvastatin in the treatment of hypercholesterolemic patients (Study A4141001). Blood samples to measure fibrinogen were collected at the beginning (Visit T5; Week 0) and the end (Visit T8, Week 8).

Analyses of covariance (ANCOVA) methods used in the original study A4141001 were again utilized in these analyses. For fibrinogen, baseline was defined as the last pretreatment visit, and endpoint was the last visit up to and including the day after last dose of medication. The least-squares means and p-values for change from baseline in fibrinogen were calculated using an ANCOVA model with the effects of baseline lipid value and treatment. Also, medians and p-values for percent change from baseline.

All patients included in the fibrinogen analysis were randomized and received at least 1 dose of study medication. Further, these patients must have had a baseline and at least 1 evaluable postbaseline measurement. This, consequently, was the definition for the modified intent-to treat (MITT) population.

Gemcabene 300, 600 and 900 mg monotherapy raised fibrinogen from baseline to endpoint by mean changes of 24.2, 23.6 and 12.9, respectively, compared with 37.2 for placebo. The rank-transformed data did not show significant differences between gemcabene and placebo as shown in Table 17.

TABLE 17

Gemcabene Monotherapy Verses Placebo - Change in Fibrinogen From Baseline to Endpoint (Modified Intent to Treat)

| | | Gemcabene Monotherapy | | |
|---|---|---|---|---|
| | Pbo N = 14 | 300 mg N = 13 | 600 mg N = 16 | 900 mg N = 16 |
| Baseline | | | | |
| Mean | 376.1 | 366.9 | 357.1 | 395.2 |
| Change | | | | |
| LS Mean (SE) | 37.2 (17.1) | 24.2 (18.5) | 23.6 (17.2) | 12.9 (17.2) |
| Difference | | −13.0 | −13.6 | −24.3 |
| 95% CI | | (−62.8, 36.7) | (−61.4, 34.2) | (−72.1, 23.5) |
| p-value | | 0.6059 | 0.5757 | 0.3172 |

Pbo = Placebo;
Difference = Gem xxmg − Placebo;
SE = Standard Error;
CI = Confidence Interval Co-administration of 600 mg gemcabene with atorvastatin aggregated over the dose range showed decreases in fibrinogen beyond atorvastatin monotherapy by −31.6 (p=0.0177) as shown in Table 18. Smaller decreases were observed with the co-administration of the 300 and 900 mg gemcabene with atorvastatin.

TABLE 18

Gemcabene + Atorvatatin Verses Atorvastatin - Change in Fibrinogen From Baseline to Endpoint (Modified Intent to Treat)

| | Ator 10, 40 or 80 mg Monotherapy N = 48 | Gem 300 mg + Ator 10, 40, or 80 mg N = 51 | Gem 600 mg Ator 10, 40, or 80 mg N = 47 | Gem 900 mg + Ator 10, 40, or 80 mg N = 47 |
|---|---|---|---|---|
| Baseline | | | | |
| Mean | 368.3 | 379.7 | 387.1 | 368.0 |
| Change | | | | |
| LS Mean (SE) | 32.9 (9.3) | 12.3 (9.0) | 1.3 (9.4) | 8.8 (9.4) |
| Difference | | −20.6 | −31.6 | −24.1 |
| 95% CI | | (−46.1, 4.8) | (−57.6, −5.4) | (−50.1, 1.9) |
| p-value | | 0.1120 | 0.0177 | 0.0689 |

Gem + Ator = Gemcabene in combination with atorvastatin;
Ator = Atorvastatin Monotherapy;
SE = Standard Error;
CI = Confidence Interval;
Difference = (Gem + Ator) − Ator.

The normal range of fibrinogen is about 150-300 mg/dL. To see the effect of gemcabene monotherapy or gemcabene in combination atorvastatin in subjects with fibrate levels above the normal range of fibrinogen, the data for the subgroup of subjects having a fibrinogen baseline level >400 mg/dL was examined. Table 19 shows the effect of various doses of gemcabene alone, atorvastatin alone or various dose combinations of gemcabene and atorvastatin on the change in baseline fibrinogen levels. Treatment with the combination of 600 mg of gemcabene in combination with statin at 10, 40 or 80 mg of atorvastatin caused a decrease of 22.5, 10.8 and 16.8% respectively.

TABLE 19

| Treatment | n | Mean Baseline FIBR | Mean Final FIBR | Mean Change FIBR | Mean % Change FIBR |
|---|---|---|---|---|---|
| Placebo | 6 | 456.0 | 477.0 | 21.0 | 4.4 |
| Gemcabene 300 mg | 5 | 427.8 | 454.4 | 26.6 | 6.7 |
| Gemcabene 600 mg | 5 | 452.4 | 411.0 | −41.4 | −9.3 |
| Gemcabene 900 mg | 8 | 448.8 | 435.9 | −12.9 | −3.2 |
| Gemcabene 300 mg + Atorvastatin 10 mg | 4 | 478.0 | 481.3 | 3.3 | 1.0 |
| Gemcabene 300 mg + Atorvastatin 40 mg | 5 | 449.8 | 460.8 | 11.0 | 2.3 |
| Gemcabene 300 mg + Atorvastatin 80 mg | 8 | 448.5 | 408.5 | −40.0 | −9.1 |
| Gemcabene 600 mg + Atorvastatin 10 mg | 6 | 495.8 | 386.7 | −109.2 | −22.5 |
| Gemcabene 600 mg + Atorvastatin 40 mg | 5 | 529.0 | 470.4 | −58.6 | −10.8 |
| Gemcabene 600 mg + Atorvastatin 80 mg | 5 | 450.2 | 375.6 | −74.6 | −16.8 |
| Gemcabene 900 mg + Atorvastatin 10 mg | 4 | 450.8 | 439.5 | −11.3 | −2.1 |
| Gemcabene 900 mg + Atorvastatin 40 mg | 3 | 426.3 | 413.0 | −13.3 | −3.1 |
| Gemcabene 900 mg + Atorvastatin 80 mg | 4 | 450.0 | 432.8 | −17.3 | −2.8 |
| Atorvastatin 10 mg | 7 | 442.4 | 445.4 | 3.0 | 0.9 |
| Atorvastatin 40 mg | 6 | 451.0 | 469.5 | 18.5 | 3.8 |
| Atorvastatin 80 mg | 3 | 425.7 | 434.7 | 9.0 | 1.9 |
| Total Subjects | 84 | | | | |

Table 20 shows the data for each dose of gemcabene with atorvastatin at any of the doses. 600 mg of gemcabene in combination with atorvastatin show a decrease of 17.1%.

TABLE 20

| Treatment | n | Mean Baseline FIBR | Mean Final FIBR | Mean Change FIBR | Mean % Change FIBR |
|---|---|---|---|---|---|
| Atorvastatin | 16 | 442.5 | 452.4 | 9.9 | 2.2 |
| Gemcabene | 18 | 443.9 | 434.1 | −9.8 | −2.2 |
| Gemcabene 300 mg + Atorvastatin | 17 | 455.8 | 441.0 | −14.8 | −3.4 |
| Gemcabene 600 mg + Atorvastatin | 16 | 491.9 | 409.4 | −82.6 | −17.1 |
| Gemcabene 900 mg + Atorvastatin | 11 | 443.8 | 429.8 | −14.0 | −2.6 |
| Placebo | 6 | 456.0 | 477.0 | 21.0 | 4.4 |
| Total Subjects | 84 | 442.5 | 452.4 | 9.9 | 2.2 |

Table 21 shows the data for gemcabene (Gem) monotherapy at 300, 600 and 900 mg.

TABLE 21

| | Placebo n = 6 | Gem 300 mg n = 5 | Gem 600 mg n = 5 | Gem 900 mg n = 8 |
|---|---|---|---|---|
| Baseline | | | | |
| Mean baseline Fibrinogen Change | 456.0 | 427.8 | 452.4 | 448.8 |
| LS Mean (SE) | 21.0 (26.4) | 26.0 (29.3) | −41.5 (28.9) | −13.0 (22.9) |
| Difference | | 5.0 | −62.5 | −34.0 |
| 95% CI | | (−73.8, 83.8) | (−104.7, 15.7) | (−103.8, 35.7) |
| p-Value | | 0.9004 | 0.1155 | 0.3338 |

Gem is Gemcabene, SE is Standard Error, CI is Confidence Interval, Difference is Gem-Placebo.

Table 22 shows the data for amalgamated Atorvastatin (Ator.) doses for placebo and each dose of Gemcabene (gem). The lowering of Gemcabene in combination with Atorvastatin showed a significant decrease of 91.7 mg/dL when compared with Atorvastatin alone (p=0.0002).

TABLE 22

| | Ator 10/40/80 N = 16 | Gem 300 mg + Ator 10/40/80 N = 17 | Gem 600 mg + Ator 10/40/80 N = 16 | Gem 900 mg + Ator 10/40/80 N = 11 |
|---|---|---|---|---|
| Baseline | | | | |
| Mean Change | 442.5 | 455.8 | 491.9 | 443.8 |
| LS Mean (SE) | 9.7 (16.0) | −14.8 (15.4) | −82.0 (16.0) | −14.2 (19.2) |
| Difference | | −24.5 | −91.7 | −23.9 |
| 95% CI | | (−68.8, 19.7) | (−139.0, −44.4) | (−73.4, 25.6) |
| p-Value | | 0.2725 | 0.0002 | 0.3338 |

Gem+Ator is Gemcabene in combination with atorvastatin; Ator is Atorvastatin monotherapy; SE is SE is Standard Error, CI is Confidence interval, Difference is (Gem+Ator)-ator.

Example 11

Representative examples of fixed dose combinations are provided in Table 16.

TABLE 16

| | Example 4D (450/40 mg G/A) | | Example 4E (300/10 mg G/A) | |
|---|---|---|---|---|
| Internal Ingredients | % w/w | mg/Tablet | % w/w | mg/Tablet |
| Gemcabene Calcium salt | 50.18 | 540.61 | 56.91 | 360.40 |
| Atorvastatin Calcium | 4.06 | 43.78 | 1.73 | 10.94 |
| Calcium Carbonate | 12.19 | 131.32 | 0.00 | 0.00 |
| Microcrystalline Cellulose, NF (PH 101) | 3.50 | 37.71 | 4.00 | 25.33 |
| Starch 1500 | 6.50 | 70.03 | 0.00 | 0.00 |

TABLE 16-continued

| | Example 4D (450/40 mg G/A) | | Example 4E (300/10 mg G/A) | |
| --- | --- | --- | --- | --- |
| | % w/w | mg/Tablet | % w/w | mg/Tablet |
| Croscarmellose Sodium | 3.00 | 32.32 | 3.00 | 19.00 |
| Hydroxypropyl Cellulose EXF | 5.30 | 57.10 | 5.00 | 31.67 |
| External Ingredients | | | | |
| Microcrystalline Cellulose, NF (PH 102) | 11.27 | 121.46 | 25.37 | 160.65 |
| Mannitol | 0.00 | 0.00 | 0.00 | 0.00 |
| Croscarmellose Sodium | 3.00 | 32.32 | 3.00 | 19.00 |
| Magnesium Stearate (Nonbovine) | 1.00 | 10.77 | 1.00 | 6.33 |
| To make core Tablets | 100.00 | 950.00 | 100.00 | 1077.42 |

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms bused in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

What is claimed is:

1. A method for treating or preventing hepatic steatosis, comprising administering to a subject in need thereof an effective amount of a compound of Formula I:

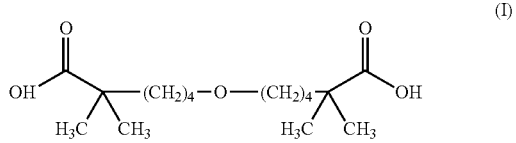

(I)

or a pharmaceutically acceptable salt or hydrate thereof.

2. The method for treating for preventing hepatic steatosis of claim 1, wherein the hepatic steatosis is NAFLD, or NASH.

3. The method for treating or preventing hepatic steatosis of claim 1, wherein the compound is the monocalcium salt of the compound of Formula I.

4. The method for treating or preventing hepatic steatosis of claim 1, wherein the compound is a hydrate of the monocalcium salt of the compound of Formula I.

5. A method of reducing the accumulation of liver fat in a subject at risk for liver fat accumulation comprising administering the compound of Formula I:

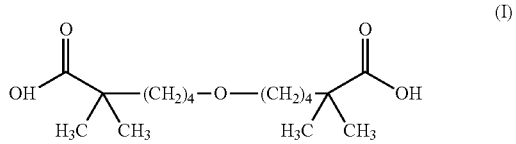

(I)

or a pharmaceutically acceptable salt or hydrate thereof, to the subject.

6. The method of reducing the accumulation of liver fat of claim 5, wherein the compound is the monocalcium salt of the compound of Formula I.

7. The method of reducing the accumulation of liver fat of claim 5, wherein the compound is a hydrate of the monocalcium salt of the compound of Formula I.

8. The method according to claim 5, wherein the subject has hepatic steatosis, type IIb hyperlipidemia, or familial combined hyperlipidemia.

9. The method of claim 5, wherein the daily dose of the compound is from about 50 mg to about 900 mg.

10. The method of claim 5, wherein the compound is administered in combination with simtuzumab, GS-4997, GS-974, GS-0976, INT-47 obeticholic acid, or cenicriviroc.

11. The method of claim 5, wherein the subject's risk of developing liver disease is reduced.

12. The method of claim 11, wherein the liver disease is nonalcoholic steatohepatitis (NASH), or nonalcoholic fatty liver disease (NAFLD), alcoholic hepatic steatosis or primary biliary cirrhosis.

13. The method of claim 5, wherein the subject has liver disease.

14. The method of claim 13, wherein the liver disease is nonalcoholic steatohepatitis (NASH), nonalcoholic fatty liver disease (NAFLD) or alcoholic hepatic steatosis.

15. The method of claim 9, wherein the subject is administered an additional lipid lowering agent.

16. The method of claim 15, wherein the additional lipid lowering agent is a cholesterol absorption inhibitor, a PCSK9 inhibitor, an ACC inhibitor, an ApoC-III inhibitor, an ACL-inhibitor, prescription fish oil, or a CETP inhibitor.

17. The method of claim 9, wherein the daily dose the gemcabene is of from about 150 mg to about 600 mg.

18. The method of claim 17, wherein the compound is administered in combination with a statin.

19. The method of claim 18, wherein the statin is atorvastatin, rosuvastatin, simvastatin, pravastatin, lovastatin, fluvastatin, or pitavastatin.

20. The method of claim 19, wherein the compound is administered as a fixed dose combination with the statin wherein the daily dose of the compound is 150 mg, 300 mg, 450, or 600 mg; and
   i) the statin is atorvastatin and the daily dose of atorvastatin is from 10 mg to 80 mg;
   ii) the statin is rosuvastatin and the daily dose of rosuvastatin is from 5 mg to 40 mg;
   iii) the statin is simvastatin and the daily dose of simvastatin is from 10 mg to 20 mg;
   iv) the statin is pravastatin and the daily dose of pravastatin is from 10 mg to 40 mg;
   v) the statin is lovastatin and the daily dose of lovastatin if from 20 mg to 40 mg;
   vi) the statin is fluvastatin and the daily dose of fluvastatin is from 20 mg to 40 mg; or
   vii) the statin is pitavastatin and the daily dose of pitavastatin is from 1 mg to 3 mg.

* * * * *